(12) United States Patent
Sano et al.

(10) Patent No.: US 7,476,508 B2
(45) Date of Patent: Jan. 13, 2009

(54) METHOD OF SCREENING AGENT FOR IMPROVING MEMORY AND LEARNING ABILITY

(75) Inventors: Yorikata Sano, Tokyo (JP); Kohei Inamura, Tokyo (JP); Shinobu Mochizuki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 105 days.

(21) Appl. No.: 10/542,560

(22) PCT Filed: Jan. 16, 2004

(86) PCT No.: PCT/JP2004/000333

§ 371 (c)(1),
(2), (4) Date: Jul. 18, 2005

(87) PCT Pub. No.: WO2004/065598

PCT Pub. Date: Aug. 5, 2004

(65) Prior Publication Data

US 2006/0116315 A1     Jun. 1, 2006

(30) Foreign Application Priority Data

Jan. 17, 2003  (JP) .............................. 2003-009884

(51) Int. Cl.
G01N 33/53    (2006.01)
G01N 33/566   (2006.01)
G01N 33/48    (2006.01)
G01N 31/00    (2006.01)
G01N 25/18    (2006.01)

(52) U.S. Cl. ................... 435/7.1; 436/501; 436/63; 436/2; 436/149

(58) Field of Classification Search ................ None
See application file for complete search history.

(56) References Cited

U.S. PATENT DOCUMENTS

2003/0224450 A1*  12/2003  Lee et al. .................... 435/7.1

FOREIGN PATENT DOCUMENTS

| WO | WO 01/32870 A1  | 5/2001  |
|----|-----------------|---------|
| WO | WO 02/46415 A2  | 6/2002  |
| WO | WO 02/077237 A2 | 10/2002 |
| WO | WO 03/012063 A2 | 2/2003  |
| WO | WO 03/012063 A3 | 2/2003  |
| WO | WO 03/085095 A2 | 10/2003 |

OTHER PUBLICATIONS

Supplementary Partial European Search Report for European Application No. EP 04 70 2849, dated Apr. 3, 2006.
Lee, N. et al., Expression and Characterization of Human Transient Receptor Potential Melastin 3 (hTRPM3), *J. Biol. Chem.*, 278 (23):20890-20897 (2003).
EBI Accession No. UNIPROT:Q9HCF6, Transient receptor potential cation channgel subfamily M member 3 (Long transient receptor potential channel 3) (LTrpC3) (Melastatin-2) (MLSN2), May 10, 2002.
EBI Accession No. EM_PRO: AB099661, *Homo sapiens* mRNA for hypothetical protein, complete cds. clone:pFCP161615, Jan. 10, 2003.
Vallée, M. et al., "Neurosteroids: Deficient Cognitive Performance in Aged Rats Depends on Low Pregnenolone Sulfate Levels in the Hippocampus," Proc. Natl. Acad. Sci. USA, vol. 94, pp. 14865-14870, (Dec. 1997).
Kawato, K., "Neurosteroid: No Kaiba de Gosei sare, Kioku Gakushu o Kasseika Shitari Yokusei Sitari Suru Dai 4 Sedal no No no Joho Dentatsu Busshitsu," Biophysics, vol. 41, No. 6, pp. 290-294, (2001).

* cited by examiner

*Primary Examiner*—Olga N Chernyshev
(74) *Attorney, Agent, or Firm*—Finnegan, Henderson, Farabow, Garrett, & Dunner, LLP

(57) ABSTRACT

A screening tool and a screening method of a substance which is useful as an agent for improving the memory, an agent for improving learning ability, and/or an antidementia agent; a polypeptide, a polynucleotide, a vector, and a cell which may be used in the above screening; and a novel agent for improving the memory, a novel agent for improving learning ability, and/or a novel antidementia agent are disclosed. The above screening tool is composed of a calcium-permeable nonselective cation channel or a cell expressing the channel.

2 Claims, 3 Drawing Sheets

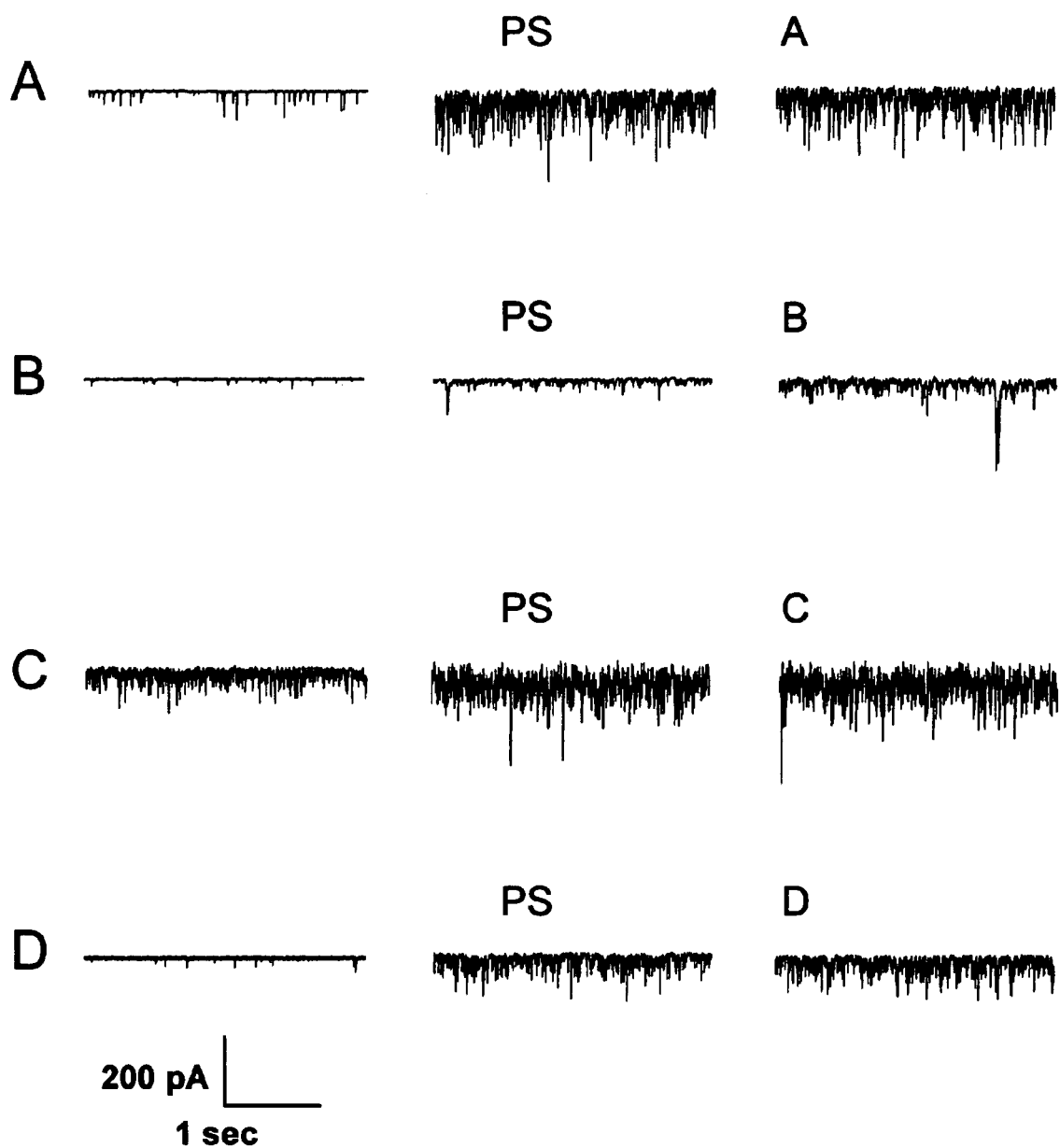

METHOD OF SCREENING AGENT FOR IMPROVING MEMORY AND LEARNING ABILITY

This application is a U.S. national phase filing under 35 U.S.C. § 371 of PCT Application PCT/JP2004/000333, filed Jan. 16, 2004, which claims priority to Japanese Application No. 2003-009884, filed Jan. 17, 2003. Both of these applications are incorporated herein by reference in their entirety.

TECHNICAL FIELD

The present invention relates to a screening method of an agent for improving the memory, an agent for improving learning ability, and/or an antidementia agent.

BACKGROUND ART

Pregnenolone sulfate (hereinafter referred to as "PS") is a sulfate ester of pregnenolone, which is a steroid hormone generated by cholesterol metabolism. It is known that pregnenolone is further metabolized to generate 17-hydroxypregnenolone or progesterone (non-patent references 1 and 2). PS is generated in the adrenal gland and brain. It is considered that PS generated in the brain acts on only functions of the center of the brain. Such a central nervous system-acting steroid hormone is called a neurosteroid (non-patent reference 3).

The hippocampus is known as an area associated with memory and learning in the brain, and it is known that cytochrome P450scc, an enzyme associated with PS synthesis, exists in neurons in the hippocampus (non-patent reference 4). Further, it is known that cytochrome P450scc exists in intracellular mitochondria, and that PS is generated from cholesterol transported into mitochondria. Furthermore, it is known that the transport of cholesterol into mitochondria is triggered by a calcium influx into cells (non-patent reference 3). Therefore, the calcium influx into cells acts as a trigger of PS synthesis.

To reveal a PS function in the central nervous system, an amount of PS contained in the hippocampus was measured, and as a result, it was found that the concentration of PS is reduced with aging. Further, it was found that the memory and learning ability are reduced in correlation with the PS concentration (non-patent reference 5), and PS is thus considered to be involved in memory and learning. The effects of PS on memory and learning were analyzed closely and carefully, and it was found that PS causes an increase of acetylcholine, a neurotransmitter released from the synaptic terminal, a promotion of frequency in the hippocampal spike, and long term potentiation (LTP), using hippocampal slices (non-patent references 3, 6, and 7). These results show an enhancement of neurotransmission by PS, and thus it was found that PS is involved in memory and learning via the promotion of neurotransmission (non-patent reference 3).

Actually, when PS was administered to aged rats exhibiting a decreased memory and learning ability, the memory and learning ability were improved (non-patent reference 5).

As described above, PS is deeply involved in the mechanism of memory and learning, and a reduced amount of PS produced with aging promotes a reduction in the memory and learning ability, and as a result, dementia develops.

Since the memory and learning ability are improved by an administration of PS, an activity of antidementia can be expected by administering PS to a patient suffering from dementia with aging or enhancing the mechanism of PS.

However, PS has a low transferability into the brain, and thus, it is difficult to use PS per se as an antidementia agent. In addition, a molecule directly targeted by PS is unknown, and it is unknown how the above-described increased hippocampal LTP and increased release of the neurotransmitter are triggered. There is a report in which the existence of an unknown target molecule capable of improving the memory and learning by a direct action of PS is suggested (non-patent reference 3).

A human novel melastatin-like protein is encoded by a human gene similar to a Melastatin gene belonging to a TRPM (Transient Receptor Potential Melastatin) channel family. The sequence of the gene encoding the human novel melastatin-like protein is known, but functions of the protein encoded by the gene, particularly functions in a living body, are unknown (patent reference 1). The sequence of a human TRICH (transporters and ion channels) is known (patent reference 2), and it is described in patent reference 2 that the human TRICH plays a role in transports, the nervous system, muscles, immunity, or cell-proliferation-related diseases. However, experimental supports therefor are not disclosed in patent reference 2, and functions of the human TRICH in a living body are unknown.

(non-patent reference 1) Nippon Rinsho, 1999, vol. 57, p. 162-165
(non-patent reference 2) Nippon Rinsho, 1999, vol. 57, p. 166-169
(non-patent reference 3) Seibutsu Butsuri, 2001, vol. 41, p. 290-294
(non-patent reference 4) Endocrinology, (U.S.A.), 2001, vol. 142, p. 3578-3589
(non-patent reference 5) Proceedings of the National Academy of Sciences of the United States of America, (U.S.A.), 1997, vol. 94, p. 14865-14870
(non-patent reference 6) Epilepsy Research, (Netherlands), 1999, vol. 33, p. 23-29
(non-patent reference 7) Brain Research, (U.S.A.), 2002, vol. 951, p. 237-242
(patent reference 1) International Publication No. WO01/32870
(patent reference 2) International Publication No. WO02/77237

DISCLOSURE OF INVENTION

An object of the present invention is to provide a screening tool and a screening method for obtaining a substance useful as an agent for improving the memory, an agent for improving learning ability, and/or an antidementia agent; a novel polypeptide, a novel polynucleotide, a novel vector, and a novel cell, which may be used in the screening; and a novel agent for improving the memory, a novel agent for improving learning ability, and/or a novel antidementia agent.

The present inventors have conducted intensive studies, and as a result, obtained novel genes encoding polypeptides consisting of the amino acid sequences of SEQ ID NOS: 2, 4, and 6, and found that these polypeptides are novel calcium-permeable nonselective cation channels. Further, the present inventors found that the genes are expressed in the brain, particularly the hippocampus associated with memory and learning; and that the polypeptides are specifically activated by PS. In this connection, PS is a neurosteroid which is associated with memory and-learning via an enhancement of neurotransmission, and it is known that the administration of PS can improve the memory and learning ability. The present inventors found that the polypeptides and cells expressing the same are useful as a screening tool for obtaining a substance useful as an agent for improving the memory, an agent for improving learning ability, and/or an antidementia agent, and provided a novel screening method. Further, the present inventors obtained agents capable of activating the above polypeptides by the screening method of the present invention, and confirmed that the activating agents exhibit activities of improving the memory, improving learning ability, and/or antidementia, by promoting neurotransmission in the neurons, and thus the present invention was completed.

The present invention relates to:

[1] a screening tool of an agent for improving the memory, an agent for improving learning ability, and/or an antidementia agent, consisting of
(1) a polypeptide consisting of the amino acid sequence of SEQ ID NO: 2, 4, or 6,
(2) a polypeptide comprising the amino acid sequence of SEQ ID NO: 2, 4, or 6, and exhibiting a calcium ion-permeable ion channel activity by activation with pregnenolone sulfate,
(3) a polypeptide comprising an amino acid sequence in which 1 to 10 amino acids are deleted, substituted, and/or inserted in the amino acid sequence of SEQ ID NO: 2, 4, or 6, and exhibiting a calcium ion-permeable ion channel activity by activation with pregnenolone sulfate,
(4) a polypeptide consisting of an amino acid sequence having a 90% or more homology with that of SEQ ID NO: 2, 4, or 6, and exhibiting a calcium ion-permeable ion channel activity by activation with pregnenolone sulfate, or
(5) a cell expressing at least one of the polypeptides (1) to (4);

[2] a screening method of an agent for improving the memory, an agent for improving learning ability, and/or an antidementia agent, comprising the steps of:
(a) bringing a substance to be tested into contact with the screening tool of [1],
(b) analyzing a channel activity thereof, and
(c) selecting a substance capable of activating the channel;

[3] an agent for improving the memory, an agent for improving learning ability, and/or an antidementia agent, containing as an active ingredient a substance capable of activating at least one of the polypeptides (1) to (4);

[4] a process for manufacturing a pharmaceutical composition for improving the memory, improving learning ability, and/or antidementia, comprising the steps of:
(a) bringing a substance to be tested into contact with the polypeptide or cell of [1],
(b) analyzing a channel activity thereof, and
(c) preparing a medicament containing the substance;

[5] (1) a polypeptide consisting of the amino acid sequence of SEQ ID NO: 2, 4, or 6,
(2) a polypeptide comprising the amino acid sequence of SEQ ID NO: 2, 4, or 6, and exhibiting a calcium ion-permeable ion channel activity by activation with pregnenolone sulfate, or
(3) a polypeptide comprising an amino acid sequence in which 1 to 10 amino acids are deleted, substituted, and/or inserted in the amino acid sequence of SEQ ID NO: 4 or 6, and exhibiting a calcium ion-permeable ion channel activity by activation with pregnenolone sulfate;

[6] a polynucleotide encoding the polypeptide of [5];
[7] a vector comprising the polynucleotide of [6];
[8] a cell comprising the polynucleotide of [6];
[9] a process for producing the polypeptide of [5], characterized by using the polynucleotide of [6], the vector of [7], or the cell of [8];

[10] a screening method of a substance capable of activating the polypeptide of [5], comprising the steps of:
(a) bringing a substance to be tested into contact with the polypeptide of [5] or a cell expressing the polypeptide,
(b) analyzing a channel activity, and
(c) selecting a substance capable of activating the channel;

[11] an agent for improving the memory, an agent for improving learning ability, and/or an antidementia agent, containing as an active ingredient a substance obtainable by the screening method of [2], with the proviso that the substance is not pregnenolone sulfate;

[12] a method for preventing and/or treating a reduction in memory, a reduction in learning ability, and/or dementia, comprising administering to a subject in need thereof a substance obtainable by the screening method of [2] in an amount effective therefor, with the proviso that the substance is not pregnenolone sulfate; and

[13] use of a substance obtainable by the screening method of [2], in the manufacture of a pharmaceutical composition for improving the memory, improving learning ability, and/ or antidementia.

The present invention includes use of any one of the polypeptides of (1) to (4) in [1] or the cell of (5) in [1], in the screening of an agent for improving the memory, an agent for improving learning ability, and/or an antidementia agent.

BRIEF DESCRIPTION OF THE DRAWINGS

FIG. 4 is a graph showing spontaneous excitatory postsynaptic currents (sEPSCs) when any one of compound A (10 μmol/L), compound B (10 μmol/L), compound C (10 μmol/L), compound D (1 μmol/L), and PS (10 μmol/L) was added to primary cultured neurons derived from rat cerebral cortex. As results A, B, C, and D, responses obtained from different cells are exemplified. The left column, the central column, and the right column (i.e., from left to right) show the results when a buffer, PS, and compounds (A, B, C, or D), respectively. The first to fourth lines (i.e., from top to bottom) show the results of compounds A, B, C, and D, respectively.

BEST MODE FOR CARRYING OUT THE INVENTION

Figure 1:
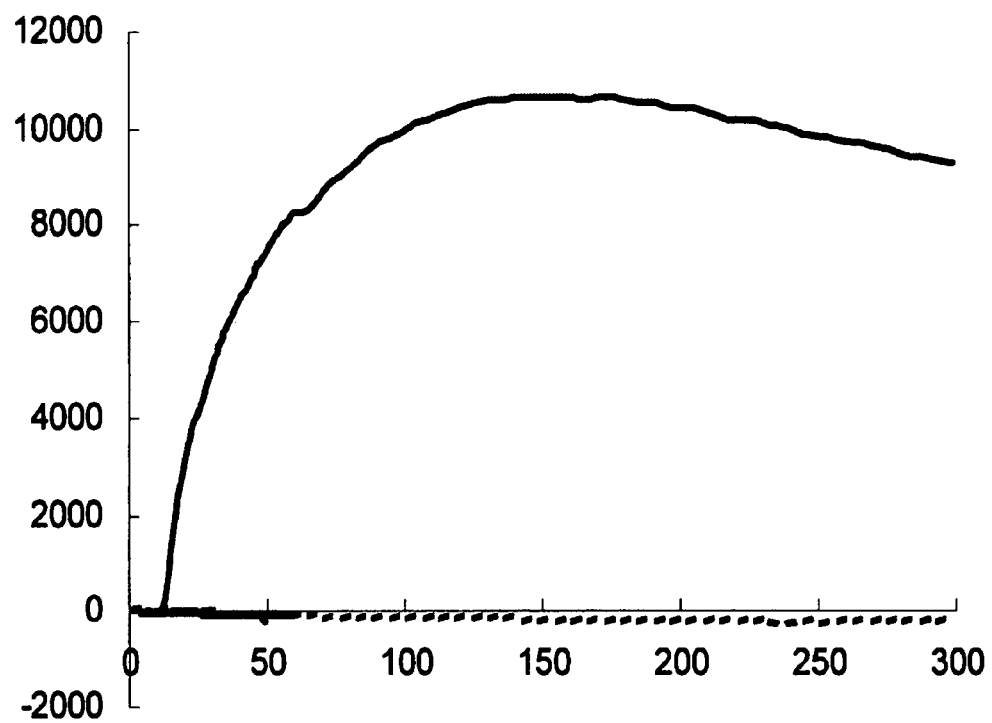
FIG. 1 is a graph showing the results of a calcium influx, as a time course of fluorescent intensity (unit=counts), when PS (10 μmol/L) was added to HEK293 cells in which a gene encoding the polypeptide consisting of the amino acid sequence of SEQ ID NO: 2 was expressed. The vertical axis indicates a change of fluorescent intensity by the calcium influx, and the horizontal axis indicates a time (seconds). The solid line indicates the result of the transformants obtained in Example 3, and the dotted line indicates that of control cells.

[1] Screening tool of an agent for improving the memory, an agent for improving learning ability, and/or an antidementia agent according to the present invention The screening tool of the present invention includes a polypeptide-type screening tool and a cell-type screening tool.

(1) Polypeptide-Type Screening Tool

As the polypeptide which may be used as the polypeptide-type screening tool according to the present invention of an agent for improving the memory, an agent for improving learning ability, and/or an antidementia agent, there may be mentioned, for example, (i) a polypeptide consisting of the amino acid sequence of SEQ ID NO: 2, 4, or 6;
(ii) (a) a polypeptide comprising the amino acid sequence of SEQ ID NO: 2, 4, or 6, and exhibiting a calcium ion-permeable ion channel activity by activation with PS; or (b) a polypeptide comprising an amino acid sequence in which 1 to 10 amino acids are deleted, substituted, and/or inserted in the amino acid sequence of SEQ ID NO: 2, 4, or 6, and exhibiting a calcium ion-permeable ion channel activity by activation with PS [hereinafter, a polypeptide for a tool consisting of any one of the polypeptides (a), and a polypeptide for a tool consisting of any one of the polypeptides (b) are collectively referred to as polypeptides functionally equivalent for a tool]; or
(iii) a polypeptide consisting of an amino acid sequence having a 90% or more homology with that of SEQ ID NO: 2, 4, or 6, and exhibiting a calcium ion-permeable ion channel activity by activation with PS (hereinafter referred to as a homologous polypeptide for a tool).

Hereinafter, the polypeptides which may be used as the polypeptide-type screening tool of the present invention are collectively referred to as polypeptides for a screening tool.

"To exhibit a calcium ion-permeable ion channel activity by activation with PS" as used herein means, when a cell expressing a polypeptide of interest is stimulated with PS, and then an amount of current response or calcium influx in the cell is compared with that in another cell expressing the polypeptide of interest but not stimulated with PS, the amount of current response or calcium influx in the PS-stimulated cell is higher than that in the PS-nonstimulated cell. Comparison of the amounts of current response may be carried out, for example, in accordance with the method described in Example 4. Comparison of the amounts of calcium influx may be carried out, for example, by the method described in Example 5 or 6. As the degree of the increase in the amount of current response or calcium influx, when a significant test is carried out with respect to that in PS-nonstimulated cells, the P value is preferably 0.05 or less, more preferably 0.01 or less.

As the polypeptide for a screening tool, a polypeptide further exhibiting a cesium, sodium, and magnesium ion-permeable ion channel activity is preferable.

The polypeptides consisting of the amino acid sequences of SEQ ID NOS: 2, 4, and 6, which may be used as the polypeptide-type screening tool of the present invention, are novel calcium-permeable nonselective cation channels derived from a human, a mouse, and a rat, respectively.

The amino acid sequence (1554 amino acids) of SEQ ID NO: 2 is different by three amino acids from an amino acid sequence deduced from a known gene (SEQ ID NO: 24 described in WO01/32870) encoding a human novel melastatin-like protein, in which functions thereof in a living body are unknown. More particularly, glutamine (Gln), arginine (Arg), and asparagine (Asn) at the 1517, 1539, and 1554 positions in the amino acid sequence of SEQ ID NO: 2 are arginine (Arg), lysine (Lys), and threonine (Thr) in the amino acid sequence deduced from the gene encoding the human novel melastatin-like protein, respectively. Further, the amino acid sequence of SEQ ID NO: 2 accords with 1544 amino acids in a deduced amino acid sequence (1707 residues; SEQ ID NO: 10 described in WO02/77237) of a human TRICH. Furthermore, J. B. C, 278, 20890-20897, 2003, published after the priority date of the present application, discloses an hTRPM3 amino acid sequence having a homology with that of SEQ ID NO: 2. However, no references disclose or suggest that the polypeptides are activated by PS and involved in memory and learning.

As the polypeptide functionally equivalent for a tool, which may be used as the polypeptide-type screening tool of the present invention, (a) a polypeptide consisting of an amino acid sequence in which 1 to 10 (more preferably 1 to 7, still more preferably 1 to 5, most preferably 1 or 2) amino acids in total are deleted, substituted, inserted, and/or added at one or plural positions in the amino acid sequence of SEQ ID NO: 2, 4, or 6, and exhibiting a calcium ion-permeable ion channel activity by activation with PS, or (b) a polypeptide comprising the amino acid sequence of SEQ ID NO: 2, 4, or 6, and exhibiting a calcium ion-permeable ion channel activity by activation with PS, is preferable.

The polypeptide comprising the amino acid sequence of SEQ ID NO: 2, 4, or 6, and exhibiting a calcium ion-permeable ion channel activity by activation with PS includes, for example, a polypeptide in which an appropriate marker sequence or the like is added to the N-terminus and/or the C-terminus of the polypeptide consisting of the amino acid sequence of SEQ ID NO: 2, 4, or 6 (i.e., a fusion polypeptide), so long as it exhibits a calcium ion-permeable ion channel activity by activation with PS.

As the marker sequence, a sequence for easily carrying out a confirmation of polypeptide expression, a confirmation of intracellular localization thereof, a purification thereof, or the like may be used. As the sequence, there may be mentioned, for example, a FLAG epitope, a hexa-histidine tag, a hemagglutinin tag, a myc epitope, or the like.

In the homologous polypeptide for a tool, which may be used as the polypeptide-type screening tool of the present invention, the homology with the amino acid sequence of SEQ ID NO: 2, 4, or 6 is 90% or more, preferably 95% or more, more preferably 98% or more, most preferably 99%.

The term "homology" as used herein means a value obtained by a ClustalV method using MegAlign (DNASTAR).

(2) Cell-type screening tool

The cell which may be used as the cell-type screening tool of the present invention (hereinafter referred to as a cell for a screening tool) is not particularly limited, so long as it expresses the polypeptide for a screening tool when used as the cell-type screening tool. For example, a cell is transformed with a foreign gene to obtain a transformant artificially expressing the polypeptide. Alternatively, a naturally occurring cell expressing the polypeptide for a screening tool, or a cell line thereof may be used as the cell for a screening tool.

As to the cell for a screening tool, which may be used as the cell-type screening tool of the present invention, a transformant is preferable. As such a transformant, there may be mentioned, for example,
(i) a transformant expressing the polypeptide consisting of the amino acid sequence of SEQ ID NO: 2, 4, or 6;
(ii) a transformant expressing the polypeptide functionally equivalent for a tool; or
(iii) a transformant expressing the homologous polypeptide for a tool.

[2] Polypeptide and Polynucleotide of the Present Invention

The polypeptide of the present invention includes
(i) the polypeptide consisting of the amino acid sequence of SEQ ID NO: 2, 4, or 6; and
(ii) (a) the polypeptide comprising the amino acid sequence of SEQ ID NO: 2, 4, or 6, and exhibiting a calcium ion-permeable ion channel activity by activation with PS, or (b) the polypeptide comprising an amino acid sequence in which 1 to 10 amino acids are deleted, substituted, and/or inserted in the amino acid sequence of SEQ ID NO: 4 or 6, and exhibiting a calcium ion-permeable ion channel activity by activation with PS (hereinafter referred to as a modified polypeptide functionally equivalent).

As the polypeptide of the present invention, a polypeptide further exhibiting a cesium, sodium, and magnesium ion-permeable ion channel activity is preferable.

As the modified polypeptide functionally equivalent, (a) a polypeptide consisting of an amino acid sequence in which 1 to 10 (more preferably 1 to 7, most preferably 1 to 5) amino acids in total are deleted, substituted, inserted, and/or added at one or plural positions in the amino acid sequence of SEQ ID NO: 4 or 6, and exhibiting a calcium ion-permeable ion channel activity by activation with PS, or (b) a polypeptide comprising the amino acid sequence of SEQ ID NO: 2, 4, or 6, and exhibiting a calcium ion-permeable ion channel activity by activation with PS, is preferable.

The polynucleotide of the present invention is not particularly limited, so long as it encodes the polypeptide of the present invention. As the polynucleotide of the present invention, there may be mentioned, for example, a polynucleotide encoding "the polypeptide consisting of the amino acid sequence of SEQ ID NO: 2, 4, or 6", or a polynucleotide encoding the modified polypeptide functionally equivalent.

More particularly, as the polynucleotide of the present invention, a polynucleotide consisting of the nucleotide sequence consisting of nucleotides 50-4714 of SEQ ID NO: 1, a polynucleotide consisting of the nucleotide sequence consisting of nucleotides 218-4993 of SEQ ID NO: 3, or a polynucleotide consisting of the nucleotide sequence consisting of nucleotides 182-4882 of SEQ ID NO: 5, is preferable.

The term "polynucleotide" as used herein includes DNA and RNA.

[3] Process for producing screening tool, polypeptide, polynucleotide, and cell of the present invention Gene recombination techniques can be carried out in accordance with known methods (for example, "Molecular Cloning-A Laboratory Manual", Cold Spring Harbor Laboratory, NY, 1989, WO02/052000, or WO02/053730).

A process for producing the polynucleotide of the present invention, or a process for producing the polynucleotide encoding the polypeptide for a screening tool (hereinafter referred to as the polynucleotide for a screening tool) is not particularly limited. As the process, there may be mentioned, for example, (a) a method utilizing a polymerase chain reaction (PCR), (b) a method utilizing conventional genetic engineering techniques (i.e., a method for selecting a transformant containing the desired cDNA from strains transformed with a cDNA library), (c) a chemical synthesis method, or the like. These methods will be explained in this order hereinafter.

In the method using PCR [the above method (a)], the polynucleotide of the present invention or the polynucleotide for a screening tool may be produced, for example, by the following procedure.

mRNA is extracted from cells (for example, human, mouse, or rat cells) or tissue capable of producing the polypeptide of the present invention or the polypeptide for a screening tool. A primer set consisting of a pair of primers, between which full-length mRNA corresponding to the polypeptide or a partial region of the mRNA is located, is synthesized on the basis of the base sequence of a polynucleotide encoding the polynucleotide. Full-length cDNA encoding the polypeptide of the present invention or the polypeptide for a screening tool, or a part of the full-length cDNA may be obtained, by adjusting reaction conditions (for example, denaturation temperature, conditions for adding a denaturing agent, or the like) and performing a reverse transcriptase-polymerase chain reaction (RT-PCR).

Alternatively, full-length cDNA encoding the polypeptide or a part of the cDNA may be obtained, by performing PCR using, as a template, cDNA prepared using reverse transcriptase and mRNA derived from cells (for example, human, mouse, or rat cells) or tissue capable of producing the polypeptide, or commercially available cDNA derived from human, mouse, or rat cells or tissue.

The polypeptide may be manufactured by inserting the resulting full-length cDNA or a part thereof into an appropriate expression vector and expressing it in host cells.

In the method using conventional genetic engineering techniques [the above method (b)], the polynucleotide of the present invention or the polynucleotide for a screening tool may be produced, for example, by the following procedure.

First, single-stranded cDNA is synthesized by using reverse transcriptase from mRNA prepared by the above-mentioned PCR method as a template, and then double-stranded cDNA is synthesized from the single-stranded cDNA.

Next, a recombinant plasmid comprising the double-stranded cDNA is prepared and introduced into *Escherichia coli*, such as a DH5α strain, HB101 strain, or JM109 strain, thereby transforming the strain. A transformant is selected using a drug resistance against, for example, tetracycline, ampicillin, or kanamycin as a marker. Transformation of a host cell can be carried out, for example, by Hanahan's method (Hanahan, D. J., Mol. Biol., 166, 557-580, 1983) when the host cell is *Escherichia coli*. Further, a commercially available competent cell may be used. As a vector, not only a plasmid, but also a phage vector such as lambda phages may be used.

As a method for selecting a transformant containing the desired cDNA from the resulting transformants, for example, (1) a screening method utilizing hybridization with a synthetic oligonucleotide probe, or (2) a screening method utilizing hybridization with a probe prepared by PCR, may be used.

The polynucleotide of the present invention or the polynucleotide for a screening tool may be obtained from the resulting transformant of interest in accordance with known methods, for example, by separating a fraction corresponding to plasmid DNA from the cells and cutting out the cDNA region from the plasmid DNA.

In the method using a chemical synthesis method [the above method (c)], the polynucleotide of the present invention or the polynucleotide for a screening tool may be produced, for example, by binding DNA fragments produced by a chemical synthesis method. Each DNA can be synthesized using a DNA synthesizer [for example, Oligo 1000M DNA Synthesizer (Beckman) or 394 DNA/RNA Synthesizer (Applied Biosystems)].

Determination of the DNA sequences obtained by the above-mentioned methods can be carried out by, for example, a Maxam-Gilbert chemical modification method (Maxam, A. M. and Gilbert, W., "Methods in Enzymology", 65, 499-559, 1980) or a dideoxynucleotide chain termination method (Messing, J. and Vieira, J., Gene, 19, 269-276, 1982).

An isolated polynucleotide of the present invention or polynucleotide for a screening tool is re-integrated into an appropriate vector DNA and a host cell (including a eucaryotic host cell and a procaryotic host cell) may be transformed by the resulting expression vector, to obtain the cell of the present invention or the cell for a screening tool. Further, it is possible to express the polynucleotide in a desired host cell, by introducing an appropriate promoter and a sequence related to the gene expression into the vector.

In the eucaryotic host cells, for example, cells of vertebrates, insects, and yeast are included. As the vertebral cell, there may be mentioned, for example, a simian COS cell (Gluzman, Y., Cell, 23, 175-182, 1981), a dihydrofolate reductase defective strain of a Chinese hamster ovary cell (CHO) (Urlaub, G. and Chasin, L. A., Proc. Natl. Acad. Sci. USA, 77, 4216-4220, 1980), a human fetal kidney derived HEK293 cell, or a 293-EBNA cell (Invitrogen) obtained by introducing an EBNA-1 gene of Epstein Barr Virus into HEK293 cell.

As an expression vector for a vertebral cell, a vector containing a promoter positioned upstream of the polynucleotide to be expressed, an RNA splicing site, a polyadenylation site, a transcription termination sequence, and the like may be generally used. The vector may further contain a replication origin, if necessary. As the expression vector, there may be mentioned, for example, pSV2dhfr containing an SV40 early promoter (Subramani, S. et al., Mol. Cell. Biol., 1, 854-864, 1981), pEF-BOS containing a human elongation factor promoter (Mizushima, S. and Nagata, S., Nucleic Acids Res., 18, 5322, 1990), or pCEP4 containing a cytomegalovirus promoter (Invitrogen).

When the COS cell is used as the host cell, a vector which has an SV40 replication origin, can perform an autonomous replication in the COS cell, and has a transcription promoter, a transcription termination signal, and an RNA splicing site, may be used as the expression vector. As the vector, there may be mentioned, for example, pME18S (Maruyama, K. and Takebe, Y., Med. Immunol., 20, 27-32, 1990), pEF-BOS (Mizushima, S. and Nagata, S., Nucleic Acids Res., 18, 5322, 1990), or pCDM8 (Seed, B., Nature, 329, 840-842, 1987).

The expression vector may be incorporated into COS cells by, for example, a DEAE-dextran method (Luthman, H. and Magnusson, G., Nucleic Acids Res., 11, 1295-1308, 1983), a calcium phosphate-DNA coprecipitation method (Graham, F. L. and van der Ed, A. J., Virology, 52, 456-457, 1973), a method using a commercially available transfection reagent (for example, FuGENE™6 Transfection Reagent; Roche Diagnostics), or an electroporation method (Neumann, E. et al., EMBO J., 1, 841-845, 1982).

When the CHO cell is used as the host cell, a transformant capable of stably producing the polypeptide of the present invention or the polynucleotide for a screening tool can be obtained by carrying out a co-transfection of an expression vector comprising the polynucleotide of the present invention or the polynucleotide for a screening tool, together with a vector capable of expressing a neo gene which functions as a G418 resistance marker, such as pRSVneo (Sambrook, J. et al., "Molecular Cloning-A Laboratory Manual", Cold Spring Harbor Laboratory, NY, 1989) or pSV2-neo (Southern, P. J. and Berg, P., J. Mol. Appl. Genet., 1, 327-341, 1982), and selecting a G418 resistant colony.

When the 293-EBNA cell is used as the host cell, for example, pCEP4 (Invitrogen) containing a replication origin of Epstein Barr Virus and capable of performing an autonomous replication in the 293-EBNA cell may be used as the expression vector.

The transformant may be cultured in accordance with the conventional method, and the polypeptide of the present invention or the polynucleotide for a screening tool is transmembranously produced. As a medium to be used in the culturing, a medium commonly used in a desired host cell may be appropriately selected. In the case of the COS cell, for example, a medium such as an RPMI-1640 medium or a Dulbecco's modified Eagle's minimum essential medium (DMEM) may be used, by supplementing it with a serum component such as fetal bovine serum (FBS) if necessary. In the case of the 293-EBNA cell, a medium such as a Dulbecco's modified Eagle's minimum essential medium (DMEM) with a serum component such as fetal bovine serum (FBS) and G418 may be used.

The polypeptide of the present invention or the polynucleotide for a screening tool produced by culturing the transformants of the present invention may be separated and purified therefrom by various known separation techniques making use of the physical properties, chemical properties and the like of the polypeptide. More particularly, the above polypeptide may be purified by treating the cells or cell membrane fraction containing the polypeptide with a commonly used treatment, for example, a treatment with a protein precipitant, ultrafiltration, various liquid chromatography techniques such as molecular sieve chromatography (gel filtration), adsorption chromatography, ion exchange chromatography, affinity chromatography, or high performance liquid chromatography (HPLC), or dialysis, or a combination thereof.

When the polypeptide of the present invention or the polynucleotide for a screening tool is expressed as a fusion protein with a marker sequence in frame, identification of the expression of the polypeptide, purification thereof, or the like may be easily carried out. As the marker sequence, there may be mentioned, for example, a FLAG epitope, a hexa-histidine tag, a hemagglutinin tag, or a myc epitope. Further, by inserting a specific amino acid sequence recognized by a protease such as enterokinase, factor Xa, or thrombin between the marker sequence and the polypeptide, the marker sequence may be removed by the protease.

[4] Screening method of the present invention

The screening method of the present invention includes the screening method of a substance capable of activating the polypeptide for a screening tool of the present invention or the polypeptide of the present invention, and the screening method of an agent for improving the memory, an agent for improving learning ability, and/or an antidementia agent.

(1) Screening method of a substance capable of activating the polypeptide for a screening tool of the present invention or the polypeptide of the present invention The screening method of a substance capable of activating the polypeptide for a screening tool of the present invention or the polypeptide of the present invention is not particularly limited, so long as it comprises the steps of:

(i) bringing a substance to be tested into contact with the polypeptide for a screening tool of the present invention or the polypeptide of the present invention, or a cell expressing the polypeptide, (ii) analyzing (measuring or detecting) a channel activity, and (iii) selecting a substance capable of activating the channel.

The term "substance capable of activating the channel" as used herein means a substance which can activate the ion channel of interest by bringing the substance into contact with the ion channel. The "substance capable of activating the channel" includes a substance which can directly activate the channel, such as PS, and a substance which can promote activation of a substance capable of directly activating the channel.

A substance capable of promoting the activation of the above polypeptide by PS can be obtained by performing the above steps in the presence of PS. Such a screening method of a substance capable of promoting the activation of the above polypeptide by PS is included in the above screening method.

(2) Screening method of an agent for improving the memory, an agent for improving learning ability, and/or an antidementia agent PS exhibits activities of improving the memory, improving learning ability, and antidementia, and the mechanism is to activate the ion channel of the polypeptide for a screening tool. Therefore, an agent for improving the memory, an agent for improving learning ability, and/or an antidementia agent can be obtained by selecting a substance capable of activating the channel of the polypeptide for a screening tool (including a substance capable of promoting the activation of the above polypeptide by PS).

The screening method of an agent for improving the memory, an agent for improving learning ability, and/or an antidementia agent of the present invention is not particularly limited, so long as it comprises the steps of:

(i) bringing a substance to be tested into contact with the screening tool (preferably the cell-type screening tool) of an agent for improving the memory, an agent for improving learning ability, and/or an antidementia agent of the present invention, (ii) analyzing (measuring or detecting) a channel activity thereof, and (iii) selecting a substance capable of activating the channel.

A substance capable of enhancing the activation of the above polypeptide by PS can be obtained by performing the above steps in the presence of PS. Such a substance capable of enhancing the activation of the above polypeptide by PS can be obtained as an agent for improving the memory, an agent for improving learning ability, and/or an antidementia agent.

Further, the screening method of the present invention includes a screening method of a substance which binds to the polypeptide for a screening tool of the present invention, comprising the steps of:

(i) bringing a substance to be tested into contact with the polypeptide-type screening tool, (ii) analyzing the binding of the test substance to the polypeptide-type screening tool, and (iii) selecting a substance which binds to the polypeptide-type screening tool.

It may be confirmed whether or not the substance obtained by the screening method can be used as an agent for improving the memory, an agent for improving learning ability, and/or an antidementia agent, by a method known to those skilled in the art, or a modification thereof, such as a behavior test (using an animal, a measurement of LTP in the hippocampus using a brain slice, or a measurement of neurotransmission using a brain slice or neurons (Toshiya Manabe, Hisashi Mori, and Masahiro Katayama ed., Muteki no baio tekunikaru siriizu—Tokubetsu hen "Nou shinkei kenkyuu no susumekata", 1998, Youdo-sha). The measurement of neurotransmission using neurons can be carried out, for example, by the method described in Example 18.

As the screening method of the present invention (including the screening method of a substance capable of activating the polypeptide of the present invention, and the method of an agent for improving the memory, an agent for improving learning ability, and/or an antidementia agent), there may be mentioned, on the basis of differences in methods used for analyzing (measuring or detecting) the channel activity, for example, (a) a screening method utilizing a patch-clamp method, (b) a screening method utilizing an influx of a radioisotope ion, or (c) a screening method using a detection dye for intracellular $Ca^{2+}$.

Each screening method will be explained hereinafter.

According to the above screening method (a) utilizing a patch-clamp method, it can be analyzed whether or not a channel is activated, for example, by analyzing (preferably measuring) a whole-cell current in a cell utilizing a whole-cell patch-clamp method (Hille, B., "Ionic Channels of Excitable Membranes", 2nd Ed., 1992, Sinauer Associates Inc., MA).

More particularly, a cell expressing the polypeptide of the present invention, or the cell for a screening tool is voltage-clamped by a whole-cell voltage-clamp method, and a whole-cell current in the cell. In the measurement, a solution containing 149 mmol/L NaCl, 5 mmol/L KCl, 2 mmol/L $CaCl_2$, 0.8 mmol/L $MgCl_2$, and 10 mmol/L HEPES-Na (pH7.4) may be used as an extracellular solution, and a solution containing 147 mmol/L CsCl, 4.5 mmol/L EGTA, and 9 mmol/L HEPES-K (pH 7.2) may be used as an intracellular solution. Next, a change of the current is measured when a test substance is added to the extracellular solution or the intracellular solution, and as a result, a substance capable of activating the channel of the polypeptide of the present invention or the polypeptide for a screening tool can be obtained. For example, if a change of the whole-cell current generated by activation of the channel is increased when a test substance is added, it can be judged that the test substance is a substance capable of activating the channel. It is preferable that the screening method (a) is carried out under the conditions described in Example 4. As a substance capable of activating a channel, a substance showing a change of the cell current similar to that caused by PS, more particularly, a substance showing EC50 of 100 μmol/L or less under the conditions of Example 4, is preferably.

According to the above screening method (b) utilizing an influx of a radioisotope ion, the channel activity can be analyzed (preferably measured) by using each radioisotope corresponding to a $Ca^{2+}$ ion as an index [Sidney P. Colowick and Nathan O. Kaplan, "Methods in ENZYMOLOGY", 88(1), 1982, Academic Press, 346-347]. The method is based on a novel finding that the polypeptide of the present invention and the polypeptide for a screening tool is permeable to calcium ion (Examples 5 and 6).

It can be analyzed whether or not a channel of the polypeptide of the present invention or the polypeptide for a screening tool is activated, by bringing a test substance into contact with a cell expressing the polypeptide of the present invention, or the cell for a screening tool, and analyzing an amount of radioactivity permeated into the cell, or an amount of the remaining radioactivity outside of the cell.

More particularly, it can be measured using $^{45}Ca^{2+}$, a radioisotope of $Ca^{2+}$. When a test substance activates the channel in a reaction solution containing $^{45}Ca^{2+}$, the radioisotope flows into the cell. Therefore, the radioactivity contained in the extracellular solution (i.e., the remaining radioactivity in the extracellular solution), or the radioactivity permeated into the cell can be used as an index of the channel activation (Toshio Kuroki, Num-Ho Huh, Kazuhiro Chida ed., Jikken Igaku, Supplement "Bunshi seibutsugaku kenkyu no tame no baiyou saibou jikken hou", 1995, Youdo-sha). As a substance capable of activating a channel, a substance showing a $Ca^{2+}$ influx into a cell similar to that caused by PS, more particularly, a substance showing EC50 of 100 μmol/L or less, is preferably.

In the above screening method (c) using a detection dye for intracellular $Ca^{2+}$, for example, Fluo3-AM or the like may be used as the detection dye. According to the detection dye for intracellular $Ca^{2+}$, a change in the concentration of intracellular $Ca^{2+}$ accompanied by opening of the ion channel of the polypeptide of the present invention or the polypeptide for a screening tool can be analyzed (preferably measured) optically (Yoshihisa Kudo ed., Jikken Igaku, Supplement "Saibonai karushiumu jikken purotokoru", 1996, Youdo-sha). The channel activity can be measured by using the dye. When an amount of the detection dye for intracellular $Ca^{2+}$ in the presence of a test substance is changed in the channel-expressing cell, in comparison with that in the absence of the test substance, it can be judged that the test substance is a substance capable of activating the channel. The screening method (c) is not particularly limited, but it can be analyzed whether or not a test substance activates the channel, for example, by making a cell expressing the polypeptide of the present invention or the cell for a screening tool incorporate the detection dye for intracellular $Ca^{2+}$, and optically measuring a change in an amount of the detection dye in the cell by the test substance.

More particularly, if an amount of $Ca^{2+}$ permeated into the cell is increased when a test substance is added, in comparison with that in the absence of the test substance, it can be judged that the test substance is a substance capable of activating the channel. It is preferable that the screening method (c) is carried out under the conditions described in Example 6. As a substance capable of activating a channel, a substance showing a promotion of a change in an amount of the detection dye similar to that caused by PS, more particularly, a substance showing EC50 of 100 μmol/L or less under the conditions of Example 6, is preferably.

Further, the screening method (a), (b), or (c) can be also applied to a substance capable of indirectly (i.e., not directly) activating a channel. When a test substance is applied, and then PS is applied at a concentration insufficient for 100% activation of the channel (for example, 10 μmol/L of PS), it can be judged that a test substance showing a higher activity, in comparison with that in the absence of the test substance, promotes the channel activity.

A substance capable of promoting the activation of the polypeptide of the present invention by PS can be obtained by performing the screening in the presence of PS, as described above. As a substance capable of promoting the activation, a substance which can significantly promote the activity by PS, more particularly, a substance showing EC50 of 100 μmol/L or less, is preferable.

When the polypeptide of the present invention or the polypeptide for a screening exhibiting a cesium, sodium, or magnesium ion-permeable ion channel activity is used, a radioisotope of cesium, sodium, or magnesium can be used as an index, instead of $Ca^{2+}$ used in the screening method (b).

More particularly, it can be carried out in accordance with a method described in Sidney P. Colowick and Nathan O. Kaplan, "Methods in ENZYMOLOGY", 88(1), 1982, Academic Press, 346-347. This method is based on a novel finding that the polypeptide of the present invention and the polypeptide for a screening allow a cesium ion, a sodium ion, and a magnesium ion to permeate (Example 5).

Substances to be tested which may be applied to the screening method of the present invention are not particularly limited, but there may be mentioned, for example, various known compounds (including peptides) registered in chemical files, compounds obtained by combinatorial chemistry techniques (Terrett, N. K. et al., Tetrahedron, 51, 8135-8137, 1995), or random peptides prepared by employing a phage display method (Felici, F. et al., J. Mol. Biol., 222, 301-310, 1991). Further, natural components (such as culture supernatants or tissue extracts) derived from microorganisms, plants, marine organisms, or animals may be used. Furthermore, compounds (including peptides) obtained by chemically or biologically modifying compounds (including peptides) selected by the screening method of the present invention, such as N-[3-(2, 6-dichlorophenyl)-5-methylisoxazole-4-yl]-N'-ethyl-N-methyl-N'-phenylurea, 3-(2,6-difluorophenyl)-4-(piperidine-1-ylmethyl)-1,3-thiazole-2(3H)-thion, 3-(2,6-difluorophenyl)-4-(pyrrolidine-1-ylmethyl)-1,3-thiazole-2(3H)-thion, or N-(2-acetyl-3-thienyl)-2-[(2-chloro-6-fluorobenzyl)sulfanil]acetamide, may be used.

[5] Pharmaceutical composition of the present invention

The present invention includes the agent for improving the memory, an agent for improving learning ability, and/or an antidementia agent comprising as an active ingredient a substance (exclusive of PS) capable of activating the polypeptide for a screening tool of the present invention, and the process for manufacturing a pharmaceutical composition for improving the memory, improving learning ability, and/or antidementia, comprising the steps of:

(a) bringing a substance to be tested into contact with the screening tool of the present invention, (b) analyzing a channel activity thereof, and (c) preparing a medicament containing the substance. The present invention includes the method for preventing and/or treating a reduction in memory, a reduction in learning ability, and/or dementia, comprising administering to a subject in need thereof a substance capable of activating the polypeptide for a screening tool, and use of a substance capable of activating the polypeptide for a screening tool of the present invention, in the manufacture of a pharmaceutical composition for improving the memory, improving learning ability, and/or antidementia.

As the substance capable of activating the polypeptide for a screening tool of the present invention, there may be mentioned, for example, N-[3-(2,6-dichlorophenyl)-5-methyl-isoxazole-4-yl]-N'-ethyl-N-methyl-N'-phenylurea, 3-(2,6-difluorophenyl)-4-(piperidine-1-ylmethyl)-1,3-thiazole-2 (3H)-thion, 3-(2,6-difluorophenyl)-4-(pyrrolidine-1-ylmethyl)-1,3-thiazole-2(3H)-thion, or N-(2-acetyl-3-thienyl)-2-[(2-chloro-6-fluorobenzyl)sulfanil]acetamide.

The pharmaceutical composition comprising as an active ingredient a substance [for example, DNA, proteins (including antibodies or fragments thereof), peptides, or other compounds] capable of activating the polypeptide for a screening tool may be prepared using carriers, fillers, and/or other additives generally used in the preparation of medicaments, in accordance with the active ingredient.

Examples of administration include oral administration by tablets, pills, capsules, granules, fine granules, powders, oral solutions and the like, and parenteral administration by injections (e.g., intravenous, intramuscular, or the like), suppositories, transdermal preparations, transmucosal absorption preparations and the like. Particularly, in the case of peptides which are digested in the stomach, a parenteral administration such as an intravenous injection or the like is preferable.

In the solid composition for use in the oral administration, one or more active substances may be mixed with at least one inert diluent such as lactose, mannitol, glucose, microcrystalline cellulose, hydroxypropylcellulose, starch, polyvinyl pyrrolidone, or aluminum magnesium silicate. In the usual way, the composition may contain additives other than the inert diluent, such as a lubricant, a disintegrating agent, a stabilizing agent, or a solubilizing or solubilization assisting agent. If necessary, tablets or pills may be coated with a sugar coating or a film of a gastric or enteric substance.

The liquid composition for oral administration may include, for example, emulsions, solutions, suspensions, syrups, and elixirs, and may contain a generally used inert diluent such as purified water or ethyl alcohol. The composition may contain additives other than the inert diluent, such as moistening agents, suspending agents, sweeteners, flavors, or antiseptics.

The injections for parenteral administration may include aseptic aqueous or non-aqueous solutions, suspensions, and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil), alcohols (e.g., ethanol), polysorbate 80 and the like. Such a composition may further contain a moistening agent, an emulsifying agent, a dispersing agent, a stabilizing agent, a solubilizing or solubilization assisting agent, an antiseptic or the like. These compositions may be sterilized, for example, by filtration through a bacteria retaining filter, blending of a germicide, or irradiation. Alternatively, they may be used by first making them into sterile solid compositions and dissolving them in sterile water or other sterile solvent for injection use prior to their use.

The dose is optionally decided by taking into consideration the strength of each active ingredient, or symptoms, age, sex, or the like of each patient to be administered.

For example, in the case of oral administration, the usual dosage for an adult (60 kg in weight) is about 0.1 to 100 mg, preferably 0.1 to 50 mg per day. In the case of parenteral administration, the usual dosage is about 0.01 to 50 mg, preferably 0.01 to 10 mg per day in the form of an injection.

EXAMPLES

The present invention now will be further illustrated by, but is by no means limited to, the following Examples.

Example 1

Isolation of Human-derived Polynucleotide and Construction of Expression Vector

After 10 ng of human brain mRNA (Clontech) was treated with DNase, a reverse transcription was carried out using a kit for a reverse transcriptase-polymerase chain reaction (RT-PCR) (SUPERSCRIPT First-Strand Synthesis System for RT-PCR; Invitrogen) to synthesize the first strand cDNA. The resulting first strand cDNA, as a template, and Taq DNA polymerase (LA Taq DNA polymerase; Takara Shuzo) were used to perform a PCR by a hot start method. In the PCR, oligonucleotides consisting of the nucleotides of SEQ ID NOS: 7 and 8 were used as sense and antisense primers, respectively. A thermal denature at 98° C. for 1 minute was carried out, and a cycle composed of reactions at 98° C. for 15 seconds, at 59° C. for 30 seconds, and at 72° C. for 5 minutes was repeated 35 times. As a result, a DNA fragment of approximately 5.1 kbp was amplified.

A cloning kit (TOPO XL PCR Cloning Kit; Invitrogen) was used to clone the amplified DNA fragment into a pCR-TOPO vector. The resulting plasmid DNA was digested with restriction enzymes BamHI and NotI, and cloned into plasmid pcDNA3.1(+) (Invitrogen). The resulting clone was named pcDNA3.1-MLSN2. The plasmid pcDNA3.1(+) has a cytomegalovirus promoter sequence and may be used to express a protein in animal cells.

The nucleotide sequence of the resulting clone pcDNA3.1-MLSN2 was determined by a dideoxytermination method using a DNA sequencer (ABI3700 DNA Sequencer; Applied Biosystems) to obtain the nucleotide sequence of SEQ ID NO: 1.

The nucleotide sequence of SEQ ID NO: 1 contains an open reading frame of 4665 bp, i.e., a sequence consisting of nucleotides 50-4714 of SEQ ID NO: 1. The amino acid sequence of SEQ ID NO: 2 is an amino acid sequence (1554 amino acid residues) deduced from the open reading frame.

Example 2

Analysis of Expression in Human Brain

Expression of the gene obtained in Example 1 in a human brain, particularly the human hippocampus, was analyzed by a real time PCR using a sequence detector (PRISM7900; Applied Biosystems). The gene of interest contained in mRNA can be quantified by the real time PCR.

After 1 ng of each human mRNA (Clontech) derived from the whole brain or hippocampus was treated with DNase, the first strand DNA was obtained in accordance with the procedure described in Example 1. The resulting first strand DNA, as a template, and a fluorescent reagent (SYBR Green PCR Core Reagents Kit; Applied Biosystems) were used to perform a PCR. In the PCR, oligonucleotides consisting of the nucleotides of SEQ ID NOS: 9 and 10 were used as sense and antisense primers, respectively. A thermal denature at 95° C. for 10 minutes was carried out, and a cycle composed of reactions at 95° C. for 15 seconds and at 59° C. for 1 minute was repeated 45 times. Each sequence of the primers was specific for the gene consisting of the nucleotide sequence of SEQ ID NO: 1.

As a result, a gene fragment was amplified in both samples derived from the whole brain and the hippocampus. From the result, it was found that mRNA consisting of the nucleotide sequence of SEQ ID NO: 1 is expressed in the brain, particularly the hippocampus, and that the polypeptide consisting of the amino acid sequence of SEQ ID NO: 2 functions in the hippocampus associated with memory and learning.

Example 3

Expression of Protein in Animal cells

To detect a channel activity of the polypeptide consisting of the amino acid sequence of SEQ ID NO: 2, animal cells were transfected with the expression vector pcDNA3.1-MLSN2 obtained in Example 1 to express the polypeptide. The expression vector pcDNA3.1-MLSN2 obtained in Example 1 and reagents for transfection (LIPOFECTAMINE or LIPO- FECTAMINE2000; Invitrogen) were used to transform human embryonic kidney derived HEK293 cells (ATCC No.: CRL-1573) and induce the expression of the polypeptide consisting of the amino acid sequence of SEQ ID NO: 2. The cells transfected with LIPOFECTAMINE were used in Examples 4 and 5, and the cells transfected with LIPO-FECTAMINE2000 were used in Examples 6, 7, and 16.

The above procedures were carried out in accordance with protocols attached to the reagents for transfection, and known methods (Toshio Kuroki, Num-Ho Huh, Kazuhiro Chida ed., Jikken Igaku, Supplement "Bunshi seibutsugaku kenkyu no tame no baiyou saibou jikken hou", 1995, Youdo-sha).

Example 4

Electrophysiological Detection of Channel Activity

Each cell obtained in Example 3 was voltage-clamped by a whole-cell voltage-clamp method, and a whole-cell current generated when PS was applied was measured. A solution containing 149 mmol/L NaCl, 5 mmol/L KCl, 2 mmol/L $CaCl_2$, 0.8 mmol/L $MgCl_2$, and 10 mmol/L HEPES-Na (pH=7.4) was used as an extracellular solution, and a solution containing 147 mmol/L CsCl, 4.5 mmol/L EGTA, and 9 mmol/L HEPES-Cs(pH=7.2) was used as an intracellular solution.

When PS (100 µmol/L) was extracellularly applied to the cell transfected with plasmid pcDNA3.1-MLSN2 at a holding potential of −40 mV, an inward current (−5.8±0.9, n=10) was measured. After washing the cell, PS was applid thereto at a holding potential of +40 mV, a large outward current (108.9±19.3, n=10) was measured. A current-voltage relationship was measured using a voltage ramp during the response, an outward rectifier was observed. In contrast, PS was applied to a control cell transfected with no expression vector (i.e., a control cell not expressing the polypeptide of SEQ ID NO: 2) under the same conditions, but such currents were not observed.

It was found from the results that the polypeptide consisting of the amino acid sequence of SEQ ID NO: 2 is actiavetd by PS and functions as ion channel which allows ions inside or outside of a cell to pass through via the cell membrane.

Example 5

Examination of Ion Permeability

In accordance with the procedures described in Example 4, except for the extracellular solution, a $Ca^{2+}$ permeability in the channel activity of the polypeptide consisting of the amino acid sequence of SEQ ID NO: 2 by activation with PS was examined. Instead of the extracellular solution described in Example 4, a solution in which all the cations contained were $Ca^{2+}$ [117 mmol/L $CaCl_2$ and 5 mmol/L HEPES-Ca (pH=7.4); hereinafter referred to as $Ca^{2+}$ extracellular solution] was used. When PS (100 µmol/L) was applied under the conditions using the $Ca^{2+}$ extracellular solution, a larger inward current was measured, in comparison with that under the conditions using the extracellular solution described in Example 4 (i.e., general extracellular solution). A current-voltage relationship during the response was measured using a voltage ramp, an inward rectifier, which was different from the outward rectifier observed when using the general extracellular solution, was observed. While a reversal potential was +12.5 mV when using the general extracellular solution, the reversal potential observed in the $Ca^{2+}$ extracellular solution was shifted to the positive voltage side, +30.2 mV. A permeability coefficient ratio of $Ca^{2+}$ to $Cs^+$ was 4.1 on the basis of the obtained value. The ratio shows that the polypeptide consisting of the amino acid sequence of SEQ ID NO: 2 activated with PS exhibits a high $Ca^{2+}$ permeability.

Similarly, a $Mg^{2+}$ permeability in the channel activity of the polypeptide consisting of the amino acid sequence of SEQ ID NO: 2 by activation with PS was examined. When PS (100 µmol/L) was applid under conditions using an extracellular solution in which all the cations contained were $Mg^{2+}$ [117 mmol/L $MgCl_2$ and 5 mmol/L HEPES-Mg (pH=7.4)], a large inward current was measured, as the case using the $Ca^{2+}$ extracellular solution. The reversal potential was +27.5 mV, and the permeability coefficient ratio of $Mg^{2+}$ to $Cs^+$ was 3.4. It was found that the polypeptide consisting of the amino acid sequence of SEQ ID NO: 2 activated with PS exhibits a high $Mg^{2+}$ permeability.

In contrast, when the above extracellular solutions were replaced with a solution in which all the cations contained were NMDG+ (N-methyl-D-glucamine; non-permeable cation [155 mmol/L NMDG+ and 5 mmol/L HEPES-HCl (pH=7.4); hereinafter referred to as $NMDG^+$ extracellular solution] under the conditions in which the channel was activated with PS, the inward current was completely suppressed, and the outward current was increased approximately five-fold. Further, a current-voltage relationship observed in the $NMDG^+$ extracellular solution was shifted to the negative voltage side in comparison with the case using the general extracellular solution. The results show that $Cs^+$ is the major component of the currents, and it was found that the outward current component is $Cs^+$.

To examine an $Na^+$ permeability, when the above extracellular solutions were changed to a solution in which a concentration of $Na^+$ was lower than that in the general extracellular solution [31 mmol/L NaCl, 116 mmol/L $NMDG^+$, 5 mmol/L KCl, 2 mmol/L $CaCl_2$, 0.8 mmol/L $MgCl_2$, and 10 mmol/L HEPES (pH=7.4)] under the conditions in which the channel was activated with PS, the inward current was suppressed by approximately 50%. The result shows that the inward current component is $Na^+$.

From the above results, it was found that the polypeptide channel consisting of the amino acid sequence of SEQ ID NO: 2 activated with PS is permeable to $Na^+$, $Cs^+$, $Ca^{2+}$, and $Mg^{2+}$.

Example 6

Detection of Channel Activity Using Calcium-sensitive Fluorescent Reagent

The transformants ($4\times10^4$ cells) obtained in Example 3 were incubated at 37° C. for an hour in the presence of a calcium-sensitive fluorescent reagent (Fluo3-AM; DOJINDO), and the reagent was incorporated into the cells. The cells were washed with a physiological saline to remove the reagent not incorporated. A physiological saline supplemented with PS (final concentration=10 µmol/L) was added to the treated cells, and a time course of fluorescence emitted from the cells was measured using an automated fluorescence detector (FLIPR; Molecular Device). As controls, the same procedures were repeated, except that HEK293 cells transfected with pcDNA3.1(+) (i.e., control cells not expressing the polypeptide of SEQ ID NO: 2) were used, or except that a physiological saline without PS was used.

The results are shown in FIG. 1. When PS was added to the transformants, an increase in fluorescent intensity was detected immediately after the addition (measured value=approximately 10,000 counts). In contrast, no fluorescence was detected when using the control cells or the physiological saline without PS (measured value=approximately 0 count). The results show that the polypeptide consisting of the amino acid sequence of SEQ ID NO: 2 was activated with PS, and caused a calcium influx into cells.

From the above results, it was found that the polypeptide consisting of the amino acid sequence of SEQ ID NO: 2 is a novel human calcium-permeable nonselective cation channel protein, and causes a calcium influx into cells by activation with PS.

Example 7

PS-specificity in Ion Channel Activity

PS analogs were used to analyze whether of not the ion channel activity of the polypeptide consisting of the amino acid sequence of SEQ ID NO: 2 is activated with PS specifically.

Since PS is a steroid hormone, steroid hormones other than PS were used as PS analogs. Pregnenolone, dehydroepiandrosterone, progesterone, 17-hydroxyprogesterone, androstenedione, deoxycorticosterone, deoxycortisol, testosterone, corticosterone, cortisol, estradiol, 18-hydroxycorticosterone, and aldosterone were used as PS analogs to examine the calcium influx into cells caused by the polypeptide consisting of the amino acid sequence of SEQ ID NO: 2, in accordance with the method described in Example 6.

As a result, no PS analogs caused a remarkable calcium influx into cells, and it was found that the polypeptide consisting of the amino acid sequence of SEQ ID NO: 2 is PS-specifically activated.

Example 8

Isolation of Mouse Gene

A full-length of cDNA encoding a mouse polypeptide corresponding to the polypeptide consisting of the amino acid sequence of SEQ ID NO: 2 was obtained by carrying out an RT-PCR using mouse brain mRNA as a template. First 10 ng of mouse brain mRNA (Clontech) was used to synthesize the first strand cDNA, and then the PCR was carried out, as described in Example 1. In the PCR, oligonucleotides consisting of the nucleotides of SEQ ID NOS: 11 and 12 were used as sense and antisense primers, respectively. A thermal denature at 98° C. for 1 minute was carried out, and a cycle composed of reactions at 98° C. for 15 seconds, at 55° C. for 30 seconds, and at 72° C. for 6 minutes was repeated 35 times. As a result, a DNA fragment of approximately 5.2 kbp was amplified.

The obtained DNA fragment was cloned using a cloning kit (TOPO XL PCR Cloning Kit; Invitrogen) into a PCR-TOPO vector. The nucleotide sequence of the resulting clone was determined by a dideoxytermination method using a DNA sequencer (ABI3700 DNA Sequencer; Applied Biosystems) to obtain the nucleotide sequence of SEQ ID NO: 3.

The nucleotide sequence of SEQ ID NO: 3 contains an open reading frame of 4776 bp, i.e., a sequence consisting of nucleotides 218-4993 of SEQ ID NO: 3. The amino acid sequence of SEQ ID NO: 4 is an amino acid sequence (1591 amino acid residues) deduced from the open reading frame, and has a 97.1% homology with that of SEQ ID NO: 2. In this connection, the homology is a value obtained by a ClustalV method using MegAlign (DNASTAR).

Example 9

Analysis of Expression in Mouse Brain

Expression of the gene obtained in Example 8 in mouse brain was analyzed.

In accordance with the procedures described in Example 2, 1 ng of mouse brain mRNA (Clontech) was treated, except that oligonucleotides consisting of the nucleotides of SEQ ID NOS: 13 and 14 were used as sense and antisense primers, respectively. Each sequence of the primers was specific for the gene consisting of the nucleotide sequence of SEQ ID NO: 3.

As a result, a gene fragment was amplified in the sample derived from the brain. From the result, it was found that mRNA consisting of the nucleotide sequence of SEQ ID NO: 3 is expressed in the brain, and that the mouse polypeptide of SEQ ID NO: 4 functions in the brain.

Example 10

Isolation of Mouse Gene Fragment

To prepare a probe used in an in situ hybridization staining, a fragment of the mouse gene consisting of the nucleotide sequence of SEQ ID NO: 3 was isolated.

The fragment of the mouse gene consisting of the nucleotide sequence of SEQ ID NO: 3 was obtained by carrying out an RT-PCR using mouse brain mRNA as a template. In accordance with the procedures described in Example 1, 10 ng of mouse brain mRNA was treated, except that oligonucleotides consisting of the nucleotides of SEQ ID NOS: 15 and 16 were used as sense and antisense primers, respectively. As a result, a DNA fragment of approximately 0.5 kbp was amplified.

The resulting DNA fragment was cloned in accordance with the procedures described in Example 8, and the resulting clone was named pCR-TOPO-mouseMLSN2. The nucleotide sequence of pCR-TOPO-mouseMLSN2 was analyzed to confirm that it was the same sequence as that of nucleotides 3281-3768 of SEQ ID NO: 3 (mouse gene sequence).

Example 11

In situ Hybridization Staining of Gene in Fetal Mouse Brain

To determine an expression region in mouse brain of the gene obtained in Example 8, a fetal mouse brain was used to carry out an in situ hybridization staining.

A fetus in a pregnant mouse 17 days after fertilization was fixed with a 10% formalin neutral buffer solution while circulating. The fixed fetus was taken from the pregnant mouse, and embedded in paraffin to prepare a fetal mouse paraffin block. Sliced sections having a thickness of 6 μm were prepared from the paraffin block, as samples for the following in situ hybridization staining.

The plasmid pCR-TOPO-mouseMLSN2 obtained in Example 10 was used as a template to prepare an RNA antisense probe labeled with digoxigenin by an in vitro transcription method. In this connection, the digoxigenin labeling was performed using a commercially available reagent (DIG RNA Labeling Mix; Roche) in accordance with a protocol attached thereto. Further, a digoxigenin-labeled RNA sense probe was prepared as a negative control in a similar fashion.

The prepared samples and probes were used to carry out an in situ hybridization staining. As an antibody and a detecting substrate, anti-digoxigenin antibody labeled alkaline phosphatase (Roche) and NBT/BCI (a mixture of 5-bromo-4-chloro-3-indolyl-phosphoric acid and nitroblue tetrazolium salt) were used, respectively. After the development, nuclear staining was performed by kernechtrot.

As a result, when the antisense probe was used, the hippocampus was remarkably stained in the fetal mouse brain. In contrast, when the sense probe was used, such a stain was not observed. From the results, it was found that the gene consisting of the nucleotide sequence of SEQ ID NO: 3 is expressed in the hippocampus of the mouse brain.

Example 12

Isolation of Rat Gene

A full-length of cDNA encoding a rat polypeptide corresponding to the polypeptide consisting of the amino acid sequence of SEQ ID NO: 2 was obtained by carrying out an RT-PCR using rat brain mRNA as a template. First 10 ng of rat brain mRNA (Clontech) was used to synthesize the first strand cDNA, and then the PCR was carried out, as described in Example 1. In the PCR, oligonucleotides consisting of the nucleotides of SEQ ID NOS: 17 and 18 were used as sense and antisense primers, respectively. A thermal denature at 98° C. for 1 minute was carried out, and a cycle composed of reactions at 98° C. for 15 seconds, at 57.5° C. for 30 seconds, and at 72° C. for 6 minutes was repeated 35 times. As a result, a DNA fragment of approximately 5.1 kbp was amplified.

The obtained DNA fragment was cloned using a cloning kit (TOPO XL PCR Cloning Kit; Invitrogen) into a pCR-TOPO vector. The nucleotide sequence of the resulting clone was determined by a dideoxytermination method using a DNA sequencer (ABI3700 DNA Sequencer; Applied Biosystems) to obtain the nucleotide sequence of SEQ ID NO: 5.

The nucleotide sequence of SEQ ID NO: 5 contains an open reading frame of 4701 bp, i.e., a sequence consisting of nucleotides 182-4882 of SEQ ID NO: 5. The amino acid sequence of SEQ ID NO: 6 is an amino acid sequence (1566 amino acid residues) deduced from the open reading frame, and has a 97.9% homology with that of SEQ ID NO: 2 and a 98.9% homology with that of SEQ ID NO: 4. In this connection, the homology is a value obtained by a ClustalV method using MegAlign (DNASTAR).

Example 13

Preparation of Primary Cultured Neurons Derived from Rat Brain

A pregnant rat was anesthetized with diethyl ether, and the chest (heart) was dissected to sacrifice the rat by exsanguination. An abdomen was opened, and the uterus was dissected. After a fetus was sterilized with rubbing alcohol in a clean bench, the whole brain was dissected and placed in a petri dish containing a culture medium for neurons (SUMILON; Sumitomo Bakelite). The cerebral cortex and the hippocampus were dissected with fine forceps under a stereomicroscope, and transferred to 50-mL tubes independently. Each tube was allowed to stand, to precipitate each tissue, and each supernatant was removed by suction. A solution for cell dissociation [phosphate buffered saline (PBS) supplemented with 1% papain, 150 U/mL DNase I, 0.02% L-cysteine, 0.02% bovine serum albumin (BSA), and 0.5% glucose] was added to each tube, incubated at 37° C. for 15 minutes, and centrifuged (1000 rpm, 4° C., 5 minutes). Each supernatant was removed by suction, and 10 mL of a serum-free medium was added to each tube. The whole in each tube was dispersed by pipetting several times, and cell debris was removed through a filter to obtain each cell suspension.

Example 14

Calcium Influx by PS in Primary Cultured Neurons Derived from Rat Brain

This example was carried out in accordance with known methods (Yoshihisa Kudo ed., Jikken Igaku, Supplement "Saibo-nai karushiumu jikken purotokoru", 1996, Youdo-sha), except for the following procedures.

A time course of fluorescence emitted from cells was measured in accordance with the method described in Example 6, except that the primary cultured neurons ($4\times10^4$ cells) derived from the rat brain (cerebral cortex), obtained in Example 13, were cultured for a week and used, and that the final concentration of PS was 10 μmol/L or 50 μmol/L. As a control, a physiological saline without PS was used.

Figure 2:
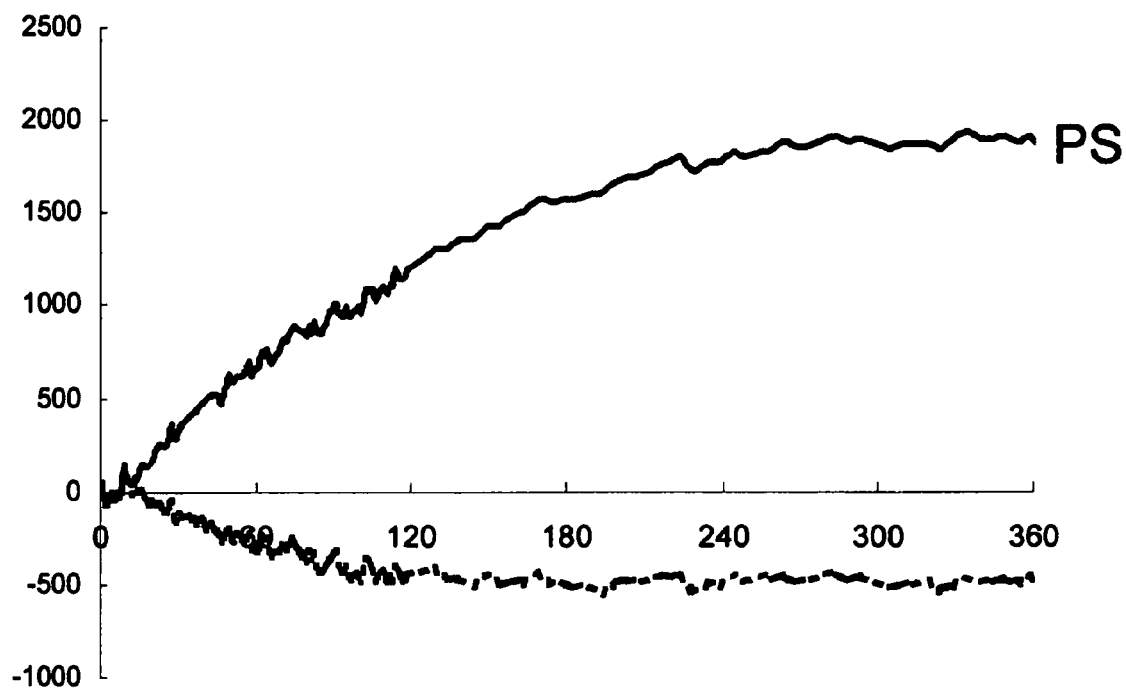
FIG. 2 is a graph showing the results of a calcium influx, as a time course of fluorescent intensity (unit=counts), when PS (10 μmol/L) was added to primary cultured neurons derived from rat cerebral cortex. The vertical axis indicates a change of fluorescent intensity by the calcium influx, and the horizontal axis indicates a time (seconds). The solid line indicates the result obtained by adding PS, and the dotted line indicates that obtained by adding a physiological saline.

As a result, when PS (10 μmol/L or 50 μmol/L) was added to the cells, an increase in fluorescent intensity was detected immediately after the addition, in both cases of 10 μmol/L and 50 μmol/L. In contrast, no fluorescence was detected in the control. The result (the final concentration of PS=10 μmol/L) is shown in FIG. 2. The result shows that the calcium-permeable ion channel located in the primary cultured neurons was activated with PS, and caused a calcium influx into cells.

Example 15

Analysis of Rat Gene Expression in Primary Cultured Neurons Derived from Rat Brain The expression of rat gene obtained in Example 12 in the primary cultured neurons derived from a rat brain (cerebral cortex and hippocampus) was analyzed by an RT-PCR method.

Each primary cultured neurons derived from the rat cerebral cortex or rat hippocampus, obtained in Example 13, and a reagent for RNA isolation (ISOGEN; TOYOBO) were used to obtain each total RNA, in accordance with a protocol attached thereto.

First 5 ng of each total RNA was used to synthesize the first strand cDNA, and then the PCR was carried out, as described in Example 1. In the PCR, oligonucleotides consisting of the nucleotides of SEQ ID NOS: 19 and 20 were used as sense and antisense primers, respectively. A thermal denature at 98° C. for 1 minute was carried out, and a cycle composed of reactions at 98° C. for 15 seconds, at 59° C. for 30 seconds, and at 72° C. for 1 minute was repeated 35 times. Each sequence of the primers was specific for the rat gene consisting of the nucleotide sequence of SEQ ID NO: 5.

As a result, a DNA fragment of approximately 0.5 kbp was amplified from each cDNA. From the result, it was found that the rat gene consisting of the nucleotide sequence of SEQ ID NO: 5 is expressed in the primary cultured neurons derived from the rat brain (cerebral cortex and hippocampus).

Example 16

Screening of Agent for Activating the Polypeptide of the Present Invention

A screening of compounds (activating agents) capable of activating the polypeptide consisting of the amino acid sequence of SEQ ID NO: 2 was carried out. As an index of activation, a calcium influx into cells was detected by using a calcium-sensitive fluorescent reagent, more particularly, in accordance to the method described in Example 6. With respect to a criterion for screening, a compound showing EC50 of 100 μmol/L or less was regarded as positive.

Various compounds were examined, and, as a compound showing an increase in fluorescent intensity, N-[3-(2,6-dichlorophenyl)-5-methylisoxazole-4-yl]-N'-ethyl-N-methyl-N'-phenylurea (code no. SPB 00071; MAYBRIDGE), 3-(2,6-difluorophenyl)-4-(piperidine-1-ylmethyl)-1,3-thiazole-2(3H)-thion (code no. MS 1368; MERLIN), 3-(2,6-difluorophenyl)-4-(pyrrolidine-1-ylmethyl)-1,3-thiazole-2 (3H)-thion (code no. MS 1370; MERLIN), and N-(2-acetyl-3-thienyl)-2-[(2-chloro-6-fluorobenzyl)sulfanil]acetamide (code no. GK 00678; Ryan Scientific) (hereinafter referred to as compounds A, B, C, and D, respectively) were found. With respect to the activation of the polypeptide consisting of the amino acid sequence of SEQ ID NO: 2 by each compound, EC50 values of compounds A, B, C, and D were 9.8 μmol/L, 6.8 μmol/L, 1.9 μmol/L, and 3.5 μmol/L, respectively. In contrast, when HEK cells not expressing the polypeptide of SEQ ID NO: 2 (i.e., negative control cells) were used in examining the above compounds, such an increase in fluorescent intensity was not detected.

From the results, it was found that the compounds A, B, C, and D can activate the polypeptide consisting of the amino acid sequence of SEQ ID NO: 2, and cause a calcium influx into cells.

Example 17

Effects of Agent for Activating the Polypeptide of the Present Invention in Primary Cultured Neurons Derived from Rat Cerebral Cortex Any one of compounds A, B, C, and D, and PS was applied to primary cultured neurons derived from the rat cerebral cortex obtained in Example 13, and a calcium influx into the neurons was measured. More particularly, the measurement was carried out in accordance with the method described in Example 14, except that the number of cells was $1 \times 10^5$ cells.

Figure 3:
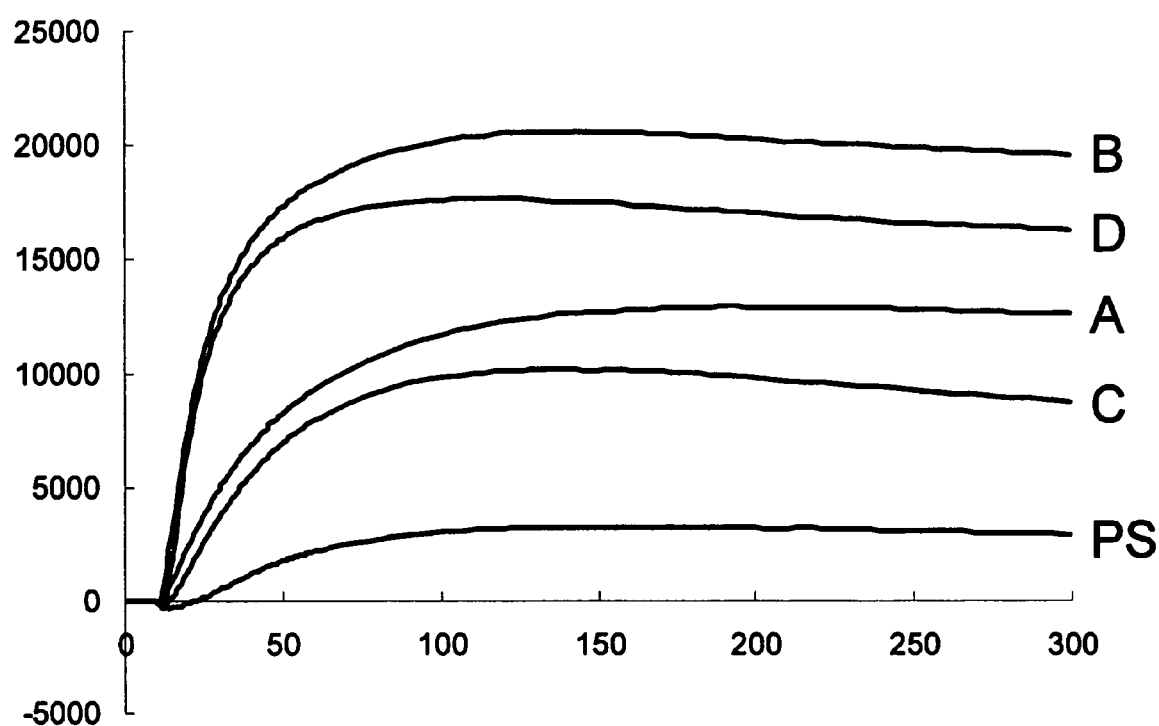
FIG. 3 is a graph showing the results of a calcium influx, as a time course of fluorescent intensity (unit=counts), when any one of compounds A, B, C, and D, and PS (10 μmol/L) was added to primary cultured neurons derived from rat cerebral cortex. The vertical axis indicates a change of fluorescent intensity by the calcium influx, and the horizontal axis indicates a time (seconds).

As a result, when any one of compounds A, B, C, and D, and PS (the final concentration=10 μmol/L) was applied to the cells, an increase in fluorescent intensity was detected immediately after the addition. The result of each compound is shown in FIG. 3.

From the results, it was found that compounds A, B, C, and D, and PS, which are activating agents for the polypeptide of the present invention, have an activity of causing a calcium influx into the neurons, and that the calcium influx into the neurons is caused via the activated polypeptide of the present invention. Further, it was confirmed that the calcium influx into the neurons in the presence of PS, shown in example 14, is caused by the activated polypeptide of the present invention.

Example 18

Effects of Agent for Activating the Polypeptide of the Present Invention in Primary Cultured Neurons Derived from Rat Hippocampus In this example, activities of improving the memory, improving learning ability, and/or antidementia in the present invention were shown by experimental results obtained in an experimental system using the neurons.

To confirm the effects of the activating agents on improving the memory, improving learning ability, and/or antidementia, any one of the compounds A, B, C, and D, which were found in Example 16 and can activate the polypeptide consisting of the amino acid sequence of SEQ ID NO: 2, was applied to the neurons to examine an activity of enhancing neurotransmission in the neurons. More particularly, effects of compounds A, B, C, and D on spontaneous excitatory postsynaptic currents (sEPSCs) in primary cultured neurons derived from the rat hippocampus, obtained in Example 13, were examined by a whole-cell patch-clamp method. The sEPSCs is a change of current generated in the neurons, when synaptic vesicles located at the terminus of another cell spontaneously exocytosis a neurotransmitter, and the former cell receives the released neurotransmitter. Therefore, neurotransmission between the neurons can be measured by measuring the sEPSCs (Journal of Neurophysiology, 76, 3159-3168, 1996; The Journal of Neuroscience, 19, 5311-5321, 1999). Further, it is known that the neurotransmission is suppressed by inhibiting the sEPSCs (Journal of Neuroscience Research, 72, 116-124, 2003).

More particularly, the cells (approximately $1 \times 10^5$ cells per dish) obtained in Example 13 were plated in a culture dish having a diameter of 35 mm, and cultured for 1 to 5 weeks. As a culture medium, a culture medium for the neurons (SUMILON; Sumitomo Bakelite) was used. Other procedures for cultivation were carried out in accordance with known methods (Methods in Neuroscience vol. 2, Cell culture, P. Michael Conn ed, Academic Press, Inc. 1990). The cell was voltage-clamped at −60 mV by a whole-cell voltage-clamp method, and a whole-cell current generated when PS or each compound was applied was measured (Yasunobu Okada ed., "Shin pacchi kuranpu jikken gijyutsu hou", Yoshioka shoten, 2001). A solution containing 140 mmol/L NaCl, 5.4 mmol/L KCl, 2 mmol/L $CaCl_2$, 0.8 mmol/L $MgCl_2$, 15 mmol/L glucose, 10 mmol/L HEPES-Na (pH=7.4), 20 μmol/L biculline, and 1 μmol/L strychnine was used as an extracellular solution. A solution containing 100 mmol/L potassium gluconate, 10 mmol/L EGTA, 5 mmol/L $MgCl_2$, 2 mmol/L $K_2ATP$, 0.3 mmol/L $Na_2GTP$, and 40 mmol/L HEPES-K (pH=7.25) was used as an intracellular solution.

As a result, when any one of compounds A, B, and C (the final concentration=10 μmol/L) and compound D (the final concentration=1 μmol/L) was applied to the neurons, the enhancement of sEPSCs was detected. In this connection, the effect of PS was examined as a positive control, and the enhancement of sEPSCs was similarly detected. The results of compounds A to D and PS are shown in FIG. 4.

From the results, it was found that compounds A, B, C, and D, activating agents for the polypeptide of the present invention, can facillitate neurotransmission in the neurons, and it was confirmed that the neurotransmission in the neurons is promoted via the activated polypeptide of the present invention.

INDUSTRIAL APPLICABILITY

According to the screening tool or the screening method of the present invention, a screening of a substance which is useful as an agent for improving the memory, an agent for improving learning ability, and/or an antidementia agent may be carried out. The polypeptide, the polynucleotide, the vector, and the cell of the present invention are useful in constructing the above screening system.

Although the present invention has been described with reference to specific embodiments, various changes and modifications obvious to those skilled in the art are possible without departing from the scope of the appended claims.

The invention claimed is:

1. A method of screening for a substance for improving memory, a substance for improving learning ability, and/or a substance for treating dementia, comprising the steps of:
   (a) in the presence of pregnenolone sulfate, bringing a test substance into contact with a screening tool, wherein said screening tool exhibits calcium ion-permeable ion channel activity upon activation with the pregnenolone sulfate and comprises at least one of:
       (1) a polypeptide consisting of the amino acid sequence of SEQ ID NO: 2, 4, or 6,
       (2) a polypeptide comprising the amino acid sequence of SEQ ID NO: 2, 4, or 6, and exhibiting calcium ion-permeable ion channel activity upon activation with pregnenolone sulfate,
       (3) a polypeptide consisting of the amino acid sequence having 98% or more homology with that of SEQ ID NO: 2, 4, or 6, and exhibiting calcium ion-permeable ion channel activity upon activation with pregnenolone sulfate, or
       (4) a cell expressing at least one of the polypeptides (1) to (3),
   (b) measuring the calcium ion-permeable ion channel activity of said screening tool following contact with the test substance,
   (c) comparing the pregnenolone sulfate-mediated activation of the calcium ion-permeable channel activity of the screening tool obtained in the presence of the test substance to the pregnenolone sulfate-mediated activation of the calcium ion-permeable channel activity of the screening tool obtained in the absence of the test substance, and
   (d) selecting a test substance that enhances the pregnenolone sulfate-mediated calcium ion-permeable ion channel activity of the screening tool and thereby identifying a substance for improving memory, a substance for improving learning ability, and/or a substance for treating dementia.

2. The method of claim 1, wherein the polypeptide in section (a)(3) is a polypeptide consisting of the amino acid sequence having 99% or more homology with that of SEQ ID NO: 2, 4, or 6, and exhibiting calcium ion-permeable ion channel activity upon activation with pregnenolone sulfate.

* * * * *

SEQUENCE LISTING

<160> NUMBER OF SEQ ID NOS: 20

<210> SEQ ID NO 1
<211> LENGTH: 5112
<212> TYPE: DNA
<213> ORGANISM: Homo sapiens
<220> FEATURE:
<221> NAME/KEY: CDS
<222> LOCATION: (50)..(4714)
<223> OTHER INFORMATION:
<220> FEATURE:
<223> OTHER INFORMATION: Inventor: Sano, Yorikata; Inamura, Kohei;
      Mochizuki Shinobu

<400> SEQUENCE: 1

```
tgcttttggg accattgagt tccaaggagg tggccattcc aacaaagcc atg tat gtg        58
                                                    Met Tyr Val
                                                      1 cga gta tct ttt gat aca aaa cct gat ctc ctc tta cac ctg atg acc         106
Arg Val Ser Phe Asp Thr Lys Pro Asp Leu Leu Leu His Leu Met Thr
      5                  10                  15 aag gaa tgg cag ttg gag ctt ccc aag ctt ctc atc tct gtc cat ggg         154
Lys Glu Trp Gln Leu Glu Leu Pro Lys Leu Leu Ile Ser Val His Gly
 20                  25                  30                  35 ggc ctg cag aac ttt gaa ctc cag cca aaa ctc aag caa gtc ttt ggg         202
Gly Leu Gln Asn Phe Glu Leu Gln Pro Lys Leu Lys Gln Val Phe Gly
              40                  45                  50 aaa ggg ctc atc aaa gca gca atg aca act gga gcg tgg ata ttc act         250
Lys Gly Leu Ile Lys Ala Ala Met Thr Thr Gly Ala Trp Ile Phe Thr
          55                  60                  65 gga ggg gtt aac aca ggt gtt att cgt cat gtt ggc gat gcc ttg aag         298
Gly Gly Val Asn Thr Gly Val Ile Arg His Val Gly Asp Ala Leu Lys
      70                  75                  80 gat cat gcc tct aag tct cga gga aag ata tgc acc ata ggt att gcc         346
Asp His Ala Ser Lys Ser Arg Gly Lys Ile Cys Thr Ile Gly Ile Ala
 85                  90                  95 ccc tgg gga att gtg gaa aac cag gag gac ctc att gga aga gat gtt         394
Pro Trp Gly Ile Val Glu Asn Gln Glu Asp Leu Ile Gly Arg Asp Val
100                 105                 110                 115 gtc cgg cca tac cag acc atg tcc aat ccc atg agc aag ctc act gtt         442
Val Arg Pro Tyr Gln Thr Met Ser Asn Pro Met Ser Lys Leu Thr Val
              120                 125                 130 ctc aac agc atg cat tcc cac ttc att ctg gct gac aac ggg acc act         490
Leu Asn Ser Met His Ser His Phe Ile Leu Ala Asp Asn Gly Thr Thr
          135                 140                 145 gga aaa tat gga gca gag gtg aaa ctt cga aga caa ctg gaa aag cat         538
Gly Lys Tyr Gly Ala Glu Val Lys Leu Arg Arg Gln Leu Glu Lys His
      150                 155                 160 att tca ctc cag aag ata aac aca aga atc ggt caa ggt gtt cct gtg         586
Ile Ser Leu Gln Lys Ile Asn Thr Arg Ile Gly Gln Gly Val Pro Val
 165                 170                 175 gtg gca ctc ata gtg gaa gga gga ccc aat gtg atc tcg att gtt ttg         634
Val Ala Leu Ile Val Glu Gly Gly Pro Asn Val Ile Ser Ile Val Leu
180                 185                 190                 195 gag tac ctt cga gac acc cct ccc gtg cca gtg gtt gtc tgt gat ggg         682
Glu Tyr Leu Arg Asp Thr Pro Pro Val Pro Val Val Val Cys Asp Gly
              200                 205                 210 agt gga cgg gca tcg gac atc ctg gcc ttt ggg cat aaa tac tca gaa         730
Ser Gly Arg Ala Ser Asp Ile Leu Ala Phe Gly His Lys Tyr Ser Glu
          215                 220                 225
```

```
gaa ggc gga ctg ata aat gaa tct ttg agg gac cag ctg ttg gtg act      778
Glu Gly Gly Leu Ile Asn Glu Ser Leu Arg Asp Gln Leu Leu Val Thr
            230                 235                 240 ata cag aag act ttc aca tac act cga acc caa gct cag cat ctg ttc      826
Ile Gln Lys Thr Phe Thr Tyr Thr Arg Thr Gln Ala Gln His Leu Phe
245                 250                 255 atc atc ctc atg gag tgc atg aag aag aag gaa ttg att acg gta ttt      874
Ile Ile Leu Met Glu Cys Met Lys Lys Lys Glu Leu Ile Thr Val Phe
260                 265                 270                 275 cgg atg gga tca gaa gga cac cag gac att gat ttg gct atc ctg aca      922
Arg Met Gly Ser Glu Gly His Gln Asp Ile Asp Leu Ala Ile Leu Thr
            280                 285                 290 gct tta ctc aaa gga gcc aat gcc tcg gcc cca gac caa ctg agc tta      970
Ala Leu Leu Lys Gly Ala Asn Ala Ser Ala Pro Asp Gln Leu Ser Leu
                295                 300                 305 gct tta gcc tgg aac aga gtc gac atc gct cgc agc cag atc ttt att     1018
Ala Leu Ala Trp Asn Arg Val Asp Ile Ala Arg Ser Gln Ile Phe Ile
            310                 315                 320 tac ggg caa cag tgg ccg gtg gga tct ctg gag caa gcc atg ttg gat     1066
Tyr Gly Gln Gln Trp Pro Val Gly Ser Leu Glu Gln Ala Met Leu Asp
325                 330                 335 gcc tta gtt ctg gac aga gtg gat ttt gtg aaa tta ctc ata gag aat     1114
Ala Leu Val Leu Asp Arg Val Asp Phe Val Lys Leu Leu Ile Glu Asn
340                 345                 350                 355 gga gta agc atg cac cgt ttt ctc acc atc tcc aga cta gag gaa ttg     1162
Gly Val Ser Met His Arg Phe Leu Thr Ile Ser Arg Leu Glu Glu Leu
            360                 365                 370 tac aat acg aga cat ggg ccc tca aat aca ttg tac cac ttg gtc agg     1210
Tyr Asn Thr Arg His Gly Pro Ser Asn Thr Leu Tyr His Leu Val Arg
                375                 380                 385 gat gtc aaa aag ggg aac ctg ccc cca gac tac aga atc agc ctg att     1258
Asp Val Lys Lys Gly Asn Leu Pro Pro Asp Tyr Arg Ile Ser Leu Ile
            390                 395                 400 gac atc ggc ctg gtg atc gag tac ctg atg ggc ggg gct tat cgc tgc     1306
Asp Ile Gly Leu Val Ile Glu Tyr Leu Met Gly Gly Ala Tyr Arg Cys
405                 410                 415 aac tac acg cgc aag cgc ttc cgg acc ctc tac cac aac ctc ttc ggc     1354
Asn Tyr Thr Arg Lys Arg Phe Arg Thr Leu Tyr His Asn Leu Phe Gly
420                 425                 430                 435 ccc aag agg ccc aaa gcc ttg aaa ctg ctg gga atg gag gat gat att     1402
Pro Lys Arg Pro Lys Ala Leu Lys Leu Leu Gly Met Glu Asp Asp Ile
            440                 445                 450 ccc ttg agg cga gga aga aag aca acc aag aaa cgt gaa gaa gag gtg     1450
Pro Leu Arg Arg Gly Arg Lys Thr Thr Lys Lys Arg Glu Glu Glu Val
                455                 460                 465 gac att gac ttg gat gat cct gag atc aac cac ttc ccc ttc cct ttc     1498
Asp Ile Asp Leu Asp Asp Pro Glu Ile Asn His Phe Pro Phe Pro Phe
            470                 475                 480 cat gag ctc atg gtg tgg gct gtt ctc atg aag cgg cag aag atg gcc     1546
His Glu Leu Met Val Trp Ala Val Leu Met Lys Arg Gln Lys Met Ala
485                 490                 495 ctg ttc ttc tgg cag cac ggt gag gag gcc atg gcc aag gcc ctg gtg     1594
Leu Phe Phe Trp Gln His Gly Glu Glu Ala Met Ala Lys Ala Leu Val
500                 505                 510                 515 gcc tgc aag ctc tgc aaa gcc atg gct cat gag gcc tct gag aac gac     1642
Ala Cys Lys Leu Cys Lys Ala Met Ala His Glu Ala Ser Glu Asn Asp
            520                 525                 530 atg gtt gac gac att tcc cag gag ctg aat cac aat tcc aga gac ttt     1690
Met Val Asp Asp Ile Ser Gln Glu Leu Asn His Asn Ser Arg Asp Phe
                535                 540                 545
```

```
ggc cag ctg gct gtg gag ctc ctg gac cag tcc tac aag cag gac gaa    1738
Gly Gln Leu Ala Val Glu Leu Leu Asp Gln Ser Tyr Lys Gln Asp Glu
            550                 555                 560 cag ctg gcc atg aaa ctg ctg acg tat gag ctg aag aac tgg agc aac    1786
Gln Leu Ala Met Lys Leu Leu Thr Tyr Glu Leu Lys Asn Trp Ser Asn
565                 570                 575 gcc acg tgc ctg cag ctt gcc gtg gct gcc aaa cac cgc gac ttc atc    1834
Ala Thr Cys Leu Gln Leu Ala Val Ala Ala Lys His Arg Asp Phe Ile
580                 585                 590                 595 gcg cac acg tgc agc cag atg ctg ctc acc gac atg tgg atg ggc cgg    1882
Ala His Thr Cys Ser Gln Met Leu Leu Thr Asp Met Trp Met Gly Arg
            600                 605                 610 ctc cgc atg cgc aag aac tca ggc ctc aag gta att ctg gga att cta    1930
Leu Arg Met Arg Lys Asn Ser Gly Leu Lys Val Ile Leu Gly Ile Leu
            615                 620                 625 ctt cct cct tca att ctc agc ttg gag ttc aag aac aaa gac gac atg    1978
Leu Pro Pro Ser Ile Leu Ser Leu Glu Phe Lys Asn Lys Asp Asp Met
            630                 635                 640 ccc tat atg tct cag gcc cag gaa atc cac ctc caa gag aag gag gca    2026
Pro Tyr Met Ser Gln Ala Gln Glu Ile His Leu Gln Glu Lys Glu Ala
645                 650                 655 gaa gaa cca gag aag ccc aca aag gaa aaa gag gaa gag gac atg gag    2074
Glu Glu Pro Glu Lys Pro Thr Lys Glu Lys Glu Glu Glu Asp Met Glu
660                 665                 670                 675 ctc aca gca atg ttg gga cga aac aac ggg gag tcc tcc agg aag aag    2122
Leu Thr Ala Met Leu Gly Arg Asn Asn Gly Glu Ser Ser Arg Lys Lys
            680                 685                 690 gat gaa gag gaa gtt cag agc aag cac cgg tta atc ccc ctc ggc aga    2170
Asp Glu Glu Glu Val Gln Ser Lys His Arg Leu Ile Pro Leu Gly Arg
            695                 700                 705 aaa atc tat gaa ttc tac aat gca ccc atc gtg aag ttc tgg ttc tac    2218
Lys Ile Tyr Glu Phe Tyr Asn Ala Pro Ile Val Lys Phe Trp Phe Tyr
            710                 715                 720 aca ctg gcg tat atc gga tac ctg atg ctc ttc aac tat atc gtg tta    2266
Thr Leu Ala Tyr Ile Gly Tyr Leu Met Leu Phe Asn Tyr Ile Val Leu
725                 730                 735 gtg aag atg gaa cgc tgg ccg tcc acc cag gaa tgg atc gta atc tcc    2314
Val Lys Met Glu Arg Trp Pro Ser Thr Gln Glu Trp Ile Val Ile Ser
740                 745                 750                 755 tat att ttc acc ctg gga ata gaa aag atg aga gag att ctg atg tca    2362
Tyr Ile Phe Thr Leu Gly Ile Glu Lys Met Arg Glu Ile Leu Met Ser
            760                 765                 770 gag cca ggg aag ttg cta cag aaa gtg aag gta tgg ctg cag gag tac    2410
Glu Pro Gly Lys Leu Leu Gln Lys Val Lys Val Trp Leu Gln Glu Tyr
            775                 780                 785 tgg aat gtc acg gac ctc atc gcc atc ctt ctg ttt tct gtc gga atg    2458
Trp Asn Val Thr Asp Leu Ile Ala Ile Leu Leu Phe Ser Val Gly Met
            790                 795                 800 atc ctt cgt ctc caa gac cag ccc ttc agg agt gac ggg agg gtc atc    2506
Ile Leu Arg Leu Gln Asp Gln Pro Phe Arg Ser Asp Gly Arg Val Ile
805                 810                 815 tac tgc gtg aac atc att tac tgg tat atc cgt ctc cta gac atc ttc    2554
Tyr Cys Val Asn Ile Ile Tyr Trp Tyr Ile Arg Leu Leu Asp Ile Phe
820                 825                 830                 835 ggc gtg aac aag tat ttg ggc ccg tat gta atg atg att gga aaa atg    2602
Gly Val Asn Lys Tyr Leu Gly Pro Tyr Val Met Met Ile Gly Lys Met
            840                 845                 850 atg ata gac atg atg tac ttt gtc atc att atg ctg gtg gtt ctg atg    2650
Met Ile Asp Met Met Tyr Phe Val Ile Ile Met Leu Val Val Leu Met
```

-continued

```
                855                 860                 865
agc ttt ggg gtc gcc agg caa gcc atc ctt ttt ccc aat gag gag cca      2698
Ser Phe Gly Val Ala Arg Gln Ala Ile Leu Phe Pro Asn Glu Glu Pro
        870                 875                 880 tca tgg aaa ctg gcc aag aac atc ttc tac atg ccc tat tgg atg att      2746
Ser Trp Lys Leu Ala Lys Asn Ile Phe Tyr Met Pro Tyr Trp Met Ile
885                 890                 895 tat ggg gaa gtg ttt gcg gac cag ata gac cct ccc tgt gga cag aat      2794
Tyr Gly Glu Val Phe Ala Asp Gln Ile Asp Pro Pro Cys Gly Gln Asn
900                 905                 910                 915 gag acc cga gag gat ggt aaa ata atc cag ctg cct ccc tgc aag aca      2842
Glu Thr Arg Glu Asp Gly Lys Ile Ile Gln Leu Pro Pro Cys Lys Thr
        920                 925                 930 gga gct tgg atc gtg ccg gcc atc atg gcc tgc tac ctc tta gtg gca      2890
Gly Ala Trp Ile Val Pro Ala Ile Met Ala Cys Tyr Leu Leu Val Ala
            935                 940                 945 aac atc ttg ctg gtc aac ctc ctc att gct gtc ttt aac aat aca ttt      2938
Asn Ile Leu Leu Val Asn Leu Leu Ile Ala Val Phe Asn Asn Thr Phe
        950                 955                 960 ttt gaa gta aaa tcg ata tcc aac caa gtc tgg aag ttt cag agg tat      2986
Phe Glu Val Lys Ser Ile Ser Asn Gln Val Trp Lys Phe Gln Arg Tyr
965                 970                 975 cag ctc atc atg act ttc cat gaa agg cca gtt ctg ccc cca cca ctg      3034
Gln Leu Ile Met Thr Phe His Glu Arg Pro Val Leu Pro Pro Pro Leu
980                 985                 990                 995 atc atc ttc agc cac  atg acc atg ata ttc  cag cac ctg tgc tgc        3079
Ile Ile Phe Ser His  Met Thr Met Ile Phe  Gln His Leu Cys Cys
                1000                 1005                 1010 cga tgg agg aaa cac  gag agc gac ccg gat  gaa agg gac tac ggc        3124
Arg Trp Arg Lys His  Glu Ser Asp Pro Asp  Glu Arg Asp Tyr Gly
                1015                 1020                 1025 ctg aaa ctc ttc ata  acc gat gat gag ctc  aag aaa gta cat gac        3169
Leu Lys Leu Phe Ile  Thr Asp Asp Glu Leu  Lys Lys Val His Asp
                1030                 1035                 1040 ttt gaa gag caa tgc  ata gaa gaa tac ttc  aga gaa aag gat gat        3214
Phe Glu Glu Gln Cys  Ile Glu Glu Tyr Phe  Arg Glu Lys Asp Asp
                1045                 1050                 1055 cgg ttc aac tca tct  aat gat gag agg ata  cgg gtg act tca gaa        3259
Arg Phe Asn Ser Ser  Asn Asp Glu Arg Ile  Arg Val Thr Ser Glu
                1060                 1065                 1070 agg gtg gag aac atg  tct atg cgg ctg gag  gaa gtc aac gag aga        3304
Arg Val Glu Asn Met  Ser Met Arg Leu Glu  Glu Val Asn Glu Arg
                1075                 1080                 1085 gag cac tcc atg aag  gct tca ctc cag acc  gtg gac atc cgg ctg        3349
Glu His Ser Met Lys  Ala Ser Leu Gln Thr  Val Asp Ile Arg Leu
                1090                 1095                 1100 gcg cag ctg gaa gac  ctt atc ggg cgc atg  gcc acg gcc ctg gag        3394
Ala Gln Leu Glu Asp  Leu Ile Gly Arg Met  Ala Thr Ala Leu Glu
                1105                 1110                 1115 cgc ctg aca ggt ctg  gag cgg gcc gag tcc  aac aaa atc cgc tcg        3439
Arg Leu Thr Gly Leu  Glu Arg Ala Glu Ser  Asn Lys Ile Arg Ser
                1120                 1125                 1130 agg acc tcg tca gac  tgc acg gac gcc gcc  tac att gtc cgt cag        3484
Arg Thr Ser Ser Asp  Cys Thr Asp Ala Ala  Tyr Ile Val Arg Gln
                1135                 1140                 1145 agc agc ttc aac agc  cag gaa ggg aac acc  ttc aag ctc caa gag        3529
Ser Ser Phe Asn Ser  Gln Glu Gly Asn Thr  Phe Lys Leu Gln Glu
                1150                 1155                 1160 agt ata gac cct gca  ggt gag gag acc atg  tcc cca act tct cca        3574
```

-continued

| | | | | | | | | | | | | |
|---|---|---|---|---|---|---|---|---|---|---|---|---|
| Ser | Ile | Asp | Pro | Ala | Gly | Glu | Glu | Thr | Met | Ser | Pro | Thr | Ser | Pro |
| | | | 1165 | | | | 1170 | | | | 1175 | |

```
acc  tta  atg  ccc  cgt  atg  cga  agc  cat  tct  ttc  tat  tcg  gtc  aat              3619
Thr  Leu  Met  Pro  Arg  Met  Arg  Ser  His  Ser  Phe  Tyr  Ser  Val  Asn
               1180                    1185                         1190 atg  aaa  gac  aaa  ggt  ggt  ata  gaa  aag  ttg  gaa  agt  att  ttt  aaa              3664
Met  Lys  Asp  Lys  Gly  Gly  Ile  Glu  Lys  Leu  Glu  Ser  Ile  Phe  Lys
               1195                    1200                         1205 gaa  agg  tcc  ctg  agc  cta  cac  cgg  gct  act  agt  tcc  cac  tct  gta              3709
Glu  Arg  Ser  Leu  Ser  Leu  His  Arg  Ala  Thr  Ser  Ser  His  Ser  Val
               1210                    1215                         1220 gca  aaa  gaa  ccc  aaa  gct  cct  gca  gcc  cct  gcc  aac  acc  ttg  gcc              3754
Ala  Lys  Glu  Pro  Lys  Ala  Pro  Ala  Ala  Pro  Ala  Asn  Thr  Leu  Ala
               1225                    1230                         1235 att  gtt  cct  gat  tcc  aga  aga  cca  tca  tcg  tgt  ata  gac  atc  tat              3799
Ile  Val  Pro  Asp  Ser  Arg  Arg  Pro  Ser  Ser  Cys  Ile  Asp  Ile  Tyr
               1240                    1245                         1250 gtc  tct  gct  atg  gat  gag  ctc  cac  tgt  gat  ata  gac  cct  ctg  gac              3844
Val  Ser  Ala  Met  Asp  Glu  Leu  His  Cys  Asp  Ile  Asp  Pro  Leu  Asp
               1255                    1260                         1265 aat  tcc  gtg  aac  atc  ctt  ggg  cta  ggc  gag  cca  agc  ttt  tca  act              3889
Asn  Ser  Val  Asn  Ile  Leu  Gly  Leu  Gly  Glu  Pro  Ser  Phe  Ser  Thr
               1270                    1275                         1280 cca  gta  cct  tcc  aca  gcc  cct  tca  agt  agt  gcc  tat  gca  aca  ctt              3934
Pro  Val  Pro  Ser  Thr  Ala  Pro  Ser  Ser  Ser  Ala  Tyr  Ala  Thr  Leu
               1285                    1290                         1295 gca  ccc  aca  gac  aga  cct  cca  agc  cgg  agc  att  gat  ttt  gag  gac              3979
Ala  Pro  Thr  Asp  Arg  Pro  Pro  Ser  Arg  Ser  Ile  Asp  Phe  Glu  Asp
               1300                    1305                         1310 atc  acc  tcc  atg  gac  act  aga  tct  ttt  tct  tca  gac  tac  acc  cac              4024
Ile  Thr  Ser  Met  Asp  Thr  Arg  Ser  Phe  Ser  Ser  Asp  Tyr  Thr  His
               1315                    1320                         1325 ctc  cca  gaa  tgc  caa  aac  ccc  tgg  gac  tca  gag  cct  ccg  atg  tac              4069
Leu  Pro  Glu  Cys  Gln  Asn  Pro  Trp  Asp  Ser  Glu  Pro  Pro  Met  Tyr
               1330                    1335                         1340 cac  acc  att  gag  cgt  tcc  aaa  agt  agc  cgc  tac  cta  gcc  acc  aca              4114
His  Thr  Ile  Glu  Arg  Ser  Lys  Ser  Ser  Arg  Tyr  Leu  Ala  Thr  Thr
               1345                    1350                         1355 ccc  ttt  ctt  cta  gaa  gag  gct  ccc  att  gtg  aaa  tct  cat  agc  ttt              4159
Pro  Phe  Leu  Leu  Glu  Glu  Ala  Pro  Ile  Val  Lys  Ser  His  Ser  Phe
               1360                    1365                         1370 atg  ttt  tcc  ccc  tca  agg  agc  tat  tat  gcc  aac  ttt  ggg  gtg  cct              4204
Met  Phe  Ser  Pro  Ser  Arg  Ser  Tyr  Tyr  Ala  Asn  Phe  Gly  Val  Pro
               1375                    1380                         1385 gta  aaa  aca  gca  gaa  tac  aca  agt  att  aca  gac  tgt  att  gac  aca              4249
Val  Lys  Thr  Ala  Glu  Tyr  Thr  Ser  Ile  Thr  Asp  Cys  Ile  Asp  Thr
               1390                    1395                         1400 agg  tgt  gtc  aat  gcc  cct  caa  gca  att  gcg  gac  aga  gct  gcc  ttc              4294
Arg  Cys  Val  Asn  Ala  Pro  Gln  Ala  Ile  Ala  Asp  Arg  Ala  Ala  Phe
               1405                    1410                         1415 cct  gga  ggt  ctt  gga  gac  aaa  gtg  gag  gac  tta  act  tgc  tgc  cat              4339
Pro  Gly  Gly  Leu  Gly  Asp  Lys  Val  Glu  Asp  Leu  Thr  Cys  Cys  His
               1420                    1425                         1430 cca  gag  cga  gaa  gca  gaa  ctg  agt  cac  ccc  agc  tct  gac  agt  gag              4384
Pro  Glu  Arg  Glu  Ala  Glu  Leu  Ser  His  Pro  Ser  Ser  Asp  Ser  Glu
               1435                    1440                         1445 gag  aat  gag  gcc  aaa  ggc  cgc  aga  gcc  acc  att  gca  ata  tcc  tcc              4429
Glu  Asn  Glu  Ala  Lys  Gly  Arg  Arg  Ala  Thr  Ile  Ala  Ile  Ser  Ser
               1450                    1455                         1460
```

```
cag gag ggt gat aac tca gag aga acc ctg tcc aac aac atc act    4474
Gln Glu Gly Asp Asn Ser Glu Arg Thr Leu Ser Asn Asn Ile Thr
            1465                1470                1475 gtt ccc aag ata gag cgc gcc aac agc tac tcg gca gag gag cca    4519
Val Pro Lys Ile Glu Arg Ala Asn Ser Tyr Ser Ala Glu Glu Pro
        1480                1485                1490 agt gcg cca tat gca cac acc agg aag agc ttc tcc atc agt gac    4564
Ser Ala Pro Tyr Ala His Thr Arg Lys Ser Phe Ser Ile Ser Asp
    1495                1500                1505 aaa ctc gac agg cag cgg aac aca gca agc ctg caa aat ccc ttc    4609
Lys Leu Asp Arg Gln Arg Asn Thr Ala Ser Leu Gln Asn Pro Phe
1510                1515                1520 cag aga agc aag tcc tcc aag ccg gag ggc cga ggg gac agc ctg    4654
Gln Arg Ser Lys Ser Ser Lys Pro Glu Gly Arg Gly Asp Ser Leu
            1525                1530                1535 tcc atg agg aga ctg tcc aga aca tcg gct ttc caa agc ttt gaa    4699
Ser Met Arg Arg Leu Ser Arg Thr Ser Ala Phe Gln Ser Phe Glu
        1540                1545                1550 agc aag cac aac taa accttcttaa tatccgccac agaaggctca agaatccagc    4754
Ser Lys His Asn cctaaaattc tctccaactc cagttttttcc cctttccttg aatcatacct gctttattct    4814
tagctgagca aaacaagcaa tgctttggga ggtgttaact caaaggtgac ttctgggcca    4874
cagatcaaga aagcatttga tctgacccag tgccagacac aggggattta aggcatgttc    4934
acacttgctg ggcagggagg gggaagagag ggagaaggaa gggttagaga tgaatgtgta    4994
tccgcagtca cagcagaaag ccatgagagc aggggaaaca aggggcttcg agcacgctcc    5054
atgccaggag gcatctgttg atttctgacc attatcaaga gttgtaggat gcagggct    5112

<210> SEQ ID NO 2
<211> LENGTH: 1554
<212> TYPE: PRT
<213> ORGANISM: Homo sapiens

<400> SEQUENCE: 2

Met Tyr Val Arg Val Ser Phe Asp Thr Lys Pro Asp Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
                165                 170                 175
```

```
Val Pro Val Val Ala Leu Ile Val Glu Gly Gly Pro Asn Val Ile Ser
            180                 185                 190

Ile Val Leu Glu Tyr Leu Arg Asp Thr Pro Val Pro Val Val
        195                 200                 205

Cys Asp Gly Ser Gly Arg Ala Ser Asp Ile Leu Ala Phe Gly His Lys
        210                 215                 220

Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
                245                 250                 255

His Leu Phe Ile Ile Leu Met Glu Cys Met Lys Lys Glu Leu Ile
        260                 265                 270

Thr Val Phe Arg Met Gly Ser Glu Gly His Gln Asp Ile Asp Leu Ala
        275                 280                 285

Ile Leu Thr Ala Leu Leu Lys Gly Ala Asn Ala Ser Ala Pro Asp Gln
        290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
                325                 330                 335

Met Leu Asp Ala Leu Val Leu Asp Arg Val Asp Phe Val Lys Leu Leu
        340                 345                 350

Ile Glu Asn Gly Val Ser Met His Arg Phe Leu Thr Ile Ser Arg Leu
        355                 360                 365

Glu Glu Leu Tyr Asn Thr Arg His Gly Pro Ser Asn Thr Leu Tyr His
        370                 375                 380

Leu Val Arg Asp Val Lys Lys Gly Asn Leu Pro Pro Asp Tyr Arg Ile
385                 390                 395                 400

Ser Leu Ile Asp Ile Gly Leu Val Ile Glu Tyr Leu Met Gly Gly Ala
                405                 410                 415

Tyr Arg Cys Asn Tyr Thr Arg Lys Arg Phe Arg Thr Leu Tyr His Asn
                420                 425                 430

Leu Phe Gly Pro Lys Arg Pro Lys Ala Leu Lys Leu Leu Gly Met Glu
        435                 440                 445

Asp Asp Ile Pro Leu Arg Arg Gly Arg Lys Thr Thr Lys Lys Arg Glu
        450                 455                 460

Glu Glu Val Asp Ile Asp Leu Asp Asp Pro Glu Ile Asn His Phe Pro
465                 470                 475                 480

Phe Pro Phe His Glu Leu Met Val Trp Ala Val Leu Met Lys Arg Gln
                485                 490                 495

Lys Met Ala Leu Phe Phe Trp Gln His Gly Glu Glu Ala Met Ala Lys
        500                 505                 510

Ala Leu Val Ala Cys Lys Leu Cys Lys Ala Met Ala His Glu Ala Ser
        515                 520                 525

Glu Asn Asp Met Val Asp Ile Ser Gln Glu Leu Asn His Asn Ser
        530                 535                 540

Arg Asp Phe Gly Gln Leu Ala Val Glu Leu Leu Asp Gln Ser Tyr Lys
545                 550                 555                 560

Gln Asp Glu Gln Leu Ala Met Lys Leu Leu Thr Tyr Glu Leu Lys Asn
                565                 570                 575

Trp Ser Asn Ala Thr Cys Leu Gln Leu Ala Val Ala Ala Lys His Arg
        580                 585                 590
```

-continued

```
Asp Phe Ile Ala His Thr Cys Ser Gln Met Leu Leu Thr Asp Met Trp
        595                 600                 605

Met Gly Arg Leu Arg Met Arg Lys Asn Ser Gly Leu Lys Val Ile Leu
    610                 615                 620

Gly Ile Leu Leu Pro Pro Ser Ile Leu Ser Leu Glu Phe Lys Asn Lys
625                 630                 635                 640

Asp Asp Met Pro Tyr Met Ser Gln Ala Gln Glu Ile His Leu Gln Glu
                645                 650                 655

Lys Glu Ala Glu Glu Pro Glu Lys Pro Thr Lys Glu Lys Glu Glu Glu
            660                 665                 670

Asp Met Glu Leu Thr Ala Met Leu Gly Arg Asn Asn Gly Glu Ser Ser
        675                 680                 685

Arg Lys Lys Asp Glu Glu Glu Val Gln Ser Lys His Arg Leu Ile Pro
    690                 695                 700

Leu Gly Arg Lys Ile Tyr Glu Phe Tyr Asn Ala Pro Ile Val Lys Phe
705                 710                 715                 720

Trp Phe Tyr Thr Leu Ala Tyr Ile Gly Tyr Leu Met Leu Phe Asn Tyr
                725                 730                 735

Ile Val Leu Val Lys Met Glu Arg Trp Pro Ser Thr Gln Glu Trp Ile
            740                 745                 750

Val Ile Ser Tyr Ile Phe Thr Leu Gly Ile Glu Lys Met Arg Glu Ile
        755                 760                 765

Leu Met Ser Glu Pro Gly Lys Leu Leu Gln Lys Val Lys Val Trp Leu
    770                 775                 780

Gln Glu Tyr Trp Asn Val Thr Asp Leu Ile Ala Ile Leu Leu Phe Ser
785                 790                 795                 800

Val Gly Met Ile Leu Arg Leu Gln Asp Gln Pro Phe Arg Ser Asp Gly
                805                 810                 815

Arg Val Ile Tyr Cys Val Asn Ile Ile Tyr Trp Tyr Ile Arg Leu Leu
            820                 825                 830

Asp Ile Phe Gly Val Asn Lys Tyr Leu Gly Pro Tyr Val Met Met Ile
        835                 840                 845

Gly Lys Met Met Ile Asp Met Met Tyr Phe Val Ile Ile Met Leu Val
    850                 855                 860

Val Leu Met Ser Phe Gly Val Ala Arg Gln Ala Ile Leu Phe Pro Asn
865                 870                 875                 880

Glu Glu Pro Ser Trp Lys Leu Ala Lys Asn Ile Phe Tyr Met Pro Tyr
                885                 890                 895

Trp Met Ile Tyr Gly Glu Val Phe Ala Asp Gln Ile Asp Pro Pro Cys
            900                 905                 910

Gly Gln Asn Glu Thr Arg Glu Asp Gly Lys Ile Ile Gln Leu Pro Pro
        915                 920                 925

Cys Lys Thr Gly Ala Trp Ile Val Pro Ala Ile Met Ala Cys Tyr Leu
    930                 935                 940

Leu Val Ala Asn Ile Leu Leu Val Asn Leu Leu Ile Ala Val Phe Asn
945                 950                 955                 960

Asn Thr Phe Phe Glu Val Lys Ser Ile Ser Asn Gln Val Trp Lys Phe
                965                 970                 975

Gln Arg Tyr Gln Leu Ile Met Thr Phe His Glu Arg Pro Val Leu Pro
            980                 985                 990

Pro Pro Leu Ile Ile Phe Ser His Met Thr Met Ile Phe Gln His Leu
    995                 1000                1005

Cys Cys Arg Trp Arg Lys His Glu Ser Asp Pro Asp Glu Arg Asp
```

-continued

```
                1010                1015                1020
Tyr Gly Leu Lys Leu Phe Ile Thr Asp Asp Glu Leu Lys Lys Val
    1025                1030                1035

His Asp Phe Glu Glu Gln Cys Ile Glu Glu Tyr Phe Arg Glu Lys
    1040                1045                1050

Asp Asp Arg Phe Asn Ser Ser Asn Asp Glu Arg Ile Arg Val Thr
    1055                1060                1065

Ser Glu Arg Val Glu Asn Met Ser Met Arg Leu Glu Glu Val Asn
    1070                1075                1080

Glu Arg Glu His Ser Met Lys Ala Ser Leu Gln Thr Val Asp Ile
    1085                1090                1095

Arg Leu Ala Gln Leu Glu Asp Leu Ile Gly Arg Met Ala Thr Ala
    1100                1105                1110

Leu Glu Arg Leu Thr Gly Leu Glu Arg Ala Glu Ser Asn Lys Ile
    1115                1120                1125

Arg Ser Arg Thr Ser Ser Asp Cys Thr Asp Ala Ala Tyr Ile Val
    1130                1135                1140

Arg Gln Ser Ser Phe Asn Ser Gln Glu Gly Asn Thr Phe Lys Leu
    1145                1150                1155

Gln Glu Ser Ile Asp Pro Ala Gly Glu Glu Thr Met Ser Pro Thr
    1160                1165                1170

Ser Pro Thr Leu Met Pro Arg Met Arg Ser His Ser Phe Tyr Ser
    1175                1180                1185

Val Asn Met Lys Asp Lys Gly Gly Ile Glu Lys Leu Glu Ser Ile
    1190                1195                1200

Phe Lys Glu Arg Ser Leu Ser Leu His Arg Ala Thr Ser Ser His
    1205                1210                1215

Ser Val Ala Lys Glu Pro Lys Ala Pro Ala Ala Pro Ala Asn Thr
    1220                1225                1230

Leu Ala Ile Val Pro Asp Ser Arg Arg Pro Ser Ser Cys Ile Asp
    1235                1240                1245

Ile Tyr Val Ser Ala Met Asp Glu Leu His Cys Asp Ile Asp Pro
    1250                1255                1260

Leu Asp Asn Ser Val Asn Ile Leu Gly Leu Gly Glu Pro Ser Phe
    1265                1270                1275

Ser Thr Pro Val Pro Ser Thr Ala Pro Ser Ser Ala Tyr Ala
    1280                1285                1290

Thr Leu Ala Pro Thr Asp Arg Pro Pro Ser Arg Ser Ile Asp Phe
    1295                1300                1305

Glu Asp Ile Thr Ser Met Asp Thr Arg Ser Phe Ser Ser Asp Tyr
    1310                1315                1320

Thr His Leu Pro Glu Cys Gln Asn Pro Trp Asp Ser Glu Pro Pro
    1325                1330                1335

Met Tyr His Thr Ile Glu Arg Ser Lys Ser Ser Arg Tyr Leu Ala
    1340                1345                1350

Thr Thr Pro Phe Leu Leu Glu Glu Ala Pro Ile Val Lys Ser His
    1355                1360                1365

Ser Phe Met Phe Ser Pro Arg Ser Tyr Tyr Ala Asn Phe Gly
    1370                1375                1380

Val Pro Val Lys Thr Ala Glu Tyr Thr Ser Ile Thr Asp Cys Ile
    1385                1390                1395

Asp Thr Arg Cys Val Asn Ala Pro Gln Ala Ile Ala Asp Arg Ala
    1400                1405                1410
```

-continued

```
Ala Phe Pro Gly Gly Leu Gly Asp Lys Val Glu Asp Leu Thr Cys
    1415                1420                1425

Cys His Pro Glu Arg Glu Ala Glu Leu Ser His Pro Ser Ser Asp
    1430                1435                1440

Ser Glu Asn Glu Ala Lys Gly Arg Arg Ala Thr Ile Ala Ile
    1445                1450                1455

Ser Ser Gln Glu Gly Asp Asn Ser Glu Arg Thr Leu Ser Asn Asn
    1460                1465                1470

Ile Thr Val Pro Lys Ile Glu Arg Ala Asn Ser Tyr Ser Ala Glu
    1475                1480                1485

Glu Pro Ser Ala Pro Tyr Ala His Thr Arg Lys Ser Phe Ser Ile
    1490                1495                1500

Ser Asp Lys Leu Asp Arg Gln Arg Asn Thr Ala Ser Leu Gln Asn
    1505                1510                1515

Pro Phe Gln Arg Ser Lys Ser Ser Lys Pro Glu Gly Arg Gly Asp
    1520                1525                1530

Ser Leu Ser Met Arg Arg Leu Ser Arg Thr Ser Ala Phe Gln Ser
    1535                1540                1545

Phe Glu Ser Lys His Asn
    1550

<210> SEQ ID NO 3
<211> LENGTH: 5179
<212> TYPE: DNA
<213> ORGANISM: Mus sp.
<220> FEATURE:
<221> NAME/KEY: CDS
<222> LOCATION: (218)..(4993)
<223> OTHER INFORMATION:

<400> SEQUENCE: 3
caaagacccc cataggtgtt gctgtggacg cctcataggc cagcatgttg gactcactcc      60
cagtatctct gtgcttcaga atgagaaaaa tgagagtcgc ctctcccgaa atgacatcca     120
gtctgagaag tggtctatca gcaaacacac tcagctcagc ccaacagacg cttttgggac     180
cattgagttc caaggaggtg gccattccaa caaagct atg tat gtc cga gta tct     235
                                        Met Tyr Val Arg Val Ser
                                          1               5 ttt gat acg aaa cct gat ctc ttg cta cac ctg atg acc aag gaa tgg     283
Phe Asp Thr Lys Pro Asp Leu Leu Leu His Leu Met Thr Lys Glu Trp
         10                  15                  20 caa ctg gag ctt ccg aaa ctt ctc atc tcc gtg cac gga ggg ctg cag     331
Gln Leu Glu Leu Pro Lys Leu Leu Ile Ser Val His Gly Gly Leu Gln
     25                  30                  35 aac ttt gaa ctc cag ccc aaa ctc aag caa gtc ttc ggg aag ggg ctc     379
Asn Phe Glu Leu Gln Pro Lys Leu Lys Gln Val Phe Gly Lys Gly Leu
 40                  45                  50 atc aaa gca gcc atg aca act gga gcc tgg atc ttc act gga ggg gtc     427
Ile Lys Ala Ala Met Thr Thr Gly Ala Trp Ile Phe Thr Gly Gly Val
55                  60                  65                  70 aac aca ggt gtc att cgt cat gtt gga gat gcc ttg aaa gac cat gca     475
Asn Thr Gly Val Ile Arg His Val Gly Asp Ala Leu Lys Asp His Ala
                 75                  80                  85 tct aag tct cga ggg aag ata tgt acc ata ggt atc gcc ccc tgg gga     523
Ser Lys Ser Arg Gly Lys Ile Cys Thr Ile Gly Ile Ala Pro Trp Gly
             90                  95                 100 att gtg gaa aac cag gaa gac ctg att gga aga gat gta gtc cga cca     571
Ile Val Glu Asn Gln Glu Asp Leu Ile Gly Arg Asp Val Val Arg Pro
```

-continued

```
                    105                     110                     115
tac cag acc atg tcc aat cct atg agc aag ctc acc gtt ctc aat agc        619
Tyr Gln Thr Met Ser Asn Pro Met Ser Lys Leu Thr Val Leu Asn Ser
    120                     125                     130 atg cac tcc cac ttc atc ctg gct gac aat ggg acc acg ggg aaa tac        667
Met His Ser His Phe Ile Leu Ala Asp Asn Gly Thr Thr Gly Lys Tyr
135                     140                     145                 150 gga gca gag gtg aaa ctc cgc aga caa ctg gaa aag cac att tca ctc        715
Gly Ala Glu Val Lys Leu Arg Arg Gln Leu Glu Lys His Ile Ser Leu
                155                     160                     165 cag aag ata aac aca aga tgc ctg ccg ttt ttc tct ctt gac tcc cgc        763
Gln Lys Ile Asn Thr Arg Cys Leu Pro Phe Phe Ser Leu Asp Ser Arg
            170                     175                     180 ttg ttt tat tca ttt tgg ggt agt tgc caa tta gac cca att gga atc        811
Leu Phe Tyr Ser Phe Trp Gly Ser Cys Gln Leu Asp Pro Ile Gly Ile
        185                     190                     195 ggt caa ggg gtt cca gtg gtg gct ctc atc gtg gaa gga gga ccc aat        859
Gly Gln Gly Val Pro Val Val Ala Leu Ile Val Glu Gly Gly Pro Asn
    200                     205                     210 gtg atc tca att gtt ttg gaa tac ctt cga gac acc cct cct gta cca        907
Val Ile Ser Ile Val Leu Glu Tyr Leu Arg Asp Thr Pro Pro Val Pro
215                     220                     225                 230 gtc gtg gtc tgt gat ggg agt gga cgg gca tcc gac atc ctg gca ttt        955
Val Val Val Cys Asp Gly Ser Gly Arg Ala Ser Asp Ile Leu Ala Phe
                235                     240                     245 ggg cat aaa tat tca gaa gaa ggc gga ctt atc aat gaa tct ttg agg       1003
Gly His Lys Tyr Ser Glu Glu Gly Gly Leu Ile Asn Glu Ser Leu Arg
            250                     255                     260 gac cag ctg ttg gtg aca ata cag aag acc ttc acg tac act cga acc       1051
Asp Gln Leu Leu Val Thr Ile Gln Lys Thr Phe Thr Tyr Thr Arg Thr
        265                     270                     275 caa gct cag cac ctg ttc atc atc ctc atg gaa tgc atg aag aag aag       1099
Gln Ala Gln His Leu Phe Ile Ile Leu Met Glu Cys Met Lys Lys Lys
    280                     285                     290 gaa ctg atc aca gtg ttt cga atg ggg tca gaa ggc cac cag gac att       1147
Glu Leu Ile Thr Val Phe Arg Met Gly Ser Glu Gly His Gln Asp Ile
295                     300                     305                 310 gat tta gct atc ctg aca gca tta ctc aaa ggt gcc aat gca tcc gcc       1195
Asp Leu Ala Ile Leu Thr Ala Leu Leu Lys Gly Ala Asn Ala Ser Ala
                315                     320                     325 cca gac caa ctg agc tta gct tta gcc tgg aac aga gtt gac atc gct       1243
Pro Asp Gln Leu Ser Leu Ala Leu Ala Trp Asn Arg Val Asp Ile Ala
            330                     335                     340 cgc agc cag atc ttt att tac ggg cag cag tgg ccg gta ggg tcc ctg       1291
Arg Ser Gln Ile Phe Ile Tyr Gly Gln Gln Trp Pro Val Gly Ser Leu
        345                     350                     355 gag caa gcc atg ctg gat gcc cta gtc ctg gac aga gtg gat ttt gtg       1339
Glu Gln Ala Met Leu Asp Ala Leu Val Leu Asp Arg Val Asp Phe Val
    360                     365                     370 aaa tta ctc ata gaa aat gga gta agc atg cac cgt ttt ctc acc atc       1387
Lys Leu Leu Ile Glu Asn Gly Val Ser Met His Arg Phe Leu Thr Ile
375                     380                     385                 390 tcc aga cta gag gaa ctg tac aat acg aga cat ggg ccc tca aat aca       1435
Ser Arg Leu Glu Glu Leu Tyr Asn Thr Arg His Gly Pro Ser Asn Thr
                395                     400                     405 ttg tac cac ttg gtc agg gat gtc aaa aag cga gag tat cca ggt ttc       1483
Leu Tyr His Leu Val Arg Asp Val Lys Lys Arg Glu Tyr Pro Gly Phe
            410                     415                     420 ggt tgg atc tat ttt aag gga aac ctg ccc ccg gac tac aga atc agc       1531
```

```
                                                                                    -continued Gly Trp Ile Tyr Phe Lys Gly Asn Leu Pro Pro Asp Tyr Arg Ile Ser
        425                 430                 435 ctg ata gac att ggc ctg gtg atc gag tac ctg atg ggc ggg gct tac     1579
Leu Ile Asp Ile Gly Leu Val Ile Glu Tyr Leu Met Gly Gly Ala Tyr
        440                 445                 450 cgc tgc aac tac acg cgc aag cgc ttt cgg acc ctc tac cac aat ctc     1627
Arg Cys Asn Tyr Thr Arg Lys Arg Phe Arg Thr Leu Tyr His Asn Leu
455                 460                 465                 470 ttt ggc ccc aaa aag ccc aaa gcc ttg aaa ctg ctg gga atg gag gat     1675
Phe Gly Pro Lys Lys Pro Lys Ala Leu Lys Leu Leu Gly Met Glu Asp
                475                 480                 485 gat att ccc ttg agg aga gga cgg aag aca act aar aag cgt gag gaa     1723
Asp Ile Pro Leu Arg Arg Gly Arg Lys Thr Thr Lys Lys Arg Glu Glu
            490                 495                 500 gag gtg gac atc gac ttg gat gat cct gag atc aac cac ttt cca ttc     1771
Glu Val Asp Ile Asp Leu Asp Asp Pro Glu Ile Asn His Phe Pro Phe
        505                 510                 515 ccc ttc cat gag ctg atg gtg tgg gcc gtc ctc atg aag aga caa aag     1819
Pro Phe His Glu Leu Met Val Trp Ala Val Leu Met Lys Arg Gln Lys
        520                 525                 530 atg gcc ctg ttc ttc tgg caa cac gga gag gag gcc atg gcc aaa gcc     1867
Met Ala Leu Phe Phe Trp Gln His Gly Glu Glu Ala Met Ala Lys Ala
535                 540                 545                 550 ctg gtg gcc tgc aag ctc tgc aag gcc atg gct cac gag gct tct gag     1915
Leu Val Ala Cys Lys Leu Cys Lys Ala Met Ala His Glu Ala Ser Glu
                555                 560                 565 aat gac atg gtc gat gac att tcc cag gag ctg aac cac aac tcc agg     1963
Asn Asp Met Val Asp Asp Ile Ser Gln Glu Leu Asn His Asn Ser Arg
            570                 575                 580 gac ttt ggc cag ctg gct gtg gag ctc ctg gac cag tcc tac aaa cag     2011
Asp Phe Gly Gln Leu Ala Val Glu Leu Leu Asp Gln Ser Tyr Lys Gln
        585                 590                 595 gat gag cag ctg gcc atg aag ctg ctg acg tat gag ctg aag aac tgg     2059
Asp Glu Gln Leu Ala Met Lys Leu Leu Thr Tyr Glu Leu Lys Asn Trp
        600                 605                 610 agt aat gcc aca tgc ctg cag ctg gct gtg gct gcc aag cac cgt gac     2107
Ser Asn Ala Thr Cys Leu Gln Leu Ala Val Ala Ala Lys His Arg Asp
615                 620                 625                 630 ttc att gca cac acg tgc agc cag atg tta ctt act gac atg tgg atg     2155
Phe Ile Ala His Thr Cys Ser Gln Met Leu Leu Thr Asp Met Trp Met
                635                 640                 645 gga cgg ctc cgg atg aga aag aac tca ggc ctc aag gta att ctg gga     2203
Gly Arg Leu Arg Met Arg Lys Asn Ser Gly Leu Lys Val Ile Leu Gly
            650                 655                 660 att cta ctt cct cct tca att ctc agc ttg gag ttc aag aac aaa gat     2251
Ile Leu Leu Pro Pro Ser Ile Leu Ser Leu Glu Phe Lys Asn Lys Asp
        665                 670                 675 gac atg ccc tat atg act cag gcc cag gag att cat ctc caa gag aag     2299
Asp Met Pro Tyr Met Thr Gln Ala Gln Glu Ile His Leu Gln Glu Lys
        680                 685                 690 gag ccg gag gag cca gag aag ccc aca aag gaa aaa gat gaa gag gac     2347
Glu Pro Glu Glu Pro Glu Lys Pro Thr Lys Glu Lys Asp Glu Glu Asp
695                 700                 705                 710 atg gag cta aca gca atg ttg ggg cga agc aat ggg gaa tca tcc aga     2395
Met Glu Leu Thr Ala Met Leu Gly Arg Ser Asn Gly Glu Ser Ser Arg
                715                 720                 725 aag aaa gat gaa gaa gaa gtt caa agc agg cac cgg cta atc ccc gtg     2443
Lys Lys Asp Glu Glu Glu Val Gln Ser Arg His Arg Leu Ile Pro Val
            730                 735                 740
```

```
ggc cga aaa atc tat gag ttc tac aac gca ccc atc gtg aag ttc tgg          2491
Gly Arg Lys Ile Tyr Glu Phe Tyr Asn Ala Pro Ile Val Lys Phe Trp
        745                 750                 755 ttc tac act ctg gcg tat att gga tac ctg atg ctc ttc aac tac atc          2539
Phe Tyr Thr Leu Ala Tyr Ile Gly Tyr Leu Met Leu Phe Asn Tyr Ile
    760                 765                 770 gtg tta gtg aag atg gag cgc tgg cct tcc act cag gaa tgg att gtc          2587
Val Leu Val Lys Met Glu Arg Trp Pro Ser Thr Gln Glu Trp Ile Val
775                 780                 785                 790 atc tcc tac att ttc act ctg gga ata gag aag atg aga gag atc ctg          2635
Ile Ser Tyr Ile Phe Thr Leu Gly Ile Glu Lys Met Arg Glu Ile Leu
                795                 800                 805 atg tcg gag ccg ggc aag ctg ctg cag aag gtg aag gtg tgg ctt cag          2683
Met Ser Glu Pro Gly Lys Leu Leu Gln Lys Val Lys Val Trp Leu Gln
            810                 815                 820 gag tac tgg aac gtc aca gac ctc atc gcc atc ctt ctc ttc tcg gtg          2731
Glu Tyr Trp Asn Val Thr Asp Leu Ile Ala Ile Leu Leu Phe Ser Val
        825                 830                 835 gga atg atc ctt cgt ctt caa gat cag ccc ttc agg agt gac ggg agg          2779
Gly Met Ile Leu Arg Leu Gln Asp Gln Pro Phe Arg Ser Asp Gly Arg
    840                 845                 850 gtc atc tac tgt gtg aac atc att tat tgg tat atc cgt ttg ctg gac          2827
Val Ile Tyr Cys Val Asn Ile Ile Tyr Trp Tyr Ile Arg Leu Leu Asp
855                 860                 865                 870 atc ttc ggc gtg aac aag tat ctg ggc cca tat gtg atg atg att ggg          2875
Ile Phe Gly Val Asn Lys Tyr Leu Gly Pro Tyr Val Met Met Ile Gly
                875                 880                 885 aaa atg atg ata gac atg atg tac ttt gtc atc att atg ctg gtg gtg          2923
Lys Met Met Ile Asp Met Met Tyr Phe Val Ile Ile Met Leu Val Val
            890                 895                 900 ctg atg agc ttt ggg gtc gcc agg caa gcc att ctc ttt ccc aat gag          2971
Leu Met Ser Phe Gly Val Ala Arg Gln Ala Ile Leu Phe Pro Asn Glu
        905                 910                 915 gag cca tct tgg aaa ctg gcc aag aat atc ttc tac atg cct tat tgg          3019
Glu Pro Ser Trp Lys Leu Ala Lys Asn Ile Phe Tyr Met Pro Tyr Trp
    920                 925                 930 atg att tat ggg gaa gtg ttt gct gac cag ata gac cct ccc tgt gga          3067
Met Ile Tyr Gly Glu Val Phe Ala Asp Gln Ile Asp Pro Pro Cys Gly
935                 940                 945                 950 cag aat gag acc cga gag gat ggc aag aca atc cag ctg ccc cca tgc          3115
Gln Asn Glu Thr Arg Glu Asp Gly Lys Thr Ile Gln Leu Pro Pro Cys
                955                 960                 965 aag aca gga gca tgg att gtc ccg gcc ata atg gcc tgc tac ctc ttg          3163
Lys Thr Gly Ala Trp Ile Val Pro Ala Ile Met Ala Cys Tyr Leu Leu
            970                 975                 980 gtg gcg aac atc ctt ctg gtc aac ctc ctt att gcc gtc ttc aac aat          3211
Val Ala Asn Ile Leu Leu Val Asn Leu Leu Ile Ala Val Phe Asn Asn
        985                 990                 995 aca ttt ttt gag gtc aag tcg ata tcc aac caa gta tgg aaa ttt           3256
Thr Phe Phe Glu Val Lys Ser Ile Ser Asn Gln Val Trp Lys Phe
    1000                1005                1010 cag agg tac cag ctc atc atg act ttc cac gag agg ccg gtt ctg           3301
Gln Arg Tyr Gln Leu Ile Met Thr Phe His Glu Arg Pro Val Leu
1015                1020                1025 ccc cca ccg ctc atc atc ttc agt cac atg acc atg atc ttc cac           3346
Pro Pro Pro Leu Ile Ile Phe Ser His Met Thr Met Ile Phe His
        1030                1035                1040 cat gtg tgc tgc cgg tgg agg aag cat gag agt gac cag gac gaa           3391
His Val Cys Cys Arg Trp Arg Lys His Glu Ser Asp Gln Asp Glu
    1045                1050                1055
```

```
                                                -continued agg gac tac ggc ctg aaa ctc ttc ata act gac gat gag ctc aag        3436
Arg Asp Tyr Gly Leu Lys Leu Phe Ile Thr Asp Asp Glu Leu Lys
    1060                1065                1070 aaa gta cac gat ttt gaa gag cag tgc ata gag gaa tat ttc cga        3481
Lys Val His Asp Phe Glu Glu Gln Cys Ile Glu Glu Tyr Phe Arg
    1075                1080                1085 gag aag gat gat cgc ttc aat tcg tcc aac gat gag agg ata cgt        3526
Glu Lys Asp Asp Arg Phe Asn Ser Ser Asn Asp Glu Arg Ile Arg
    1090                1095                1100 gtt aca tca gaa agg gtg gag aac atg tcc atg agg ctg gag gaa        3571
Val Thr Ser Glu Arg Val Glu Asn Met Ser Met Arg Leu Glu Glu
    1105                1110                1115 gtt aat gag aga gaa cat tcc atg aag gct tca ctc cag acc gtg        3616
Val Asn Glu Arg Glu His Ser Met Lys Ala Ser Leu Gln Thr Val
    1120                1125                1130 gac atc cgg cta gca cag cta gag gac ctc atc ggg cgc atg gcc        3661
Asp Ile Arg Leu Ala Gln Leu Glu Asp Leu Ile Gly Arg Met Ala
    1135                1140                1145 acc gcc ctg gag cgc ctg act ggt ctg gag cgg gca gag tct aac        3706
Thr Ala Leu Glu Arg Leu Thr Gly Leu Glu Arg Ala Glu Ser Asn
    1150                1155                1160 aaa atc cgc tca agg acc tcc tca gac tgc aca gat gca gcc tac        3751
Lys Ile Arg Ser Arg Thr Ser Ser Asp Cys Thr Asp Ala Ala Tyr
    1165                1170                1175 atc gtc cgc cag agc agc ttc aac agc cag gaa ggg aac acc ttc        3796
Ile Val Arg Gln Ser Ser Phe Asn Ser Gln Glu Gly Asn Thr Phe
    1180                1185                1190 aaa ctt caa gag agt ata gac cct gca ggt gag gag acc ata tcc        3841
Lys Leu Gln Glu Ser Ile Asp Pro Ala Gly Glu Glu Thr Ile Ser
    1195                1200                1205 cca act tct cca acc tta atg ccc cgt atg cga agc cat tct ttc        3886
Pro Thr Ser Pro Thr Leu Met Pro Arg Met Arg Ser His Ser Phe
    1210                1215                1220 tat tca gtc aat gtg aaa gac aaa ggt ggg ata gaa aag ttg gaa        3931
Tyr Ser Val Asn Val Lys Asp Lys Gly Gly Ile Glu Lys Leu Glu
    1225                1230                1235 agc att ttc aaa gaa agg tcc ctg agc tta cac cga gct act agc        3976
Ser Ile Phe Lys Glu Arg Ser Leu Ser Leu His Arg Ala Thr Ser
    1240                1245                1250 tcc cac tca gta gcc aaa gaa ccc aaa gct cct gca gcc cct gca        4021
Ser His Ser Val Ala Lys Glu Pro Lys Ala Pro Ala Ala Pro Ala
    1255                1260                1265 aac acc ttg gcc att gtt cct gac tcc aga aga cca tca tct tgc        4066
Asn Thr Leu Ala Ile Val Pro Asp Ser Arg Arg Pro Ser Ser Cys
    1270                1275                1280 ata gac atc tat gtc tct gcc atg gac gag ctc cac tgt gat ata        4111
Ile Asp Ile Tyr Val Ser Ala Met Asp Glu Leu His Cys Asp Ile
    1285                1290                1295 gag cct ctg gat aat tcc atg aac atc ctt ggg ctg ggt gag cca        4156
Glu Pro Leu Asp Asn Ser Met Asn Ile Leu Gly Leu Gly Glu Pro
    1300                1305                1310 agc ttt tca gct cta gca cct tcc aca acc ccg tca agt agt gcc        4201
Ser Phe Ser Ala Leu Ala Pro Ser Thr Thr Pro Ser Ser Ser Ala
    1315                1320                1325 tat gca acg ctc gca cct aca gac cga cct ccc agt agg agc att        4246
Tyr Ala Thr Leu Ala Pro Thr Asp Arg Pro Pro Ser Arg Ser Ile
    1330                1335                1340 gat ttt gaa gac ctc acc tcc atg gac act aga tct ttt tct tca        4291
Asp Phe Glu Asp Leu Thr Ser Met Asp Thr Arg Ser Phe Ser Ser
```

```
                1345                1350                1355
gac tat aca cac ctc cca gaa tgc caa aac ccc tgg gac aca gac         4336
Asp Tyr Thr His Leu Pro Glu Cys Gln Asn Pro Trp Asp Thr Asp
        1360                1365                1370 cct cca acg tac cat acc atc gag cgt tcc aag agt agc cgc tac         4381
Pro Pro Thr Tyr His Thr Ile Glu Arg Ser Lys Ser Ser Arg Tyr
    1375                1380                1385 cta gcc acc acg ccc ttt ctt ctg gaa gag gct ccc att gta aaa         4426
Leu Ala Thr Thr Pro Phe Leu Leu Glu Glu Ala Pro Ile Val Lys
1390                1395                1400 tcc cat agc ttt atg ttt tct cct tca agg agc tac tac gcc aac         4471
Ser His Ser Phe Met Phe Ser Pro Ser Arg Ser Tyr Tyr Ala Asn
        1405                1410                1415 ttt ggg gtg ccc gtg aaa acg gca gaa tac aca agt att aca gac         4516
Phe Gly Val Pro Val Lys Thr Ala Glu Tyr Thr Ser Ile Thr Asp
    1420                1425                1430 tgt atc gac aca aga tgt gtc aat gcc ccc caa gca ata gct gac         4561
Cys Ile Asp Thr Arg Cys Val Asn Ala Pro Gln Ala Ile Ala Asp
1435                1440                1445 cga gcc acc ttc cct gga ggt ctc gga gac aaa gtg gaa gat tta         4606
Arg Ala Thr Phe Pro Gly Gly Leu Gly Asp Lys Val Glu Asp Leu
        1450                1455                1460 tct tgt tgc cac cct gag cga gaa gca gag ctg agc cat cct agc         4651
Ser Cys Cys His Pro Glu Arg Glu Ala Glu Leu Ser His Pro Ser
    1465                1470                1475 tct gac agt gag gaa aat gag gcc aga ggc cag aga gct gcc aat         4696
Ser Asp Ser Glu Glu Asn Glu Ala Arg Gly Gln Arg Ala Ala Asn
1480                1485                1490 ccg ata tcc tct cag gag gct gaa aat gca gac aga acc cta tcc         4741
Pro Ile Ser Ser Gln Glu Ala Glu Asn Ala Asp Arg Thr Leu Ser
        1495                1500                1505 aac aac atc aca gtt ccc aag ata gag cgc gcc aac agc tac tca         4786
Asn Asn Ile Thr Val Pro Lys Ile Glu Arg Ala Asn Ser Tyr Ser
    1510                1515                1520 gca gag gag cca aac gtg cca tat gca cat acc aga aag agc ttc         4831
Ala Glu Glu Pro Asn Val Pro Tyr Ala His Thr Arg Lys Ser Phe
1525                1530                1535 tcc atc agt gac aag ctt gat aga cag agg aac acg gcg agc ctc         4876
Ser Ile Ser Asp Lys Leu Asp Arg Gln Arg Asn Thr Ala Ser Leu
        1540                1545                1550 cga aat ccc ttc cag aga agt aag tcc tcc aag ccg gag ggc cga         4921
Arg Asn Pro Phe Gln Arg Ser Lys Ser Ser Lys Pro Glu Gly Arg
    1555                1560                1565 ggg gac agc cta tcc atg agg aga ctg tct aga aca tcg gcc ttt         4966
Gly Asp Ser Leu Ser Met Arg Arg Leu Ser Arg Thr Ser Ala Phe
1570                1575                1580 cat agc ttt gaa agc aag cac aac taa accggcttac cgtgtgttgc           5013
His Ser Phe Glu Ser Lys His Asn
        1585                1590 aggaggctcg agaatccagc gctaaaattc tccccaatgc ccaccaccac gttccccctt   5073
ccttgagtta gacctgcttt attcttagct gagcaaaaca atgggagaca ttaactcaaa   5133
ggtaacctct gggccacagg tcaagcaagc attccatctg gtccag                  5179

<210> SEQ ID NO 4
<211> LENGTH: 1591
<212> TYPE: PRT
<213> ORGANISM: Mus sp.

<400> SEQUENCE: 4
```

```
Met Tyr Val Arg Val Ser Phe Asp Thr Lys Pro Asp Leu Leu Leu His
  1               5                  10                  15

Leu Met Thr Lys Glu Trp Gln Leu Glu Leu Pro Lys Leu Leu Ile Ser
             20                  25                  30

Val His Gly Gly Leu Gln Asn Phe Glu Leu Gln Pro Lys Leu Lys Gln
         35                  40                  45

Val Phe Gly Lys Gly Leu Ile Lys Ala Ala Met Thr Thr Gly Ala Trp
     50                  55                  60

Ile Phe Thr Gly Gly Val Asn Thr Gly Val Ile Arg His Val Gly Asp
 65              70                  75                      80

Ala Leu Lys Asp His Ala Ser Lys Ser Arg Gly Lys Ile Cys Thr Ile
                 85                  90                  95

Gly Ile Ala Pro Trp Gly Ile Val Glu Asn Gln Glu Asp Leu Ile Gly
             100                 105                 110

Arg Asp Val Val Arg Pro Tyr Gln Thr Met Ser Asn Pro Met Ser Lys
             115                 120                 125

Leu Thr Val Leu Asn Ser Met His Ser His Phe Ile Leu Ala Asp Asn
130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Cys Leu Pro Phe
                 165                 170                 175

Phe Ser Leu Asp Ser Arg Leu Phe Tyr Ser Phe Trp Gly Ser Cys Gln
             180                 185                 190

Leu Asp Pro Ile Gly Ile Gly Gln Gly Val Pro Val Val Ala Leu Ile
             195                 200                 205

Val Glu Gly Gly Pro Asn Val Ile Ser Ile Val Leu Glu Tyr Leu Arg
             210                 215                 220

Asp Thr Pro Pro Val Pro Val Val Cys Asp Gly Ser Gly Arg Ala
225                 230                 235                 240

Ser Asp Ile Leu Ala Phe Gly His Lys Tyr Ser Glu Glu Gly Gly Leu
             245                 250                 255

Ile Asn Glu Ser Leu Arg Asp Gln Leu Leu Val Thr Ile Gln Lys Thr
             260                 265                 270

Phe Thr Tyr Thr Arg Thr Gln Ala Gln His Leu Phe Ile Ile Leu Met
             275                 280                 285

Glu Cys Met Lys Lys Lys Glu Leu Ile Thr Val Phe Arg Met Gly Ser
             290                 295                 300

Glu Gly His Gln Asp Ile Asp Leu Ala Ile Leu Thr Ala Leu Leu Lys
305                 310                 315                 320

Gly Ala Asn Ala Ser Ala Pro Asp Gln Leu Ser Leu Ala Leu Ala Trp
             325                 330                 335

Asn Arg Val Asp Ile Ala Arg Ser Gln Ile Phe Ile Tyr Gly Gln Gln
             340                 345                 350

Trp Pro Val Gly Ser Leu Glu Gln Ala Met Leu Asp Ala Leu Val Leu
             355                 360                 365

Asp Arg Val Asp Phe Val Lys Leu Leu Ile Glu Asn Gly Val Ser Met
             370                 375                 380

His Arg Phe Leu Thr Ile Ser Arg Leu Glu Glu Leu Tyr Asn Thr Arg
385                 390                 395                 400

His Gly Pro Ser Asn Thr Leu Tyr His Leu Val Arg Asp Val Lys Lys
             405                 410                 415
```

-continued

```
Arg Glu Tyr Pro Gly Phe Gly Trp Ile Tyr Phe Lys Gly Asn Leu Pro
            420                 425                 430

Pro Asp Tyr Arg Ile Ser Leu Ile Asp Ile Gly Leu Val Ile Glu Tyr
            435                 440                 445

Leu Met Gly Gly Ala Tyr Arg Cys Asn Tyr Thr Arg Lys Arg Phe Arg
        450                 455                 460

Thr Leu Tyr His Asn Leu Phe Gly Pro Lys Lys Pro Lys Ala Leu Lys
465                 470                 475                 480

Leu Leu Gly Met Glu Asp Ile Pro Leu Arg Arg Gly Arg Lys Thr
                485                 490                 495

Thr Lys Lys Arg Glu Glu Val Asp Ile Asp Leu Asp Asp Pro Glu
            500                 505                 510

Ile Asn His Phe Pro Phe Pro Phe His Glu Leu Met Val Trp Ala Val
        515                 520                 525

Leu Met Lys Arg Gln Lys Met Ala Leu Phe Phe Trp Gln His Gly Glu
    530                 535                 540

Glu Ala Met Ala Lys Ala Leu Val Ala Cys Lys Leu Cys Lys Ala Met
545                 550                 555                 560

Ala His Glu Ala Ser Glu Asn Asp Met Val Asp Asp Ile Ser Gln Glu
                565                 570                 575

Leu Asn His Asn Ser Arg Asp Phe Gly Gln Leu Ala Val Glu Leu Leu
            580                 585                 590

Asp Gln Ser Tyr Lys Gln Asp Glu Gln Leu Ala Met Lys Leu Leu Thr
        595                 600                 605

Tyr Glu Leu Lys Asn Trp Ser Asn Ala Thr Cys Leu Gln Leu Ala Val
    610                 615                 620

Ala Ala Lys His Arg Asp Phe Ile Ala His Thr Cys Ser Gln Met Leu
625                 630                 635                 640

Leu Thr Asp Met Trp Met Gly Arg Leu Arg Met Arg Lys Asn Ser Gly
                645                 650                 655

Leu Lys Val Ile Leu Gly Ile Leu Leu Pro Pro Ser Ile Leu Ser Leu
            660                 665                 670

Glu Phe Lys Asn Lys Asp Asp Met Pro Tyr Met Thr Gln Ala Gln Glu
        675                 680                 685

Ile His Leu Gln Glu Lys Glu Pro Glu Pro Glu Lys Pro Thr Lys
    690                 695                 700

Glu Lys Asp Glu Glu Asp Met Glu Leu Thr Ala Met Leu Gly Arg Ser
705                 710                 715                 720

Asn Gly Glu Ser Ser Arg Lys Lys Asp Glu Glu Val Gln Ser Arg
                725                 730                 735

His Arg Leu Ile Pro Val Gly Arg Lys Ile Tyr Glu Phe Tyr Asn Ala
            740                 745                 750

Pro Ile Val Lys Phe Trp Phe Tyr Thr Leu Ala Tyr Ile Gly Tyr Leu
        755                 760                 765

Met Leu Phe Asn Tyr Ile Val Leu Val Lys Met Glu Arg Trp Pro Ser
    770                 775                 780

Thr Gln Glu Trp Ile Val Ile Ser Tyr Ile Phe Thr Leu Gly Ile Glu
785                 790                 795                 800

Lys Met Arg Glu Ile Leu Met Ser Glu Pro Gly Lys Leu Leu Gln Lys
                805                 810                 815

Val Lys Val Trp Leu Gln Glu Tyr Trp Asn Val Thr Asp Leu Ile Ala
            820                 825                 830

Ile Leu Leu Phe Ser Val Gly Met Ile Leu Arg Leu Gln Asp Gln Pro
```

-continued

```
                835                 840                 845
Phe Arg Ser Asp Gly Arg Val Ile Tyr Cys Val Asn Ile Ile Tyr Trp
    850                 855                 860
Tyr Ile Arg Leu Leu Asp Ile Phe Gly Val Asn Lys Tyr Leu Gly Pro
865                 870                 875                 880
Tyr Val Met Met Ile Gly Lys Met Met Ile Asp Met Met Tyr Phe Val
                    885                 890                 895
Ile Ile Met Leu Val Val Leu Met Ser Phe Gly Val Ala Arg Gln Ala
                900                 905                 910
Ile Leu Phe Pro Asn Glu Glu Pro Ser Trp Lys Leu Ala Lys Asn Ile
                915                 920                 925
Phe Tyr Met Pro Tyr Trp Met Ile Tyr Gly Glu Val Phe Ala Asp Gln
                930                 935                 940
Ile Asp Pro Pro Cys Gly Gln Asn Glu Thr Arg Glu Asp Gly Lys Thr
945                 950                 955                 960
Ile Gln Leu Pro Pro Cys Lys Thr Gly Ala Trp Ile Val Pro Ala Ile
                965                 970                 975
Met Ala Cys Tyr Leu Leu Val Ala Asn Ile Leu Leu Val Asn Leu Leu
                980                 985                 990
Ile Ala Val Phe Asn Asn Thr Phe  Phe Glu Val Lys Ser  Ile Ser Asn
            995                 1000                1005
Gln Val  Trp Lys Phe Gln Arg  Tyr Gln Leu Ile Met  Thr Phe His
    1010                1015                1020
Glu Arg  Pro Val Leu Pro  Pro Leu Ile Ile Phe  Ser His Met
    1025                1030                1035
Thr Met  Ile Phe His His Val  Cys Cys Arg Trp Arg  Lys His Glu
    1040                1045                1050
Ser Asp  Gln Asp Glu Arg Asp  Tyr Gly Leu Lys Leu  Phe Ile Thr
    1055                1060                1065
Asp Asp  Glu Leu Lys Lys Val  His Asp Phe Glu Glu  Gln Cys Ile
    1070                1075                1080
Glu Glu  Tyr Phe Arg Glu Lys  Asp Asp Arg Phe Asn  Ser Ser Asn
    1085                1090                1095
Asp Glu  Arg Ile Arg Val Thr  Ser Glu Arg Val Glu  Asn Met Ser
    1100                1105                1110
Met Arg  Leu Glu Glu Val Asn  Glu Arg Glu His Ser  Met Lys Ala
    1115                1120                1125
Ser Leu  Gln Thr Val Asp Ile  Arg Leu Ala Gln Leu  Glu Asp Leu
    1130                1135                1140
Ile Gly  Arg Met Ala Thr Ala  Leu Glu Arg Leu Thr  Gly Leu Glu
    1145                1150                1155
Arg Ala  Glu Ser Asn Lys Ile  Arg Ser Arg Thr Ser  Ser Asp Cys
    1160                1165                1170
Thr Asp  Ala Ala Tyr Ile Val  Arg Gln Ser Ser Phe  Asn Ser Gln
    1175                1180                1185
Glu Gly  Asn Thr Phe Lys Leu  Gln Glu Ser Ile Asp  Pro Ala Gly
    1190                1195                1200
Glu Glu  Thr Ile Ser Pro Thr  Ser Pro Thr Leu Met  Pro Arg Met
    1205                1210                1215
Arg Ser  His Ser Phe Tyr Ser  Val Asn Val Lys Asp  Lys Gly Gly
    1220                1225                1230
Ile Glu  Lys Leu Glu Ser Ile  Phe Lys Glu Arg Ser  Leu Ser Leu
    1235                1240                1245
```

His Arg Ala Thr Ser Ser His Ser Val Ala Lys Glu Pro Lys Ala
    1250                1255                1260

Pro Ala Ala Pro Ala Asn Thr Leu Ala Ile Val Pro Asp Ser Arg
1265                1270                1275

Arg Pro Ser Ser Cys Ile Asp Ile Tyr Val Ser Ala Met Asp Glu
        1280                1285                1290

Leu His Cys Asp Ile Glu Pro Leu Asp Asn Ser Met Asn Ile Leu
    1295                1300                1305

Gly Leu Gly Glu Pro Ser Phe Ser Ala Leu Ala Pro Ser Thr Thr
1310                1315                1320

Pro Ser Ser Ser Ala Tyr Ala Thr Leu Ala Pro Thr Asp Arg Pro
        1325                1330                1335

Pro Ser Arg Ser Ile Asp Phe Glu Asp Leu Thr Ser Met Asp Thr
    1340                1345                1350

Arg Ser Phe Ser Ser Asp Tyr Thr His Leu Pro Glu Cys Gln Asn
1355                1360                1365

Pro Trp Asp Thr Asp Pro Pro Thr Tyr His Thr Ile Glu Arg Ser
        1370                1375                1380

Lys Ser Ser Arg Tyr Leu Ala Thr Thr Pro Phe Leu Leu Glu Glu
    1385                1390                1395

Ala Pro Ile Val Lys Ser His Ser Phe Met Phe Ser Pro Ser Arg
1400                1405                1410

Ser Tyr Tyr Ala Asn Phe Gly Val Pro Val Lys Thr Ala Glu Tyr
        1415                1420                1425

Thr Ser Ile Thr Asp Cys Ile Asp Thr Arg Cys Val Asn Ala Pro
    1430                1435                1440

Gln Ala Ile Ala Asp Arg Ala Thr Phe Pro Gly Gly Leu Gly Asp
1445                1450                1455

Lys Val Glu Asp Leu Ser Cys Cys His Pro Glu Arg Glu Ala Glu
        1460                1465                1470

Leu Ser His Pro Ser Ser Asp Ser Glu Glu Asn Glu Ala Arg Gly
    1475                1480                1485

Gln Arg Ala Ala Asn Pro Ile Ser Ser Gln Glu Ala Glu Asn Ala
1490                1495                1500

Asp Arg Thr Leu Ser Asn Asn Ile Thr Val Pro Lys Ile Glu Arg
        1505                1510                1515

Ala Asn Ser Tyr Ser Ala Glu Glu Pro Asn Val Pro Tyr Ala His
    1520                1525                1530

Thr Arg Lys Ser Phe Ser Ile Ser Asp Lys Leu Asp Arg Gln Arg
1535                1540                1545

Asn Thr Ala Ser Leu Arg Asn Pro Phe Gln Arg Ser Lys Ser Ser
        1550                1555                1560

Lys Pro Glu Gly Arg Gly Asp Ser Leu Ser Met Arg Arg Leu Ser
    1565                1570                1575

Arg Thr Ser Ala Phe His Ser Phe Glu Ser Lys His Asn
1580                1585                1590

<210> SEQ ID NO 5
<211> LENGTH: 5038
<212> TYPE: DNA
<213> ORGANISM: Rattus sp.
<220> FEATURE:
<221> NAME/KEY: CDS
<222> LOCATION: (182)..(4882)
<223> OTHER INFORMATION:

<400> SEQUENCE: 5

```
aggccagcat gtcggactca ctcccagtat ctctgtgctt cagaatgaga aaaatgagag      60
tcgcctctcc cgaaatgaca tccagtctga gaagtggtct atcagcaaac acactcagct     120
cagcccaacg gatgcttttg ggactattga gttccaagga ggcggtcatt ccaacaaagc     180 c atg tat gtc cga gta tct ttt gat acg aaa cct gat ctc ttg cta cac     229
  Met Tyr Val Arg Val Ser Phe Asp Thr Lys Pro Asp Leu Leu Leu His
  1               5                  10                  15 ctg atg acc aag gaa tgg caa cta gag ctt ccc aaa ctt ctc atc tct       277
Leu Met Thr Lys Glu Trp Gln Leu Glu Leu Pro Lys Leu Leu Ile Ser
             20                  25                  30 gtg cac gga ggg ctg cag aac ttt gaa ctc cag ccc aaa ctc aag caa       325
Val His Gly Gly Leu Gln Asn Phe Glu Leu Gln Pro Lys Leu Lys Gln
         35                  40                  45 gtc ttc ggg aaa ggg ctc atc aaa gca gcc atg aca act gga gcc tgg       373
Val Phe Gly Lys Gly Leu Ile Lys Ala Ala Met Thr Thr Gly Ala Trp
     50                  55                  60 atc ttc act gga ggg gtc aac aca ggt gtc atc cgt cat gtg gga gat       421
Ile Phe Thr Gly Gly Val Asn Thr Gly Val Ile Arg His Val Gly Asp
 65                  70                  75                  80 gcc ttg aag gac cac gca tct aag tct cga ggg aag ata tgc acc ata       469
Ala Leu Lys Asp His Ala Ser Lys Ser Arg Gly Lys Ile Cys Thr Ile
                 85                  90                  95 ggt atc gca ccc tgg gga att gtg gaa aac cag gaa gac ctg atc gga       517
Gly Ile Ala Pro Trp Gly Ile Val Glu Asn Gln Glu Asp Leu Ile Gly
            100                 105                 110 aga gat gta gtc cga cca tac cag acc atg tca aac cct atg agc aag       565
Arg Asp Val Val Arg Pro Tyr Gln Thr Met Ser Asn Pro Met Ser Lys
        115                 120                 125 ctc acg gtt ctc aac agc atg cac tcc cac ttc atc ctg gct gac aat       613
Leu Thr Val Leu Asn Ser Met His Ser His Phe Ile Leu Ala Asp Asn
    130                 135                 140 ggg acc acg gga aaa tac ggg gcc gag gtg aaa ctc cgc aga caa ctg       661
Gly Thr Thr Gly Lys Tyr Gly Ala Glu Val Lys Leu Arg Arg Gln Leu
145                 150                 155                 160 gaa aag cac att tca ctc cag aag ata aac aca aga atc ggt caa ggg       709
Glu Lys His Ile Ser Leu Gln Lys Ile Asn Thr Arg Ile Gly Gln Gly
                165                 170                 175 gtt cca gtg gtg gcc ctc atc gtg gaa gga gga ccc aat gtg atc tca       757
Val Pro Val Val Ala Leu Ile Val Glu Gly Gly Pro Asn Val Ile Ser
            180                 185                 190 att gtt ttg gaa tac ctt cga gac acc cct cct gta cca gtc gtg gtc       805
Ile Val Leu Glu Tyr Leu Arg Asp Thr Pro Pro Val Pro Val Val Val
        195                 200                 205 tgc gat ggc agt gga cgg gca tcc gac att ctg gca ttt ggg cat aaa       853
Cys Asp Gly Ser Gly Arg Ala Ser Asp Ile Leu Ala Phe Gly His Lys
    210                 215                 220 tat tca gaa gaa ggc ggt ctt atc aat gaa tct ttg agg gac cag ctg       901
Tyr Ser Glu Glu Gly Gly Leu Ile Asn Glu Ser Leu Arg Asp Gln Leu
225                 230                 235                 240 ttg gtg aca ata cag aag acc ttc aca tac acc cgc acc caa gcc cag       949
Leu Val Thr Ile Gln Lys Thr Phe Thr Tyr Thr Arg Thr Gln Ala Gln
                245                 250                 255 cac ctg ttc atc atc ctc atg gaa tgc atg aag aag aag gaa ttg atc       997
His Leu Phe Ile Ile Leu Met Glu Cys Met Lys Lys Lys Glu Leu Ile
            260                 265                 270 aca gtg ttt cga atg gga tca gaa ggc cac cag gac att gat tta gct      1045
Thr Val Phe Arg Met Gly Ser Glu Gly His Gln Asp Ile Asp Leu Ala
```

-continued

```
                275                 280                 285
atc ctg aca gca cta ctc aaa gga gcc aat gca tcc gcc cca gac cag    1093
Ile Leu Thr Ala Leu Leu Lys Gly Ala Asn Ala Ser Ala Pro Asp Gln
        290                 295                 300 ctg agc tta gca tta gcc tgg aac aga gtt gac atc gct cgc agc cag    1141
Leu Ser Leu Ala Leu Ala Trp Asn Arg Val Asp Ile Ala Arg Ser Gln
305                 310                 315                 320 atc ttt att tac ggg cag cag tgg ccg gta ggg tcc ctg gag caa gcc    1189
Ile Phe Ile Tyr Gly Gln Gln Trp Pro Val Gly Ser Leu Glu Gln Ala
                325                 330                 335 atg ctg gat gcc cta gtc ctg gac aga gtg gac ttt gtg aaa tta ctc    1237
Met Leu Asp Ala Leu Val Leu Asp Arg Val Asp Phe Val Lys Leu Leu
        340                 345                 350 ata gaa aac gga gta agc atg cac cgt ttt ctc acc atc tcc aga cta    1285
Ile Glu Asn Gly Val Ser Met His Arg Phe Leu Thr Ile Ser Arg Leu
                355                 360                 365 gag gaa ctg tac aat acg aga cat ggg ccc tca aat aca ttg tac cac    1333
Glu Glu Leu Tyr Asn Thr Arg His Gly Pro Ser Asn Thr Leu Tyr His
        370                 375                 380 ttg gtc agg gat gtc aaa aag cga gag tat cca ggt ttc ggt tgg atc    1381
Leu Val Arg Asp Val Lys Lys Arg Glu Tyr Pro Gly Phe Gly Trp Ile
385                 390                 395                 400 tat ttt aag gga aac ctg ccc ccg gac tac aga atc agc ctg ata gac    1429
Tyr Phe Lys Gly Asn Leu Pro Pro Asp Tyr Arg Ile Ser Leu Ile Asp
                405                 410                 415 att ggc ctg gtg atc gag tac ctg atg ggc ggg gct tac cgc tgc aac    1477
Ile Gly Leu Val Ile Glu Tyr Leu Met Gly Gly Ala Tyr Arg Cys Asn
        420                 425                 430 tac aca cgc aag cgc ttt cgg acc ctc tac cac aat ctc ttt ggc ccc    1525
Tyr Thr Arg Lys Arg Phe Arg Thr Leu Tyr His Asn Leu Phe Gly Pro
                435                 440                 445 aaa agg ccc aaa gcc ttg aaa ctg ctg gga atg gag gat gat att ccc    1573
Lys Arg Pro Lys Ala Leu Lys Leu Leu Gly Met Glu Asp Asp Ile Pro
450                 455                 460 ttg agg aga gga aga aag aca act aag aaa cgt gag gaa gag gtg gac    1621
Leu Arg Arg Gly Arg Lys Thr Thr Lys Lys Arg Glu Glu Glu Val Asp
465                 470                 475                 480 ata gac ttg gat gac cct gag atc aac cac ttc cca ttc cct ttc cat    1669
Ile Asp Leu Asp Asp Pro Glu Ile Asn His Phe Pro Phe Pro Phe His
                485                 490                 495 gag ctg atg gtg tgg gct gtc ctc atg aag agg cag aag atg gcc ctg    1717
Glu Leu Met Val Trp Ala Val Leu Met Lys Arg Gln Lys Met Ala Leu
        500                 505                 510 ttc ttc tgg cag cat gga gag gag gcc atg gct aaa gcc ctg gtg gcc    1765
Phe Phe Trp Gln His Gly Glu Glu Ala Met Ala Lys Ala Leu Val Ala
                515                 520                 525 tgc aag ctc tgc aaa gcc atg gcc cat gag gct tct gag aat gat atg    1813
Cys Lys Leu Cys Lys Ala Met Ala His Glu Ala Ser Glu Asn Asp Met
530                 535                 540 gtg gat gac att tcc caa gag ctg aac cac aac tcc agg gac ttt ggc    1861
Val Asp Asp Ile Ser Gln Glu Leu Asn His Asn Ser Arg Asp Phe Gly
545                 550                 555                 560 cag ctg gct gtg gag ctt ttg gac cag tcc tac aaa cag gat gag cag    1909
Gln Leu Ala Val Glu Leu Leu Asp Gln Ser Tyr Lys Gln Asp Glu Gln
                565                 570                 575 ctg gcc atg aaa ctg ctg acg tat gag ttg aag aac tgg agc aat gcc    1957
Leu Ala Met Lys Leu Leu Thr Tyr Glu Leu Lys Asn Trp Ser Asn Ala
        580                 585                 590 aca tgc ctg cag ctg gct gtg gct gcc aag cac cgt gac ttc att gca    2005
```

```
            Thr Cys Leu Gln Leu Ala Val Ala Ala Lys His Arg Asp Phe Ile Ala
                    595                 600                 605 cac acg tgc agc cag atg tta ctt acc gac atg tgg atg gga cgg ctc         2053
His Thr Cys Ser Gln Met Leu Leu Thr Asp Met Trp Met Gly Arg Leu
            610                 615                 620 cgc atg cga aag aac tca ggc ctc aag gta att ctg gga att cta ctt         2101
Arg Met Arg Lys Asn Ser Gly Leu Lys Val Ile Leu Gly Ile Leu Leu
625                 630                 635                 640 cct cct tca att ctc agc ttg gag ttc aag aac aaa gat gac atg ccc         2149
Pro Pro Ser Ile Leu Ser Leu Glu Phe Lys Asn Lys Asp Asp Met Pro
                645                 650                 655 tat atg act cag gcc caa gaa att cat ctc caa gag aag gag ccg gag         2197
Tyr Met Thr Gln Ala Gln Glu Ile His Leu Gln Glu Lys Glu Pro Glu
            660                 665                 670 gaa ccg gag aag cct aca aag gaa aaa gat gaa gag gac atg gag cta         2245
Glu Pro Glu Lys Pro Thr Lys Glu Lys Asp Glu Glu Asp Met Glu Leu
        675                 680                 685 aca gca atg ttg gga cga aac aat ggg gag tca tcc aga aag aaa gac         2293
Thr Ala Met Leu Gly Arg Asn Asn Gly Glu Ser Ser Arg Lys Lys Asp
        690                 695                 700 gaa gaa gaa gtt caa agc agg cat cga cta atc cct gtg ggc cga aaa         2341
Glu Glu Glu Val Gln Ser Arg His Arg Leu Ile Pro Val Gly Arg Lys
705                 710                 715                 720 atc tat gag ttc tac aac gca ccc att gtg aag ttc tgg ttc tac act         2389
Ile Tyr Glu Phe Tyr Asn Ala Pro Ile Val Lys Phe Trp Phe Tyr Thr
                725                 730                 735 ctg gcg tac att gga tac ctg atg ctc ttc aat tac atc gtg ctg gtg         2437
Leu Ala Tyr Ile Gly Tyr Leu Met Leu Phe Asn Tyr Ile Val Leu Val
            740                 745                 750 aag atg gag cgc tgg cct tcc act cag gaa tgg atc gtc atc tcc tac         2485
Lys Met Glu Arg Trp Pro Ser Thr Gln Glu Trp Ile Val Ile Ser Tyr
        755                 760                 765 atc ttc act ctg gga ata gag aag atg aga gag atc ctg atg tca gag         2533
Ile Phe Thr Leu Gly Ile Glu Lys Met Arg Glu Ile Leu Met Ser Glu
        770                 775                 780 ccg ggc aag ctg ctg cag aaa gtc aaa gtg tgg ctg cag gag tac tgg         2581
Pro Gly Lys Leu Leu Gln Lys Val Lys Val Trp Leu Gln Glu Tyr Trp
785                 790                 795                 800 aac gtc acg gac ctc atc gcc atc ctc ctc ttc tcg gtg gga atg atc         2629
Asn Val Thr Asp Leu Ile Ala Ile Leu Leu Phe Ser Val Gly Met Ile
                805                 810                 815 ctt cgt ctt caa gac cag ccc ttc agg agt gac ggg agg gtc atc tac         2677
Leu Arg Leu Gln Asp Gln Pro Phe Arg Ser Asp Gly Arg Val Ile Tyr
            820                 825                 830 tgt gtg aac atc att tat tgg tat atc cgt tta cta gac atc ttc ggc         2725
Cys Val Asn Ile Ile Tyr Trp Tyr Ile Arg Leu Leu Asp Ile Phe Gly
        835                 840                 845 gtg aac aag tat ctg ggc cca tac gta atg atg att ggg aaa atg atg         2773
Val Asn Lys Tyr Leu Gly Pro Tyr Val Met Met Ile Gly Lys Met Met
        850                 855                 860 ata gac atg atg tac ttc gtc atc att atg ctg gtg gtg ctg atg agc         2821
Ile Asp Met Met Tyr Phe Val Ile Ile Met Leu Val Val Leu Met Ser
865                 870                 875                 880 ttt ggg gtc gcc agg caa gcc att ctc ttt ccc aat gag gag cca tct         2869
Phe Gly Val Ala Arg Gln Ala Ile Leu Phe Pro Asn Glu Glu Pro Ser
                885                 890                 895 tgg aaa ctg gcc aag aat atc ttc tac atg cct tat tgg atg att tat         2917
Trp Lys Leu Ala Lys Asn Ile Phe Tyr Met Pro Tyr Trp Met Ile Tyr
            900                 905                 910
```

```
ggg gaa gtg ttt gct gac cag ata gac cct ccc tgt gga cag aac gag      2965
Gly Glu Val Phe Ala Asp Gln Ile Asp Pro Pro Cys Gly Gln Asn Glu
            915                 920                 925 acc cga gag gat ggc aag aca atc cag ctg ccc cca tgc aag aca gga      3013
Thr Arg Glu Asp Gly Lys Thr Ile Gln Leu Pro Pro Cys Lys Thr Gly
    930                 935                 940 gca tgg att gtg cca gcc atc atg gcc tgc tac ctc tta gta gcg aac      3061
Ala Trp Ile Val Pro Ala Ile Met Ala Cys Tyr Leu Leu Val Ala Asn
945                 950                 955                 960 atc ctt ctg gtc aac ctc ctt att gct gtc ttc aac aat aca ttt ttt      3109
Ile Leu Leu Val Asn Leu Leu Ile Ala Val Phe Asn Asn Thr Phe Phe
                965                 970                 975 gag gtc aag tcg ata tcc aac caa gta tgg aaa ttt cag agg tac cag      3157
Glu Val Lys Ser Ile Ser Asn Gln Val Trp Lys Phe Gln Arg Tyr Gln
            980                 985                 990 ctc atc atg act ttc cat gag aga  cca gtt ctg cct cca  ccg ctc atc    3205
Leu Ile Met Thr Phe His Glu Arg  Pro Val Leu Pro Pro  Pro Leu Ile
            995                 1000                 1005 atc ttc agt cac atg acc atg  ata ttc cag cat gtg  tgc tgc cga        3250
Ile Phe Ser His Met Thr Met  Ile Phe Gln His Val  Cys Cys Arg
        1010                1015                 1020 tgg agg aag cat gag agt gac  ccg gat gaa agg gac  tac ggc ctg        3295
Trp Arg Lys His Glu Ser Asp  Pro Asp Glu Arg Asp  Tyr Gly Leu
        1025                1030                 1035 aaa ctc ttc ata act gat gat  gag ctc aag aaa gta  cat gat ttt        3340
Lys Leu Phe Ile Thr Asp Asp  Glu Leu Lys Lys Val  His Asp Phe
        1040                1045                 1050 gaa gag cag tgc ata gag gaa  tat ttc aga gag aag  gat gac cgc        3385
Glu Glu Gln Cys Ile Glu Glu  Tyr Phe Arg Glu Lys  Asp Asp Arg
        1055                1060                 1065 ttc aat tca tcc aat gat gag  agg ata cgg gtt acg  tca gaa agg        3430
Phe Asn Ser Ser Asn Asp Glu  Arg Ile Arg Val Thr  Ser Glu Arg
        1070                1075                 1080 gtg gag aac atg tcc atg agg  ctg gag gaa gtc aat  gag aga gaa        3475
Val Glu Asn Met Ser Met Arg  Leu Glu Glu Val Asn  Glu Arg Glu
        1085                1090                 1095 cat tcc atg aag gct tca ctc  cag act gtg gac atc  cgg cta gca        3520
His Ser Met Lys Ala Ser Leu  Gln Thr Val Asp Ile  Arg Leu Ala
        1100                1105                 1110 cag ctg gag gat ctc atc ggg  cgc atg gcc act gcc  ctg gag cgc        3565
Gln Leu Glu Asp Leu Ile Gly  Arg Met Ala Thr Ala  Leu Glu Arg
        1115                1120                 1125 cta aca ggt ctg gag cgg gca  gag tct aac aaa atc  cgc tca agg        3610
Leu Thr Gly Leu Glu Arg Ala  Glu Ser Asn Lys Ile  Arg Ser Arg
        1130                1135                 1140 acc tcc tca gac tgc aca gac  gca gcc tac atc gtc  cgc cag agc        3655
Thr Ser Ser Asp Cys Thr Asp  Ala Ala Tyr Ile Val  Arg Gln Ser
        1145                1150                 1155 agc ttc aac agt cag gaa ggg  aac acc ttc aaa ctt  caa gag agt        3700
Ser Phe Asn Ser Gln Glu Gly  Asn Thr Phe Lys Leu  Gln Glu Ser
        1160                1165                 1170 ata gac cct gca ggt gag gag  acc atg tcc cca act  tct cca acc        3745
Ile Asp Pro Ala Gly Glu Glu  Thr Met Ser Pro Thr  Ser Pro Thr
        1175                1180                 1185 tta atg ccc cgt atg cga agc  cat tct ttc tat tcg  gtc aat gtg        3790
Leu Met Pro Arg Met Arg Ser  His Ser Phe Tyr Ser  Val Asn Val
        1190                1195                 1200 aaa gac aaa ggt ggt ata gaa  aag ttg gag agc att  ttc aaa gaa        3835
Lys Asp Lys Gly Gly Ile Glu  Lys Leu Glu Ser Ile  Phe Lys Glu
        1205                1210                 1215
```

```
agg tcc ctg agc tta cac cgt gct act agc tcc cac tca gta gcc      3880
Arg Ser Leu Ser Leu His Arg Ala Thr Ser Ser His Ser Val Ala
1220                1225                1230 aag gag ccc aaa gct cct gca gcc cct gca aac acc ttg gcc att      3925
Lys Glu Pro Lys Ala Pro Ala Ala Pro Ala Asn Thr Leu Ala Ile
    1235                1240                1245 gtt cct gat tcc aga aga cca tcg tca tgc ata gac atc tat gtc      3970
Val Pro Asp Ser Arg Arg Pro Ser Ser Cys Ile Asp Ile Tyr Val
1250                1255                1260 tct gcc atg gat gag ctc cac tgt gat ata gac cct ctg gat aat      4015
Ser Ala Met Asp Glu Leu His Cys Asp Ile Asp Pro Leu Asp Asn
    1265                1270                1275 tcc atg aac atc ctt ggg ctg ggc gag cca agc ttt tca gct cta      4060
Ser Met Asn Ile Leu Gly Leu Gly Glu Pro Ser Phe Ser Ala Leu
1280                1285                1290 gca cct tcc aca gcc cct tca agc agt gcc tat gca acc ctt gca      4105
Ala Pro Ser Thr Ala Pro Ser Ser Ser Ala Tyr Ala Thr Leu Ala
    1295                1300                1305 cct aca gac cga cct cca agc agg agc att gat ttt gaa gac ctc      4150
Pro Thr Asp Arg Pro Pro Ser Arg Ser Ile Asp Phe Glu Asp Leu
1310                1315                1320 acc tcc atg gac act aga tct ttt tct tca gac tat acc cac ctc      4195
Thr Ser Met Asp Thr Arg Ser Phe Ser Ser Asp Tyr Thr His Leu
    1325                1330                1335 cca gaa tgc caa aac ccc tgg gac aca gac cct cca atg tac cat      4240
Pro Glu Cys Gln Asn Pro Trp Asp Thr Asp Pro Pro Met Tyr His
1340                1345                1350 acc atc gag cgt tcc aag agt agc cgc tac cta gcc act aca ccc      4285
Thr Ile Glu Arg Ser Lys Ser Ser Arg Tyr Leu Ala Thr Thr Pro
    1355                1360                1365 ttc ctt ctg gaa gag gcc ccc att gta aaa tcc cat agc ttt atg      4330
Phe Leu Leu Glu Glu Ala Pro Ile Val Lys Ser His Ser Phe Met
1370                1375                1380 ttt tct cct tca agg agt tac tac gcc aac ttt ggg gtg ccc gtg      4375
Phe Ser Pro Ser Arg Ser Tyr Tyr Ala Asn Phe Gly Val Pro Val
    1385                1390                1395 aaa aca gca gaa tac aca agt att aca gac tgt atc gac aca aga      4420
Lys Thr Ala Glu Tyr Thr Ser Ile Thr Asp Cys Ile Asp Thr Arg
1400                1405                1410 tgt gtc aat gcc ccc caa gca ata gct gac aga gcc acc ttc ccc      4465
Cys Val Asn Ala Pro Gln Ala Ile Ala Asp Arg Ala Thr Phe Pro
    1415                1420                1425 gga ggt ctc gga gac aaa gtg gaa gat tta tct tgt tgc cac cct      4510
Gly Gly Leu Gly Asp Lys Val Glu Asp Leu Ser Cys Cys His Pro
1430                1435                1440 gag cga gaa gca gag ctg agc cac cct agc tct gac agt gag gaa      4555
Glu Arg Glu Ala Glu Leu Ser His Pro Ser Ser Asp Ser Glu Glu
    1445                1450                1455 aat gag gcc aga ggc cgg aga gct gcc aat ccg ata tcc tct cag      4600
Asn Glu Ala Arg Gly Arg Arg Ala Ala Asn Pro Ile Ser Ser Gln
1460                1465                1470 gag act gaa aat gca gac aga acc cta tcc aac aac atc aca gtt      4645
Glu Thr Glu Asn Ala Asp Arg Thr Leu Ser Asn Asn Ile Thr Val
    1475                1480                1485 ccc aag ata gag cgc gcc aac agt tac tcg gca gag gag cca agc      4690
Pro Lys Ile Glu Arg Ala Asn Ser Tyr Ser Ala Glu Glu Pro Ser
1490                1495                1500 gcg cca tat gca cat acc aga aag agc ttc tcc atc agt gac aag      4735
Ala Pro Tyr Ala His Thr Arg Lys Ser Phe Ser Ile Ser Asp Lys
```

-continued

```
                1505                1510                1515
ctt gat  aga cag  agg aac  aca  gca agc  ctc cga  aat  ccc ttc  cag                4780
Leu Asp  Arg Gln  Arg Asn  Thr  Ala Ser  Leu Arg  Asn  Pro Phe  Gln
    1520               1525                    1530 aga agt  aag tcc  tcc aag  ccg  gag ggc  cga ggg  gac  agc gta  tcc                4825
Arg Ser  Lys Ser  Ser Lys  Pro  Glu Gly  Arg Gly  Asp  Ser Val  Ser
    1535               1540                    1545 atg aga  aga ctg  tct aga  aca  tcg gct  ttt cat  agc  ttt gag  agc                4870
Met Arg  Arg Leu  Ser Arg  Thr  Ser Ala  Phe His  Ser  Phe Glu  Ser
    1550               1555                    1560 aag cac  aac taa  accatcttcc cgtgtgttgc aggaggctca agaatccagc                       4922
Lys His  Asn
    1565 actaaaattc tcccccaatgc ccaccacgtt cccccattcct tgagttagac ctgctttttt                 4982 cttagctgag caaaacaaag ggagacatta actcaaaggt aacctctggg ccacgg                      5038
```

<210> SEQ ID NO 6
<211> LENGTH: 1566
<212> TYPE: PRT
<213> ORGANISM: Rattus sp.

<400> SEQUENCE: 6

```
Met Tyr Val Arg Val Ser Phe Asp Thr Lys Pro Asp Leu Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
                165                 170                 175

Val Pro Val Val Ala Leu Ile Val Glu Gly Gly Pro Asn Val Ile Ser
            180                 185                 190

Ile Val Leu Glu Tyr Leu Arg Asp Thr Pro Pro Val Pro Val Val Val
        195                 200                 205

Cys Asp Gly Ser Gly Arg Ala Ser Asp Ile Leu Ala Phe Gly His Lys
    210                 215                 220

Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
                245                 250                 255

His Leu Phe Ile Ile Leu Met Glu Cys Met Lys Lys Lys Glu Leu Ile
```

```
              260                 265                 270
Thr Val Phe Arg Met Gly Ser Glu Gly His Gln Asp Ile Asp Leu Ala
    275                 280                 285
Ile Leu Thr Ala Leu Leu Lys Gly Ala Asn Ala Ser Ala Pro Asp Gln
290                 295                 300
Leu Ser Leu Ala Leu Ala Trp Asn Arg Val Asp Ile Ala Arg Ser Gln
305                 310                 315                 320
Ile Phe Ile Tyr Gly Gln Gln Trp Pro Val Gly Ser Leu Glu Gln Ala
                325                 330                 335
Met Leu Asp Ala Leu Val Leu Asp Arg Val Asp Phe Val Lys Leu Leu
        340                 345                 350
Ile Glu Asn Gly Val Ser Met His Arg Phe Leu Thr Ile Ser Arg Leu
            355                 360                 365
Glu Glu Leu Tyr Asn Thr Arg His Gly Pro Ser Asn Thr Leu Tyr His
        370                 375                 380
Leu Val Arg Asp Val Lys Lys Arg Glu Tyr Pro Gly Phe Gly Trp Ile
385                 390                 395                 400
Tyr Phe Lys Gly Asn Leu Pro Pro Asp Tyr Arg Ile Ser Leu Ile Asp
                405                 410                 415
Ile Gly Leu Val Ile Glu Tyr Leu Met Gly Gly Ala Tyr Arg Cys Asn
            420                 425                 430
Tyr Thr Arg Lys Arg Phe Arg Thr Leu Tyr His Asn Leu Phe Gly Pro
        435                 440                 445
Lys Arg Pro Lys Ala Leu Lys Leu Leu Gly Met Glu Asp Asp Ile Pro
    450                 455                 460
Leu Arg Arg Gly Arg Lys Thr Thr Lys Arg Glu Glu Val Asp
465                 470                 475                 480
Ile Asp Leu Asp Asp Pro Glu Ile Asn His Phe Pro Phe Pro Phe His
                485                 490                 495
Glu Leu Met Val Trp Ala Val Leu Met Lys Arg Gln Lys Met Ala Leu
            500                 505                 510
Phe Phe Trp Gln His Gly Glu Glu Ala Met Ala Lys Ala Leu Val Ala
        515                 520                 525
Cys Lys Leu Cys Lys Ala Met Ala His Glu Ala Ser Glu Asn Asp Met
    530                 535                 540
Val Asp Asp Ile Ser Gln Glu Leu Asn His Asn Ser Arg Asp Phe Gly
545                 550                 555                 560
Gln Leu Ala Val Glu Leu Leu Asp Gln Ser Tyr Lys Gln Asp Glu Gln
                565                 570                 575
Leu Ala Met Lys Leu Leu Thr Tyr Glu Leu Lys Asn Trp Ser Asn Ala
            580                 585                 590
Thr Cys Leu Gln Leu Ala Val Ala Ala Lys His Arg Asp Phe Ile Ala
        595                 600                 605
His Thr Cys Ser Gln Met Leu Leu Thr Asp Met Trp Met Gly Arg Leu
    610                 615                 620
Arg Met Arg Lys Asn Ser Gly Leu Lys Val Ile Leu Gly Ile Leu Leu
625                 630                 635                 640
Pro Pro Ser Ile Leu Ser Leu Glu Phe Lys Asn Lys Asp Asp Met Pro
                645                 650                 655
Tyr Met Thr Gln Ala Gln Glu Ile His Leu Gln Glu Lys Glu Pro Glu
            660                 665                 670
Glu Pro Glu Lys Pro Thr Lys Glu Lys Asp Glu Glu Asp Met Glu Leu
        675                 680                 685
```

-continued

```
Thr Ala Met Leu Gly Arg Asn Asn Gly Glu Ser Ser Arg Lys Lys Asp
    690                 695                 700

Glu Glu Glu Val Gln Ser Arg His Arg Leu Ile Pro Val Gly Arg Lys
705                 710                 715                 720

Ile Tyr Glu Phe Tyr Asn Ala Pro Ile Val Lys Phe Trp Phe Tyr Thr
                725                 730                 735

Leu Ala Tyr Ile Gly Tyr Leu Met Leu Phe Asn Tyr Ile Val Leu Val
            740                 745                 750

Lys Met Glu Arg Trp Pro Ser Thr Gln Glu Trp Ile Val Ile Ser Tyr
        755                 760                 765

Ile Phe Thr Leu Gly Ile Glu Lys Met Arg Glu Ile Leu Met Ser Glu
    770                 775                 780

Pro Gly Lys Leu Leu Gln Lys Val Lys Val Trp Leu Gln Glu Tyr Trp
785                 790                 795                 800

Asn Val Thr Asp Leu Ile Ala Ile Leu Leu Phe Ser Val Gly Met Ile
                805                 810                 815

Leu Arg Leu Gln Asp Gln Pro Phe Arg Ser Asp Gly Arg Val Ile Tyr
            820                 825                 830

Cys Val Asn Ile Ile Tyr Trp Tyr Ile Arg Leu Leu Asp Ile Phe Gly
        835                 840                 845

Val Asn Lys Tyr Leu Gly Pro Tyr Val Met Met Ile Gly Lys Met Met
    850                 855                 860

Ile Asp Met Met Tyr Phe Val Ile Ile Met Leu Val Val Leu Met Ser
865                 870                 875                 880

Phe Gly Val Ala Arg Gln Ala Ile Leu Phe Pro Asn Glu Glu Pro Ser
                885                 890                 895

Trp Lys Leu Ala Lys Asn Ile Phe Tyr Met Pro Tyr Trp Met Ile Tyr
            900                 905                 910

Gly Glu Val Phe Ala Asp Gln Ile Asp Pro Pro Cys Gly Gln Asn Glu
        915                 920                 925

Thr Arg Glu Asp Gly Lys Thr Ile Gln Leu Pro Pro Cys Lys Thr Gly
    930                 935                 940

Ala Trp Ile Val Pro Ala Ile Met Ala Cys Tyr Leu Leu Val Ala Asn
945                 950                 955                 960

Ile Leu Leu Val Asn Leu Leu Ile Ala Val Phe Asn Asn Thr Phe Phe
                965                 970                 975

Glu Val Lys Ser Ile Ser Asn Gln Val Trp Lys Phe Gln Arg Tyr Gln
            980                 985                 990

Leu Ile Met Thr Phe His Glu Arg Pro Val Leu Pro Pro Pro Leu Ile
        995                 1000                1005

Ile Phe Ser His Met Thr Met Ile Phe Gln His Val Cys Cys Arg
    1010                1015                1020

Trp Arg Lys His Glu Ser Asp Pro Asp Glu Arg Asp Tyr Gly Leu
    1025                1030                1035

Lys Leu Phe Ile Thr Asp Asp Glu Leu Lys Lys Val His Asp Phe
    1040                1045                1050

Glu Glu Gln Cys Ile Glu Glu Tyr Phe Arg Glu Lys Asp Asp Arg
    1055                1060                1065

Phe Asn Ser Ser Asn Asp Glu Arg Ile Arg Val Thr Ser Glu Arg
    1070                1075                1080

Val Glu Asn Met Ser Met Arg Leu Glu Glu Val Asn Glu Arg Glu
    1085                1090                1095
```

```
His Ser Met Lys Ala Ser Leu Gln Thr Val Asp Ile Arg Leu Ala
    1100            1105            1110

Gln Leu Glu Asp Leu Ile Gly Arg Met Ala Thr Ala Leu Glu Arg
    1115            1120            1125

Leu Thr Gly Leu Glu Arg Ala Glu Ser Asn Lys Ile Arg Ser Arg
    1130            1135            1140

Thr Ser Ser Asp Cys Thr Asp Ala Ala Tyr Ile Val Arg Gln Ser
    1145            1150            1155

Ser Phe Asn Ser Gln Glu Gly Asn Thr Phe Lys Leu Gln Glu Ser
    1160            1165            1170

Ile Asp Pro Ala Gly Glu Glu Thr Met Ser Pro Thr Ser Pro Thr
    1175            1180            1185

Leu Met Pro Arg Met Arg Ser His Ser Phe Tyr Ser Val Asn Val
    1190            1195            1200

Lys Asp Lys Gly Gly Ile Glu Lys Leu Glu Ser Ile Phe Lys Glu
    1205            1210            1215

Arg Ser Leu Ser Leu His Arg Ala Thr Ser Ser His Ser Val Ala
    1220            1225            1230

Lys Glu Pro Lys Ala Pro Ala Ala Pro Ala Asn Thr Leu Ala Ile
    1235            1240            1245

Val Pro Asp Ser Arg Arg Pro Ser Ser Cys Ile Asp Ile Tyr Val
    1250            1255            1260

Ser Ala Met Asp Glu Leu His Cys Asp Ile Asp Pro Leu Asp Asn
    1265            1270            1275

Ser Met Asn Ile Leu Gly Leu Gly Glu Pro Ser Phe Ser Ala Leu
    1280            1285            1290

Ala Pro Ser Thr Ala Pro Ser Ser Ser Ala Tyr Ala Thr Leu Ala
    1295            1300            1305

Pro Thr Asp Arg Pro Pro Ser Arg Ser Ile Asp Phe Glu Asp Leu
    1310            1315            1320

Thr Ser Met Asp Thr Arg Ser Phe Ser Ser Asp Tyr Thr His Leu
    1325            1330            1335

Pro Glu Cys Gln Asn Pro Trp Asp Thr Asp Pro Pro Met Tyr His
    1340            1345            1350

Thr Ile Glu Arg Ser Lys Ser Ser Arg Tyr Leu Ala Thr Thr Pro
    1355            1360            1365

Phe Leu Leu Glu Glu Ala Pro Ile Val Lys Ser His Ser Phe Met
    1370            1375            1380

Phe Ser Pro Ser Arg Ser Tyr Tyr Ala Asn Phe Gly Val Pro Val
    1385            1390            1395

Lys Thr Ala Glu Tyr Thr Ser Ile Thr Asp Cys Ile Asp Thr Arg
    1400            1405            1410

Cys Val Asn Ala Pro Gln Ala Ile Ala Asp Arg Ala Thr Phe Pro
    1415            1420            1425

Gly Gly Leu Gly Asp Lys Val Glu Asp Leu Ser Cys Cys His Pro
    1430            1435            1440

Glu Arg Glu Ala Glu Leu Ser His Pro Ser Ser Asp Ser Glu Glu
    1445            1450            1455

Asn Glu Ala Arg Gly Arg Arg Ala Ala Asn Pro Ile Ser Ser Gln
    1460            1465            1470

Glu Thr Glu Asn Ala Asp Arg Thr Leu Ser Asn Asn Ile Thr Val
    1475            1480            1485

Pro Lys Ile Glu Arg Ala Asn Ser Tyr Ser Ala Glu Glu Pro Ser
```

```
            1490                1495                1500
Ala Pro Tyr Ala His Thr Arg Lys Ser Phe Ser Ile Ser Asp Lys
    1505                1510                1515

Leu Asp Arg Gln Arg Asn Thr Ala Ser Leu Arg Asn Pro Phe Gln
    1520                1525                1530

Arg Ser Lys Ser Ser Lys Pro Glu Gly Arg Gly Asp Ser Val Ser
    1535                1540                1545

Met Arg Arg Leu Ser Arg Thr Ser Ala Phe His Ser Phe Glu Ser
    1550                1555                1560

Lys His Asn
    1565

<210> SEQ ID NO 7
<211> LENGTH: 20
<212> TYPE: DNA
<213> ORGANISM: Homo sapiens

<400> SEQUENCE: 7
tgcttttggg accattgagt                                           20

<210> SEQ ID NO 8
<211> LENGTH: 20
<212> TYPE: DNA
<213> ORGANISM: Homo sapiens

<400> SEQUENCE: 8
agccctgcat cctacaactc                                           20

<210> SEQ ID NO 9
<211> LENGTH: 20
<212> TYPE: DNA
<213> ORGANISM: Homo sapiens

<400> SEQUENCE: 9
cgtgccagtg gttgtctgtg                                           20

<210> SEQ ID NO 10
<211> LENGTH: 22
<212> TYPE: DNA
<213> ORGANISM: Homo sapiens

<400> SEQUENCE: 10
tgagtattta tgcccaaagg cc                                        22

<210> SEQ ID NO 11
<211> LENGTH: 16
<212> TYPE: DNA
<213> ORGANISM: Mus sp.

<400> SEQUENCE: 11
caaagacccc catagg                                               16

<210> SEQ ID NO 12
<211> LENGTH: 20
<212> TYPE: DNA
<213> ORGANISM: Mus sp.

<400> SEQUENCE: 12
ctggaccaga tggaatgctt                                           20

<210> SEQ ID NO 13
```

```
<211> LENGTH: 20
<212> TYPE: DNA
<213> ORGANISM: Mus sp.

<400> SEQUENCE: 13
gccaagcacc gtgacttcat                                              20

<210> SEQ ID NO 14
<211> LENGTH: 17
<212> TYPE: DNA
<213> ORGANISM: Mus sp.

<400> SEQUENCE: 14
ggagccgtcc catccac                                                 17

<210> SEQ ID NO 15
<211> LENGTH: 21
<212> TYPE: DNA
<213> ORGANISM: Mus sp.

<400> SEQUENCE: 15
ttccacgaga ggccggttct g                                            21

<210> SEQ ID NO 16
<211> LENGTH: 22
<212> TYPE: DNA
<213> ORGANISM: Mus sp.

<400> SEQUENCE: 16
ctgctctggc ggacgatgta gg                                           22

<210> SEQ ID NO 17
<211> LENGTH: 20
<212> TYPE: DNA
<213> ORGANISM: Rattus sp.

<400> SEQUENCE: 17
aggccagcat gtcggactca                                              20

<210> SEQ ID NO 18
<211> LENGTH: 18
<212> TYPE: DNA
<213> ORGANISM: Rattus sp.

<400> SEQUENCE: 18
ccgtggccca gaggttac                                                18

<210> SEQ ID NO 19
<211> LENGTH: 21
<212> TYPE: DNA
<213> ORGANISM: Rattus sp.

<400> SEQUENCE: 19
ttccatgaga gaccagttct g                                            21

<210> SEQ ID NO 20
<211> LENGTH: 22
<212> TYPE: DNA
<213> ORGANISM: Rattus sp.

<400> SEQUENCE: 20
ctgctctggc ggacgatgta gg                                           22
```